(12) United States Patent
Burks, Jr. et al.

(10) Patent No.: US 7,485,708 B2
(45) Date of Patent: Feb. 3, 2009

(54) NUCLEIC ACIDS ENCODING ARA H 3 POLYPEPTIDES

(75) Inventors: A. Wesley Burks, Jr., Chapel Hill, NC (US); Gary A. Bannon, Wentzville, MO (US); Hugh A. Sampson, Larchmont, NY (US); Ricki M. Helm, Little Rock, AR (US); J. Steven Stanley, North Little Rock, AR (US); Patrick A. Rabjohn, Little Rock, AR (US)

(73) Assignee: University of Arkansas, Little Rock, AR (US)

( * ) Notice: Subject to any disclaimer, the term of this patent is extended or adjusted under 35 U.S.C. 154(b) by 372 days.

(21) Appl. No.: 10/228,806

(22) Filed: Aug. 26, 2002

(65) Prior Publication Data

US 2003/0049237 A1    Mar. 13, 2003

Related U.S. Application Data

(63) Continuation of application No. 09/141,220, filed on Aug. 27, 1998, now abandoned, which is a continuation-in-part of application No. 08/717,933, filed on Sep. 23, 1996, now abandoned.

(60) Provisional application No. 60/073,283, filed on Jan. 31, 1998, provisional application No. 60/074,590, filed on Feb. 13, 1998, provisional application No. 60/074,624, filed on Feb. 13, 1998, provisional application No. 60/074,633, filed on Feb. 13, 1998.

(51) Int. Cl.
    *C07H 21/04*    (2006.01)
(52) U.S. Cl. ...................... 536/23.1; 435/325; 530/370; 530/806; 530/868
(58) Field of Classification Search ........................ None
See application file for complete search history.

(56) References Cited

U.S. PATENT DOCUMENTS

| | | | |
|---|---|---|---|
| 3,645,852 A | 2/1972 | Axen et al. ................... 195/68 |
| 4,171,299 A | 10/1979 | Hamburger .............. 260/112.5 |
| 4,338,297 A | 7/1982 | Michael et al. ............... 424/91 |
| 3,720,760 A | 2/1984 | Bennich et al. ............ 436/51.3 |
| 4,469,677 A | 9/1984 | Michael et al. ............... 424/91 |
| 4,535,010 A | 8/1985 | Axen et al. ................. 427/246 |
| 4,579,840 A | 4/1986 | Hahn ............................ 514/14 |
| 4,658,022 A | 4/1987 | Knowles et al. ............ 530/402 |
| 4,659,678 A | 4/1987 | Forrest et al. ............... 436/512 |
| 4,696,915 A | 9/1987 | Horecker |
| 4,816,449 A | 3/1989 | Hahn .......................... 514/17 |
| 4,849,337 A | 7/1989 | Calenoff et al. ................ 435/7 |
| 4,849,404 A | 7/1989 | Iwai et al. ...................... 514/2 |
| 4,900,556 A | 2/1990 | Wheatley et al. ............ 424/450 |
| 4,959,314 A | 9/1990 | Mark et al. ................. 435/69.1 |
| 5,026,545 A | 6/1991 | Saint-Remy et al. |
| 5,049,390 A | 9/1991 | Wojdani ..................... 424/450 |
| 5,061,790 A | 10/1991 | Elting et al. ................. 530/402 |
| 5,091,318 A | 2/1992 | Anawis et al. .............. 436/513 |
| 5,169,933 A | 12/1992 | Anderson et al. ........ 531/391.3 |
| 5,314,991 A | 5/1994 | Oka et al. .................... 530/350 |
| 5,328,991 A | 7/1994 | Kuo ........................... 530/403 |
| 5,389,368 A | 2/1995 | Gurtiss, III |
| 5,449,669 A | 9/1995 | Metcalfe et al. ............... 514/13 |
| 5,480,972 A | 1/1996 | Avjioglu et al. ............. 530/379 |
| 5,486,452 A | 1/1996 | Gordon et al. .................. 435/5 |

(Continued)

FOREIGN PATENT DOCUMENTS

CA    2 157 596    9/1994

(Continued)

OTHER PUBLICATIONS

Colman et al., Research in Immunology, vol. 145, No. 1, 1994, pp. 33-36.*

(Continued)

*Primary Examiner*—Michael Szperka
(74) *Attorney, Agent, or Firm*—Choate, Hall & Stewart; Brenda Herschbach Jarrell; K. Nicole Clouse

(57) ABSTRACT

It has been determined that allergens, which are characterized by both humoral (IgE) and cellular (T cell) binding sites, can be modified to be less allergenic by modifying the IgE binding sites. The IgE binding sites can be converted to non-IgE binding sites by masking the site with a compound that prevents IgE binding or by altering as little as a single amino acid within the protein, most typically a hydrophobic residue towards the center of the IgE binding epitope, to eliminate IgE binding. The method allows the protein to be altered as minimally as possible, other than within the IgE-binding sites, while retaining the ability of the protein to activate T cells, and, in some embodiments by not significantly altering or decreasing IgG binding capacity. The examples use peanut allergens to demonstrate alteration of IgE binding sites. The critical amino acids within each of the IgE binding epitopes of the peanut protein that are important to immunoglobulin binding have been determined. Substitution of even a single amino acid within each of the epitopes led to loss of IgE binding. Although the epitopes shared no common amino acid sequence motif, the hydrophobic residues located in the center of the epitope appeared to be most critical to IgE binding.

9 Claims, 3 Drawing Sheets

U.S. PATENT DOCUMENTS

| | | | |
|---|---|---|---|
| 5,496,554 A | 3/1996 | Oka et al. | 424/276.1 |
| 5,543,144 A | 8/1996 | Chang | 424/133.1 |
| 5,547,669 A | 8/1996 | Rogers et al. | 424/185.1 |
| 5,558,869 A | 9/1996 | Burks, Jr. et al. | 424/276.1 |
| 5,583,046 A | 12/1996 | Valenta et al. | 435/320.1 |
| 5,591,433 A | 1/1997 | Michael et al. | 424/184.1 |
| 5,597,895 A | 1/1997 | Gaynor et al. | 530/324 |
| 5,616,559 A | 4/1997 | Androphy et al. | 514/12 |
| 5,625,039 A | 4/1997 | Washida et al. | 530/388.25 |
| 5,637,454 A | 6/1997 | Harley | 435/5 |
| 5,648,242 A | 7/1997 | Valenta et al. | 435/69.3 |
| 5,652,122 A | 7/1997 | Frankel et al. | 435/69.7 |
| 5,667,965 A | 9/1997 | Androphy et al. | 435/5 |
| 5,670,617 A | 9/1997 | Frankel et al. | 530/300 |
| 5,674,980 A | 10/1997 | Frankel et al. | 530/350 |
| 5,693,495 A | 12/1997 | Breiteneder et al. | 435/69.3 |
| 5,710,126 A | 1/1998 | Griffith et al. | 514/12 |
| 5,731,157 A | 3/1998 | Miller et al. | 435/7.4 |
| 5,736,149 A | 4/1998 | Avjioglu et al. | 424/275.1 |
| 5,747,641 A | 5/1998 | Frankel et al. | 530/300 |
| 5,759,572 A | 6/1998 | Sugimoto et al. | 424/450 |
| 5,773,003 A | 6/1998 | Swain et al. | 424/193.1 |
| 5,786,466 A | 7/1998 | Breitenbach et al. | 536/23.6 |
| 5,804,604 A | 9/1998 | Frankel et al. | 530/324 |
| 5,807,746 A | 9/1998 | Lin et al. | 435/375 |
| 5,820,862 A | 10/1998 | Garman et al. | 424/184.1 |
| 5,820,880 A | 10/1998 | Alving et al. | 424/450 |
| 5,830,463 A | 11/1998 | Duke et al. | |
| 5,837,550 A | 11/1998 | Breitenbach et al. | 436/513 |
| 5,843,672 A | 12/1998 | Morgenstern et al. | 435/7.1 |
| 5,843,710 A | 12/1998 | Cobon et al. | 435/69.1 |
| 5,869,040 A | 2/1999 | Oin | 424/93.21 |
| 5,888,762 A | 3/1999 | Joliot et al. | 435/69.1 |
| 5,888,799 A | 3/1999 | Curtiss, III | |
| 5,891,432 A | 4/1999 | Hoo | 424/93.21 |
| 5,891,716 A | 4/1999 | Morgenstern et al. | 435/325 |
| 5,939,283 A | 8/1999 | Morgenstern et al. | 435/69.1 |
| 5,973,121 A | 10/1999 | Burks, Jr. et al. | 530/370 |
| 5,989,814 A | 11/1999 | Frankel et al. | 435/6 |
| 5,998,583 A | 12/1999 | Korsmeyer | 530/350 |
| 6,008,340 A | 12/1999 | Ball et al. | 536/23.6 |
| 6,060,082 A | 5/2000 | Chen et al. | 424/450 |
| 6,187,311 B1 * | 2/2001 | Nishiyama et al. | 424/191.1 |
| 6,218,371 B1 | 4/2001 | Krieg et al. | 514/44 |
| 6,486,311 B1 | 11/2002 | Burks, Jr. et al. | 536/23.6 |
| 2002/0187158 A1 * | 12/2002 | Mahler et al. | 424/185.1 |

FOREIGN PATENT DOCUMENTS

| | | |
|---|---|---|
| CA | 2 158 047 | 9/1994 |
| EP | 0 819 763 | 1/1998 |
| EP | 0684812 | 1/1998 |
| EP | 0877033 | 11/1998 |
| JP | 072 85875 | 4/1994 |
| JP | 06253851 | 9/1994 |
| JP | 07095887 | 4/1995 |
| WO | WO 90/04025 | 4/1990 |
| WO | WO 91/06571 | 5/1991 |
| WO | WO 91/11718 | 8/1991 |
| WO | WO 92/02621 | 2/1992 |
| WO | WO 92/03551 | 3/1992 |
| WO | WO 92/11859 | 7/1992 |
| WO | WO 93/21223 | 10/1993 |
| WO | WO 94/05303 | 3/1994 |
| WO | WO 94/10194 | 5/1994 |
| WO | WO 94/20614 | 9/1994 |
| WO | WO 94/23035 | 10/1994 |
| WO | WO 94/24281 | 10/1994 |
| WO | WO 95/07933 | 3/1995 |
| WO | WO 95/34578 | 12/1995 |
| WO | WO 96/36880 | 11/1996 |
| WO | WO 97/05265 | 2/1997 |
| WO | WO 97/24139 | 7/1997 |
| WO | WO 98/32866 | 7/1998 |
| WO | WO 98/43657 | 8/1998 |
| WO | WO 98/39029 | 9/1998 |
| WO | WO 99/16467 | 4/1999 |
| WO | WO 99/25387 | 5/1999 |
| WO | WO 99/38978 | 5/1999 |
| WO | WO 99/34826 | 7/1999 |
| WO | WO 99/38978 | 8/1999 |
| WO | WO 99/49879 | 10/1999 |
| WO | WO 00/54803 | 9/2000 |
| WO | WO 01/36621 | 5/2001 |

OTHER PUBLICATIONS

Till et al., in Allergens and Allergen Immunotherapy, third edition, Marcel Dekker, Inc., 2004, pp. 85-104.*
Rabjohn et al., "Glycinin, a third major peanut allergen identified in soy-adsorbed serum IgE from peanut sensitive individuals" J. Allergy Clin. Immunol., Jan. 1998, vol. 101, No. 1 Part 2, pp. S240.*
Blumenthal et al., in Allergens and Allergen Immunotherapy, 3rd edition, 2004, Marcel Dekker, pp. 37-50.*
Burks et al., Eur J Biochem, 1997, 245:334-339.*
Reese et al., J Immunol, 2005, 175:8354-8364.*
Andrews, et al., *Gene*, 182(1-2): 101-9, 1996.
Bolhaar et al., Clin Exp Allergy, 35(12): 1638-44, 2005.
Dizier et al., *Genetic Epidemiology*, 16: 305-15, 1999.
Ferreira et al., *J. Exp. Med.*, 183: 599-609, 1996.
Ferreira et al., *The FASEB Journal*, 12: 231-42, 1998.
Gadermaier et al., *Int Arch Allergy Immunol.*, 139(1): 53-62, 2006.
Harvey, *Remington's Pharmaceutical Sciences*, 18$^{th}$ ed., Gennaro(ed), Mack Publishing Co., Easton, PA, 35: 697-724, 1990.
Holm, et al., *J. of Immunology*, 173: 5258-5267, 2004.
Kraft et al., *Int Arch Allergy Immunol*, 118: 171-76, 1999.
Li, et al., *The Journal of Immunology*, 162: 3045-3052, 1999.
Schramm et al., *The J. of Immunology*, 162: 2406-2414, 1999.
Scheurer et al., *Eur J Nutr*., 38(4): 201-15, 1999.
Swoboda et al., *Eur J Immunol*, 32(1): 270-80, 2002.
Walker, *Vaccine*, 12(5): 387-400, 1994.
Chatel, et al., "Various Factors (Allergen Nature, Mouse Strain, CpG/Recombinant Protein Expressed) Influence the Immune Response Elicited by Genetic Immunization", *Allergy*, 58: 641-647, 2003.
Evans, et al., "Non-Replicating Oral Whole Cell Vaccine Protective Against Enterotoxigenic *Escherichia coli* (ETEC) Diarrhea: Stimuation of Anti-CFA (CFA/I) and Anti-Enterotoxin (Anti-LT) Intestinal IgA and Protection Against Challenge with ETEC Belonging to Heterologous Serotypes", *FEMS Microbiology Immunology*, 47: 117-126, 1988.
Gotlieb, "Scientists Develop Vaccine Strategy for Peanut Allergy", *BMJ*, 318: 894, 1999.
Vrtala, et al., "Conversion of the Major Birch Pollen Allergen, Bet v 1, into Two Nonanaphylactic T Cell Epitope-Containing Fragments", *J. Clin. Invest*. 99(7): 1673-1681, 1997.
Del Val, et al., "Thioredoxin Treatment Increases Digestibility and Lowers Allergenicity of Milk", *J. Allergy Clin. Immunol.* 103(4): 690-697, 1999.
Hoyne, et al., "Peptide-Mediated Regulation of the Allergic Immune Response", *Immunol. Cell Biol*. 74(2): 180-186, 1996.
Vailes, et al., "Fine Specificity of B-Cell Epitopes on Felis Domesticus Allergen I (Fel d I): Effect of Reduction and Alkylation or Deglycosylation of Fel d I Structure and Antibody Binding", *J. Allergy Clin. Immunol.* 93(1): 22-33, 1994.
Burns, et al., "Selective Reduction of Disulfides by Tris (2-Carboxyethyl) Phosphine", *J. Org. Chem.* 56(8): 2648-2650, 1991.
Gray, et al., "Echistatin Disulfide Bridges: Selective Reduction and Linkage Assignment", *The Protein Society*, 1749-1755, 1993.
Gray, et al., "Disulfide Structures of Highly Bridged Peptides: A New Strategy for Analysis", *The Protein Society*,1732-1748, 1993.
Herbert, et al., "Reduction and Alkylation of Proteins in Preparation of Two-Dimensional Map Analysis: Why, When, and How?" *Electrophoresis*, 22: 2046-2057, 2001.

Nakamura, et al., "Mass Spectrometric-Based Revision of the Structure of a Cysteine-Rich Peptide Toxin with Gamma-Carboxyglutamic Acid, TxVIIA, from the Sea Snail, *Conus Textile*", *Protein Science*, 5(3): 524-530, 1996.

Olsson, et al., "Contribution of Disulphide Bonds to Antigenicity of Lep d 2, the Major Allergen of the Dust Mite *Lepidoglyphus destructor*", *Molecular Immunology*, 35: 1017-1023, 1998.

Smith, et al., "Localization of Antigenic Sites on Der p 2 Using Oligonucleotide-Directed Mutagenesis Targeted to Predicted Surface Residues", *Clinical and Experimental Allergy*, 27: 593-599, 1997.

Smith, et al., "Recombinant Allergens for Immunotherapy: A Der p 2 Variant with Reduced IgE Reactivity Retains T-Cell Epitopes", *J. Allergy Clin. Immunol.* 101(3): 423-425, 1998.

Smith, et al., "Reduction in IgE Binding to Allergen Variants Generated by Site-Directed Mutagenesis: Contribution of Disulfide Bonds to the Antigenic Structure of the Major House Dust Mite Allergen Der p 2", *Molecular Immunology*, 33(4/5): 399-405, 1996.

Watson, et al., "Trapping and Identification of Folding Intermediates of Disulfide Bond-Forming Proteins Based on Cyanylation, Cleavage, and Analysis by Mass Spectrometry", *Prot Sci.*, 7 : 1017-28, 1998.

Wu, et al., "A Novel Methodology for Assignment of Disulfide Bond Pairing in Proteins", *Protein Science*, 6(2): 391-398, 1997.

Zhou, et al., "Assignment of Disulfide Bonds in Proteins by Partial Acid Hydrolysis and Mass Spectrometry", *Journal of Protein Chemistry*, 9(5): 523-532, 1990.

Burks, et al., "Epitope Specificity of the Major Peanut Allergen, Ara h II", *J. Allergy Clin. Immunol.* 95: 607-611, 1995.

Gayler, et al., "Biosynthesis, cDNA and Amino Acid Sequences of a Precursor of Conglutin δ, A Sulphur-Rich Protein from Lupinus Angustifolius", *Plant Molecular Biology*, 15: 879-893, 1990.

Ichikawa, et al., "Solution Structure of Der f2, the Major Mite Allergen for Atopic Disease", *J. Mol. Chem.*, 273:356-360, 1998.

Medaglini, et al., "Mucosal and Systemic Immune Responses to a Recombinant Protein Expressed on the Surface of the Oral Commensal Bacterium *Streptococcus gordonii* After Oral Colonization", *Proceedings of the National Academy of Sciences of the United States of America*, 92(15): 6868-6872, 1995.

Nishiyama, et al., "Analysis of the IgE-epitope of Der f 2, a Major Mite Allergen, by in vitro Mutagenesis", *Mol. Immunol.*, 32: 1021-1029, 1995.

Nishiyama, et al., "Effects of Amino Acid Variations in Recombinant Der f II on its Human IgE and Mouse IgG Recognition", *Int. Arch. Allergy Immunol.*, 105: 62-69, 1994.

Takai, et al., "Effect of Proline Mutations in the Major House Dust Mite Allergen Der f 2 on IgE-binding and Histamine-releasing Activity", *Eur. J. Biochem.*, 267: 6650-6656, 2000.

Takai, et al., "Non-anaphylactic Combination of Partially Deleted Fragments of the Major House Dust Mite Allergen Der f 2 for Allergen-specific Immunotherapy", *Mol. Immunol.*, 36: 1055-1065, 1999.

Takai, et al., "Determination of the N- and C-terminal Sequences to Bind Human IgE of the Major House Dust Mite Allergen Der f 2 and Epitope Mapping for Monoclonal Antibodies", *Mol. Immunol.*, 34: 255-261, 1997.

Takai, et al., "Engineering of the Major House Dust Mite Allergen Der f 2 for Allergen-specific Immunotherapy", *Nat. Biotechnol.*, 15: 754-758, 1997.

Vrtala, et al., "Humoral Immune Responses to Recombinant Tree Pollen Allergens (Bet v 1 and Bet v II) in Mice: Construction of a Live Oral Allergy Vaccine", *International Archives of Allergy and Immunology*, 107: (1-3): 290-294, 1995.

EMBL Accession No. L77197 (Mar. 1996).

Amorim, et al., "Suppression of Airway Eosinophilia by Killed Mycobacterium Vaccae-Induced Allergen-Specific Regulatory T-Cells", *Nature Medicine*, 8(6): 625-629, 2002.

Asturias, et al., "Is Tropomyosin an Allergen in Anisakis?", *Allergy*, 55: 898-890, 2000.

Asturias, et al., "Cloning, Isolation, and IgE-Binding Properties of *Helix aspersa* (Brown Garden Snail) Tropomyosin", *Int. Arch Allergy Immunol.* 128: 90-96, 2002.

Asturias, et al., "Molecular Characterization of American Cockroach Tropomyosin (*Periplaneta americana* Allergen 7), a Cross-Reactive Allergen", *The Journal of Immunology*, 162: 4342-4348, 1999.

Bannon, et al., "Engineering, Characterization and in Vitro Efficacy of the Major Peanut Allergens for Use in Immunotherapy", *Int. Arch. Allergy Immunol*, 124: 70-72, 2001.

Barderas, et al., "Identification and Characterization of Che a 1 Allergen from *Chenopodium album* Pollen", *Int. Arch. Allergy Immunol.* 127: 47-54, 2002.

Barnes, P.J., "IL-10: A Key Regulator of Allergic Disease", *Clinical and Experimental Allergy*, 31: 667-669, 2001.

Bashir, et al., "An Enteric Helminth Infection Protects Against an Allergic Response to Dietary Antigen", *The Journal of Immunology*, 169: 3284-3292, 2002.

Batanero, et al., "Purification, Amino Acid Sequence and Immunological Characterization of Ole e 6, a Cysteine-Enriched Allergen from Olive Tree Pollen", *FEBS Letters*, 410: 293-296, 1997.

Beck, et al., "The Polyclonal and Antigen-Specific IgE and IgG Subclass Response of Mice Injected with Ovalbumin in Alum or Complete Freund's Adjuvant", *Cellular Immunology*, 123: 1-8, 1989.

Bissonnette, et al., "Inhibition of Mast Cell-Mediated Cytotoxicity by IFN-α/β and -γ[1]", *The Journal of Immunology*, 145: 3385-3390, 1990.

Bock, et al., "The Natural History of Food Sensitivity", *J. Allergy Clin. Immunol.* 69: 173-177, 1982.

Bock, et al., "Fatalities Due to Anaphylactic Reactions to Foods", *J. Allergy Clin. Immunol.* 107: 191-193, 2001.

Brandtzaeg, et al., "Current Understanding of Gastrointestinal Immunoregulation and Its Relation to Food Allergy", *Ann. N.Y. Acad. Sci.*, 964: 13-45, 2002.

Burks, et al., "Modification of a Major Peanut Allergen Leads to Loss of IgE Binding", *Int. Arch. Allergy Immunol.* 118: 313-314, 1999.

Bush, et al., "Molecular Cloning of a Major Alternaria Alternata Allergen, rAlt a 2", *J. Allergy Clin. Immunol.* 104: 665-671, 1999.

Chang, et al., "Characterization of Enolase Allergen from *Rhodotorula mucilaginosa*", *J. Biomed. Sci.* 9: 645-655, 2002.

Dandeu, et al., "Hydrophobic Interaction Chromatography for Isolation and Purification of Equ.c1, the Horse Major Allergen", *Journal of Chromatography*, 621: 23-31, 1993.

De Jong, et al., "Identification and Partial Characterization of Multiple Major Allergens in Peanut Proteins", *Clinical and Experimental Allergy*, 28: 743-751, 1998.

Diaz-Perales, et al., "Lipid-Transfer Proteins as Potential Plant Panallergens: Cross-Reactivity Among Proteins of Artemisia Pollen, Castanea Nut and Rosaceae Fruits, with Different IgE-Binding Capacities", *Clinical and Experimental Allergy*, 30: 1403-1410, 2000.

Diaz-Perales, et al., "Characterization of Asparagus Allergens: A Relevant Role of Lipid Transfer Proteins", *J. Allergy Clin. Immunol.* 110: 790-796, 2002.

Dorion, et al., "The Production of Interferon-γ in Response to a Major Peanut Allergy, Ara h II, Correlates with Serum Levels of IgE Anti-Ara h II", *J. Allergy Clin. Immunol.* 93: 93-99, 1994.

Durham, et al., "Immunologic Changes Associated with Allergen Immunotherapy", *The Journal of Allergy and Clinical Immunology*, 102(2): 157-164, 1998.

Erb, et al., "Atopic Disorders: A Default Pathway in the Absence of Infection?", *Immunol. Today*, 20:317-322, 1999.

Eriksson, et al., "Cloning and Characterisation of Group II Allergen from the Dust Mite *Tyrophagus putrescentiae*", *Eur. J. Biochem.* 251:443-447, 1998.

Eriksson, et al., "Cloning of Three New Allergens from the Dust Mite *Lepidoglyphus destructor* Using Phage Surface Display Technology", *Eur. J. Biochem.* 268: 287-294, 2001.

Fahlbusch, et al., "Purification and Partial Characterization of the Major Allergen, Cav p 1, from Guinea Pig *Cavia Porcellus*", *Allergy*, 57: 417-422, 2002.

Fiorentino, et al., "Two Types of Mouse T Helper Cell", *J. Exp. Med.* 170: 2081-2095, 1989.

Francis, et al., "Induction of IL-10$^+$CD4$^+$CD25$^{30}$ T Cells by Grass Pollen Immunotherapy", *J. Allergy Clin. Immunol.* 111: 1255-1261, 2003.

Gafvelin, et al., "Cross-Reactivity Studies of a New Group 2 Allergen from the Dust Mite *Glycyphagus domesticus*, Gly d 2, and Group 2 Allergens from *Dermatophagoides pteronyssinus, Lepidoglyphus destructor,* and *Tyrophagus putrescentiae* with Recombinant Allergens", *J. Allergy Clin. Immunol.* 107: 511-518, 2001.

Giuliani, et al., "Isolation and Purification of a Major Allergen from *Parietaria officinalis* Pollen", *Allergy*, 42: 434-440, 1987.

Hansen, et al., "Vaccination with Heat-Killed Listeria as Adjuvant Reverses Established Allergen-Induced Airway Hyperreactivity and Inflammation: Role of $CD8^+$ T Cells and IL-18", *The Journal of Immunology*, 164: 223-230, 2000.

Helm, et al., "Isolation and Characterization of a Clone Encoding a Major Allergen (Bla g Bd90K) Involved in IgE-Mediated Cockroach Hypersensitivity", *J. Allergy Clin. Immunol.* 98: 172-180, 1996.

Hilger, et al., "Sequence of the Gene Encoding cat (*Felis domesticus*) Serum Albumin", *Gene*, 169: 295-296, 1996.

Himly, et al., "Art v 1, the Major Allergen of Mugwort Pollen, is a Modular Glycoprotein with a Defensin-Like and a Hydroxyproline-Rich Domain", *FASEB J.*, 17: 106-108, 2003.

Hoffman, et al., "Occupational Allergy to Bumblebees: Allergens of *Bombus terrestris*", *J. Allergy Clin. Immunol.* 108: 855-860, 2001.

Hoffman, et al., "Allergens in Hymenoptera Venom XXVII: Bumblebee Venom Allergy and Allergens", *J. Allergy Clin. Immunol.* 97: 812-821, 1996.

Hoffman, et al., "Allergens in Bee Venom, III. Identification of Allergen B of Bee Venom as an Acid Phosphatase", *J. Allergy Clin. Immunol.* 59(5): 364-366, 1977.

Horiuti, et al., "Variable Expression of Pathogenesis-Related Protein Allergen in Mountain Cedar (*Juniperus ashei*) Pollen", *The Journal of Immunology*, 164: 2188-2192, 2000.

Horner, et al., "Identfiication of the Allergen Psi c 2 from the Basidiomycete Psilocybe Cubensis as a Fungal Cyclophilin". *Int. Arch Allergy Immunol.* 107: 298-300, 1995.

Howard, et al., "Regulation of B-Cell Growth and Differentiation by Soluble Factors", *Ann. Rev. Immunol.* 1: 307-333, 1983.

Hsu, et al., "Differential Effects of IL-4 and IL-4 and IL-10 on IL-2-Induced IFN-γ Synthesis and Lymphokine-Activated Killer Activity", *International Immunology*, 4(5): 563-569, 1992.

Ichikawa, et al., "Molecular Cloning, Expression and Modelling of Cat Allergen, Cystatin (Fel d 3), A Cysteine Protease Inhibitor", *Clinical and Experimental Allergy*, 31: 1279-1286, 2001.

Jankulovic, et al., "Isolation and Biochemical Characterization of a Thaumatin-Like Kiwi Allergen", *J. Allergy Clin. Immunol.* 110: 805-810, 2002.

Kalliomaki, et al., "Transforming Growth Factor-β in Breast Milk: A Potential Regular of Atopic Disease at an Early Age", *J. Allergy Clin. Immunol.* 104(6): 1251-1257, 1999.

Kleine-Tebbe, et al., "Severe Oral Allergy Syndrome and Anaphylactic Reactions Caused by a Bet v 1-Related PR-10 Protein in Soybean, SAM22", *J. Allergy Clin. Immunol.* 110: 797-804, 2002.

Kowalski, et al., "Mechanisms of Specific Immunotherapy of Allergic Diseases", *Allergy*, 53: 485-492, 1998.

Ledesman, et al., "Cloning, Expression and Characterization of a Novel Four EF-Hand $Ca^{2+}$-Binding Protein from Olive Pollen with Allergenic Activity", *FEBS Letter*, 466: 192-196, 2000.

Lee, et al., "Oral Administration of Il-12 Suppresses Anaphylactic Reactions in a Murine Model of Peanut Hypersensitivity", *Clinical Immunology*, 101(2): 220-228, 2001.

Leung, et al., "Effect of Anti-IgE Therapy in Patients with Peanut Allergy", *N. Engl. J. Med.* 348: 986-993, 2003.

Li, et al., "A Murine Model of Peanut Anaphylaxis: T- and B-Cell Responses to a Major Peanut Allergen Mimic Human Responses", *J. Allergy Clin. Immunol.* 106: 150-158, 2000.

Li, et al., "Novel Approaches for the Treatment of Food Allergy", *Current Opinion in Allergy and Clinical Immunology*, 2: 273-278, 2002.

Li, et al., "Engineered Recombinant Peanut Protein and Heat-Killed Listeria Monocytogenes Coadministration Protects Against Peanut-Induced Anaphylaxis in a Murine Model", *The Journal of Immunology*, 170: 3289-3295, 2003.

Li, et al., "Strain-Dependent Induction of Allergic Sensitization Caused by Peanut Allergen DNA Immunization in Mice", *The Journal of Immunology*, 162: 3045-3052, 1999.

Lombardero, et al., "cDNA Sequence Analysis of the Main Olive Allergen, Ole e I", *Clinical and Experimental Allergy*, 24: 765-770, 1994.

Lopata, et al., "Characteristics of Hypersensitivity Reactions and Indentification of a Unique 49 kd IgE-Binding Protein (Hal-m-1) in Abalone (*Haliotis midae*)", *J. Allergy Clin. Immunol.* 100: 642-648, 1997.

Lorentz, et al., "Human Intestinal Mast Cells Produce IL-5 in Vitro Upon IgE Receptor Cross-Linking and In Vivo in the Course of Intestinal Inflammatory Disease" *Eur. J. Immunol.* 29: 1496-1503, 1999.

Melen, et al., "Molecular Cloning of Per a 1 and Definition of the Cross-Reactive Group 1 Cockroach Allergens", *J. Allergy Clin. Immunol.* 103: 859-864, 1999.

Moneo, et al., "Isolation and Characterization of Tha p 1, A Major Allergen from the Pine Processionary Caterpillar *Thaumetopoea pityocampa*", *Allergy*, 58: 34-37, 2003.

Moneo, et al., "Isolation and Characterization of a Major Allergen from the Fish Parasite *Anisakis simplex*", *J. Allergy Clin. Immunol.* 106: 177-182, 2000.

Monsalve, et al.. "Detection, Isolation and Complete Amino Acid Sequence of an Aeroallergenic Protein from Rapeseed Flour", *Clinical and Experimental Allergy*, 27: 833-841, 1997.

Morafo, et al., "Genetic Susceptibility to Food Allergy is Linked to Differential $T_H^2$-$T_H^1$ Responses in C3H/HeJ and BALB/c Mice", *J. Allergy Clin. Immunol.* 111: 1122-1128, 2003.

Mosmann, et al., "Th1 and Th2 Cells: Different Patterns of Lymphokine Secretion Lead to Different Functional Properties", *Ann. Rev. Immunol.* 7: 145-173, 1989.

Mutius, et al., "The Environmental Predictors of Allergic Disease", *J. Allergy Clin. Immunol.* 105: 9-19, 2000.

Onishi, et al., "Two-Dimensional Electrophoresis of Malassezia Allergens for Atopic Dermatitis and Isolation of Mal f 4 Homologs with Mitochondrial Malate Dehydrogenase", *Eur. J. Biochem.* 261: 148-154, 1999.

Onizuka, et al., "Purification of the Major Allergen of Red Soft Coral (*Dendronephthya nipponica*)", *Int. Arch. Allergy Immunol*, 125: 135-143, 2001.

Oppenheimer, et al., "Treatment of Peanut Allergy with Rush Immunotherapy", *J. Allergy Clin. Immunol.* 90: 256-262, 1992.

Paddock, et al., "Identification, Cloning, and Recombinant Expression of Procalin, a Major Triatomine Allergen", *The Journal of Immunology*, 167: 2694-2699, 2001.

Palosuo, et al., "Wheat ω-5 Gliadin is a Major Allergen in Children with Immediate Allergy to Ingested Wheat", *J. Allergy Clin. Immunol.* 108: 634-638, 2001.

Pastorello, et al., "The Major Allergen of Sesame Seeds (*Sesamum indicum*) is a 2S Albumin", *Journal of Chromatography B*, 756: 85-93, 2001.

Pastorello, et al., "Allergenic Cross-Reactivity Among Peach, Apricot, Plum, and Cherry in Patients with Oral Allergy Syndrome: An In Vivo and in Vitro Study", *J. Allergy Clin. Immunol.* 94: 699-707, 1994.

Pierkes, et al., "Decreased Release of Histamine and Sulfidoleukotrienes by Human Peripheral Blood Leukocytes After Wasp Venom Immunotherapy is Partially Due to Induction of IL-10 and IFN-γ Production of T Cells", *J. Allergy Clin. Immunol.* 103: 326-332, 1999.

Pomes, et al., "Novel Allergen Structures with Tandem Amino Acid Repeats Derived from German and American Cockroach", *The Journal of Biological Chemistry*, 273(46): 30801-30807, 1998.

Ramos, et al., "cDNA Cloning and Expression of Blo t 11, the *Blomia tropicalis* Allergen Homologous to Paramyosin", *Int. Arch. Allergy Immunol.* 126: 286-293, 2001.

Rasool, et al., "Cloning, Characterization and Expression of Complete Coding Sequences of Three IgE Binding *Malassezia furfur* Allergens, Mal f 7, Mal f 8 and Mal f 9", *Eur. J. Biochem.* 267: 4355-4361, 2000.

Romagnani, et al., "The Role of Lymphocytes in Allergic Disease", *J. Allergy Clin. Immunol.* 105: 399-408, 2000.

Rook, et al., "Give us this Day our Daily Germs", *Immunology Today*, 19: 113-116, 1998.

Saarinen, et al., "Transforming Growth Factor-β1 in Mothers' Colostrum and Immune Responses to Cows' Milk Proteins in Infants with Cows' Milk Allergy", J. Allergy Clin. Immunol. 104: 1093-1098, 1999.

Saarne, et al., "Cloning and Characterisation of Two IgE-Binding Proteins, Homologous to Tropomyosin and α-Tubulin, from the Mite Lepidoglyphus destructor", Int. Arch Allergy Immunol. 130: 258-265, 2003.

Sampson, et al., "Fatal and Near-Fatal Anaphylactic Reactions to Food in Children and Adolescents", N. Engl. J. Med. 327: 380-384, 1992.

Sampson, Hugh., "Food Allergy. Part 1: Immunopathogenesis and Clinical Disorders", The Journal of Allergy and Clinical Immunology, 103(5): 717-728, 1999.

Sanchez-Monge, et al., "Isolation and Characterization of Relevant Allergens from Boiled Lentils", J. Allergy Clin. Immunol. 106: 955-961, 2000.

Santos, et al., "Cockroach Allergens and Asthma in Brazil: Identification of Tropomyosin as a Major Allergen with Potential Cross-Reactivity with Mite and Shrimp Allergens", J. Allergy Clin. Immunol. 104: 329-337, 1999.

Saxena, et al., "cDNA Cloning, Expression and Characterization of an Allergenic L3 Ribosomal Protein of Aspergillus fumigatus" Clin. Exp. Immunol, 134: 86-91, 2003.

Schade, et al., "Differences In Antigen-Specific T-Cell Responses Between Infants with Atopic Dermatitis with and without Cow's Milk Allergy: Relevance of $T_H2$ Cytokines", J. Allergy Clin. Immunol. 106: 1155-1162, 2000.

Shen, et al., "Characterization of Allergens from Penicillium Oxalicum and P. Notatum by Immunoblotting and N-Terminal Amino Acid Sequence Analysis", Clinical and Experimental Allergy, 29: 642-651, 1999.

Shen, et al., "Molecular Cloning and Immunological Characterization of the House Dues Mite Allergen Der f 7", Clinical and Experimental Allergy, 25: 1000-1006, 1995.

Sicherer, et al., "Prevalence of Peanut and Tree Nut Allergy in the US Determined by a Random Digit Dial Telephone Survey", J. Allergy Clin. Immunol. 103: 559-562, 1999.

Smith, et al., "Sequence Polymorphisms and Antibody Binding to the Group 2 Dust Mite Allergens", Int. Arch. Allergy Immunol. 124: 61-63, 2001.

Smith, et al., "The Molecular Basis of Antigenic Cross-Reactivity Between the Group 2 Mite Allergens", J. Allergy Clin Immunol. 107: 977-984, 2001.

Snapper, et al., "Interferon-γ and B Cell Stimulatory Factor-1 Reciprocally Regulate Ig Isotype Production", Science, 236: 944-947, 1987.

Sommergruber, et al., "Molecular Characterization of Dau c 1, the Bet v 1 Homologous Protein from Carrot and its Cross-Reactivity with Bet v 1 and Api g 1", Clinical and Experimental Allergy, 29: 840-847, 1999.

Stanley, et al., "Identification and Mutational Analysis of the Immunodominant IgE Binding Epitopes of the Major Peanut Allergen Ara h 2", Archives of Biochemistry and Biophysics, 342(2): 244-253, 1997.

Strobel, et al., "Immune Responses to Dietary Antigens: Oral Tolerance", Immunology Today, 19: 173-181, 1998.

Strobel, et al., "Oral Tolerance, Systemic Immunoregulation, and Autoimmunity" Ann. N.Y. Acad. Sci. 958: 47-58, 2002.

Tejera, et al., "Identification, Isolation, and Characterization of Ole e 7, a New Allergen of Olive Tree Pollen", J. Allergy Clin Immunol, 104: 797-802, 1999.

Tinghino, et al., "Molecular Characterization of a Cross-Reactive Juniperus oxycedrus Pollen Allergen, Jun o 2: A Novel Calcium-Binding Allergen", J. Allergy Clin Immunol, 101: 772-777, 1998.

Tsai, et al., "Sequence Analysis and Expression of a cDNA Clone Encoding a 98-kDa Allergen in Dermatophagoides farinae", Clinical and Experimental Allergy, 29: 1606-1613, 1999.

Turcanu, et al., "Characterization of Lymphocyte Responses to Peanuts in Normal Children, Peanut-Allergic Children, and Allergic Children who Acquired Tolerance to Peanuts", The Journal of Clinical Investigation, 111(7): 1065-1072, 2003.

Weiner, et al., "Oral Tolerance: Immune Mechanisms and Treatment of Autoimmune Diseases", Immunology Today, 18: 335-343, 1997.

Wopfner, et al., "Molecular and Immunological Characterization of Profilin from Mugwort Pollen", Biol. Chem. 383: 1779-1789, 2002.

Wu, et al., "Sequencing Analysis of cDNA Clones Encoding the American Cockroach Cr-PI Allergens", The Journal of Biological Chemistry, 271(30): 17937-17943, 1996.

Wu, et al., "Cloning of the American Cockroach Cr-PII Allergens: Evidence for the Existence of Cross-Reactive Allergens Between Species", J. Allergy Clin. Immunol, 101: 832-840, 1998.

Wu, et al., "Sequencing and Immunochemical Characterization of the American Cockroach Per a 3 (Cr-PI) Isoallergenic Variants", Molecular Immunology, 34(1): 1-8, 1997.

Xu, et al., "Cloning, Expression and Immunological Characterization of Ory s 1, the Major Allergen of Rice Pollen", Gene, 164: 255-259, 1995.

Yasueda, et al., "Identification and Cloning of Two Novel Allergens from the Lipophilic Yeast, Malassezia furfur", Biochemical and Biophysical Research Communications, 248: 240-244, 1998.

Yeung, et al., "Heat-Killed Listeria monocytogenes as an Adjuvant Converts Established Murine Th2-Dominated Immune Responses into Th1-Dominated Responses", The Journal of Immunology, 161: 4146-4152, 1998.

Yi, et al., "Identification of Shared and Unique Immunoglobulin E Epitopes of the Highly Conserved Tropomyosins in Blomia tropicalis and Dermatophagoides pteronyssinus", Clin. Exp. Allergy, 32: 1203-1210, 2002.

Yocum, et al., "Epidemiology of Anaphylaxis in Olmstead County: A Population-Based Study", J. Allergy Clin. Immunol. 104: 452-456, 1999.

Yokoyama, et al., "Purification, Identification, and cDNA Cloning of Jun a 2, the Second Major Allergen of Mountain Cedar Pollen", Biochemical and Biophysical Research Communications, 275: 195-202, 2000.

Yu, et al., "Proteomics and Immunological Analysis of a Novel Shrimp Allergen, Pen M 2", The Journal of Immunology, 170: 445-453, 2003.

Koppelman, et al., "Peanut Allergen Ara h 3: Isolation from peanuts and biochemical characterization", Allergy, 58: 1144-1151, 2003.

Triozzi, et al., "Effects of a β-Human Chorionic Gonadotropin Subunit Immunogen Administered in Aqueous Solution with a Novel Nonionic Block Copolymer Adjuvant in Patients with Advanced Cancer", Clinical Cancer Research, 3: 2355-2362, 1997.

AAS, et al., "Physico-Chemical Properties and Specific Activity of a Purified Allergen (Codfish)", Dev. Biol. Stand. 29: 90-98, 1975.

Aki, et al., "Immunochemical Characterization of Recombinant and Native Tropomyosins as a New Allergen from the House Dust Mite, Dermatophagoides farinae", J. Allergy Clin. Immunol., 96:74-83, 1995.

Alenius, et al., "Prohevein from the Rubber Tree (Hevea brasiliensis) is a Major Latex Allergen," Clin. Exp. Allergy, 25(7): 659-665, 1995.

Alenius, et al., "The Main IgE-Binding Epitope of a Major Latex Allergen, Prohevein, is Present in its N-Terminal 43-Amino Acid Fragment, Hevein" J. Immunol. 156(4): 1618-1625, 1996.

Alenius, et al., "IgE Reactivity to 14-kD and 27-kD Natural Rubber Proteins in Latex-Allergic Children with Spina Bifida and Other Congenital Anomalies", Int. Arch. Allergy Immunol., 102:61-66, 1993.

Ansari, et al., "An Investigation of Human Response to Pereninal Ryegrass", J. Allergy Clin. Immunol. 80: 229-235, 1987.

Ansair, et al., "Complete Amino Acid Sequence of a Lolium perenne (Perennial Rye Grass) Pollen Allergen, Lol p II" J. Biol. Chem., 264:11181-11185, 1989.

Ansair, "Complete Primary Structure of a Lolium perenne (Perrennial Rye Grass) Pollen Allergen, Lol p III: Comparison with Known Lol P I and II Sequences", Biochemistry, 28:8665-8670, 1989.

Apold, et al., "The Allergenic Structure of Allergen M from Cod. III. Studies on the Antigenic of Long-Sequence Peptides", Int Arch Allergy Appl Immunol. 58(3): 337-43, 1979.

Arruda, et al., "Molecular Cloning of a Major Cockroach (Blattella germanica) Allergen, Bla g 2", J. Biol. Chem., 270:19563-19568, 1995.

Arruda, et al., "Cloning of Cockroach Allergen, Bla g 4, Identifies Ligand Binding Proteins (or Calycins) as a Cause of IgE Antibody Responses" *J. Biol. Chem.* 270: 31196-31201, 1995.

Arruda, et al., "Molecular Cloning of German Cockroach (*Blattella germanica*) Allergens", *Int. Arch Allergy Immunol.*, 107:295-297, 1995.

Asturias, et al., "Cloning and High Level Expression of *Cynodon dactylon* (Bermuda Grass) Pollen Profilin (Cyn d 12) in *Escherichia coli*: Purification and Characterization of the Allergen" *Clin. Exp. Allergy*, 27:1307-1313, 1997.

Asturias, et al., "Cloning and Expression of the Panallergen Profilin and the Major Allergen (Ole e 1) from Olive Tree Pollen", *J. Allergy Clin Immunol* 100:365-372, 1997.

Attanayaka, et al., "Molecular Cloning and Nucleotide Sequencing of the Rubber Elongation Factor Gene from *Hevea brasilienis*", *Plant Mol. Biol.*, 16:1079-1081, 1991.

Aukrust, L., "Purification of Allergens in *Cladosporium herbarum*", *Allergy*, 35: 206-207, 1980.

Aukrust, et al., "Partial Purification and Characterization of Two *Cladosporium herbarum* Allergens", *Int Arch Allergy Appl Immunol.*, 60:68-79, 1979.

Avjioglu, et al., "Sequence Analysis of Sor H I, The Group I Allergen of Johnson Grass Pollen and Its Comparison to Rye-Grass Lol P I" *J. Allergy Clin. Immunol*. 91:340, 1993.

BSAC Working Party, "Position Paper on Allergen Immunotherapy," *Clin. Exp. Allergy*, 23: 1-44 (1993).

Ball, et al., "A Major Continuous Allergenic Epitope of Bovine Beta-Lactoglobulin Recognized by Human IgE Binding", *Clin. Exp. Allergy*, 24: 758-764, 1994.

Bannon, et al., "Tertiary Structure and Biophysical Properties of a Major Peanut Allergen, Implications for the Production of a Hypoallergenic Protein", *Int. Arch Allergy Immunol*. 118(2-4), 315-6, Feb.-Apr., 1999.

Bannon, et al., "Ara h 3, A Peanut Allergen Identified by Using Peanut Sensitive Patient Sera Adsorbed with Soy Proteins" Abstract, Jan. 1997.

Barnett, et al., "Multiplicity of Allergens in Peanuts," *J. Allergy Clin. Immunol.*, 72: 61-8, 1983.

Barnett, et al., "Partial Characterization of an Allergenic Glycoproteins from Peanut", *Biochimica et Biophysica Acta* 882: 97-105, 1986.

Batanero, et al., "Ole e 3, an Olive-Tree Allergen, Belongs to a Widespread Family of Pollen Proteins" *Eur. J. Biochem.*, 241:772-778, 1996.

Bauer, et al., "Modulation of the Allergic Immune Response in BALB/c Mice by Subcutaneo Injection of High Doses of the Dominant T Cell Epitope from the Major Birch Pollen Allergen Bet v 1", *Clin Exp Immunol*, 107(3): 536-41, Mar. 1997.

Bayard, et al., "Mapping of IgE Binding Regions in the Major Rat Urinary Protein, Alpha 2u-Globulin, Using Overlapping Peptides", *Immunol. Invest*, 28(5-6): 323-38, Sep.-Dec. 1999.

Bernhisel-Broadbent, et al., "Cross-Allergenicity in the Legume Botanical Family in Children with Food Hypersensitivity. II. Laboratory correlates" *J Allergy Clin. Immunol.*, 84: 701-709 (1989).

Bevier, "Flea Allergy Dermatitis Testing Breakthrough", *Canine Practice*, 22(2-3): 49-50, 1997.

Birkner, et al., "Evaluation of Immunotherapy-Induced Changes in Specific IgE, IgG, and IgG-subclasses in Birch Pollen-Allergic Patient by Means of Immunoblotting, Correlation with Clinical Response," *Allergy*, 45: 418-426, 1997.

Bock, "Natural History of Severe Reactions to Foods in Young Children," *J. Pediatr.* 107: 676-680, 1985.

Bock, "The Natural History of Peanut Allergy", *J. Allergy Clin. Immunol.*, 83: 900-904 (1989).

Bostros, H., "Cross-Antigenicity of Horse Serum Albumin with Dog and Cat Albumins: Study of Three Short Peptides with Siginificant Inhibitory Activity Towards Specific Human IgE and IgG Antibodies", *Immunology*, 88: 340-47, 1996.

Boulet, et al., "Inhibitory Effects of an Anti-IgE Antibody E25 on Allergen-Induced Early Asthmatic Response," *Am J. Respir Crit Care Med.*, 155: 1835-1840, 1997.

Brand, et al., "Allergen-Specific Immune Deviation from a TH2 to TH1 Response Induced by Dendritic Cells and Collagen Type 1", *J. Allergy Clin. Immunol.* 104(5): 1052-58, Nov. 1999.

Breiteneder, et al., "Diversity of Human T Cell Receptor Sequences of T Cell Clones with Specificit Bet v 1 Peptide/MHC II Complexes", *Adv Exp Med Biol*. 409:365-74, 1996.

Breiteneder, et al., "Four Recombinant Isoforms of Cor a I, the Major Allergen of Hazel Pollen, Show Different IgE-Bjnding Properties", *Europ. J. Biochem*. 212:355-362, 1993.

Breiteneder, et al., "Complementary DNA Cloning and Expression in *Escheria coli* of Aln g 1, the Major Allergen in Pollen odf alder (*Alnus glutinosa*)," *J. Allergy Clin. Immunol.*, 90: 909-917 (1992).

Briner, et al., "Peripheral T-Cell Tolerance Induced in Naive and Primed Mice by Subcutaneo Injection of Peptide From the Major Cat Allergen Fel D I", *Proc. Natl Acad Sci USA* , 90(16):7608-12, Aug. 15, 1993.

Bulone, A., "Separation of Horse Dander Allergen Proteins by Two-Dimesional Electrophoresis Molecular Characterisation and Identification of Equ c 2.0101 and Equ c 2.0102 as Lipocalin Proteins", *Eur J. Biochem*., 253:202-211, 1998.

Burks, et al., "Allergeicity of Peanut and Soybean Extracts Altered by Chemical or Thermal Denaturation in Patients with Atopic Dermatitis and Positive Food Challenges", *J. Allergy Clin Immunol*, 90(6 pt 1): 889-97, 1992.

Burks, et al., "Anaphylactic Reactions Following Gammaglibulin Administration in Patients with Hypgammaglobulinema: Detection of IgE antibodies to IgA,", *N. Eng. J. Med*. 314: 560-4, 1986.

Burks, et al., "Antibody Response to Milk Proteins in Patients with Milk-Protein Intolerance Documented by Challenge," *J. Allergy Clin. Immunol*. 85: 921-7, 1990.

Burks, et al., "Atopic Dermatitis: Clinical Relevance of Food Hypersensitivity Reactions", *J. Pediatr*.113: 447-451, 1988.

Burks et al., Cloning of the Ara H II Peanut Allergen by Polymerase Chain Reaction (PCR) Amplification, Abstract., J. Allergy Clin Immunol, 91 : 341, 1993.

Burks, et al., "The Identification of A Family of Vicilin-Like Genes Encoding Allergens Responsible for Peanut Hyper-Sensitivity", Abstract.

Burks, et al., Epitope Specificity and Immunoaffinity Purification of the Major Peanut Allergen, Ara h 1,, *J. Allergy Clin Immunol*. 93(4): 743-50 (1994).

Burks, et al., "Identification and Characterization of a Second Major Peanut Allergen, Ara h II, with Use of the Sera of Patients with Atopic Dermatitis and Positive Peanut Challenge," *J Allergy Clin Immunol*.. 90(6 pt 1):962-9 (1992).

Burks, et al., "Identification of a Second Major Peanut Allergen in Patients with Atopic Dermatitis and Peanut Hypersensivity," J. Allergy Clin. Immunol. 87:211, 1991.

Burks, et al., "Identification of Peanut Agglutinin and Soybean Trypsin Inhibitor as Minor Legume Allergens," *Int Arch Allergy Immunol*. 105(2): 143-9, 1994.

Burks, et al., "Identification of a Major Peanut Allergen Ara h 1, in Patients with Atopic Dermatitis and Positive Peanut Challenge," *J. Allergy Clin. Immunol*. 88, 172-179, 1991.

Burks, et al., "Isolation, Identification, and Characterization of Clones Encoding Antigens Responsible for Peanut Hypersensitivity", *Int. Arch. Allergy Immunol*. 107(1-3): 248-50, May-Jun. 1995.

Burks, et al., "Mapping and Mutational Analysis of the IgE-Binding Epitopes on Ara h 1, a Legume Vicilin Protein and a Major Allergen in Peanut Hypersensitvity", *Eur. J. Biochem*. 245(2): 334-9, Apr. 1997.

Burks, et al., "Modification of a Major Peanut Allergen Leads to Loss of IgE Binding", *Int. Arch Allergy Immunol*. 118(2-4), 313-4, Feb.-Apr. 1999.

Burks, et al., "Peanut Allergens", Allergy, 53(8): 725-30, Aug. 1998.

Burks, et al., Production of Murine Monoclonal (mAb) Antibodies to Ara H1, A 63.5 kD Allergen in Peanuts, *J. Allergy Clin. Immunol*. 87: 210, 1991.

Burks, et al., "Recombinant Peanut Allergen Ara h I Expression and IgE Binding in Patients with Peanut Hypersensitivity", *J. Clin. Invest*. 96(4): 1715-21, Oct. 1996.

Burks, et al., "Cloning, Epitope Mapping and Mutational Analysis of Ara H 2, A Major Peanut Allergen", Abstract, 1997.

Butch, et al., "Properties of Human Follicular Dendritic Cells Purified with HJ2, a New Monoclonal Antibody", *Cellular Immunology*, 155, 27-41 (1994).

Cardaba, et al., "Antibody Response to Olive Pollen Antigens: Association Between HLA Class II Genes and IgE Response to Ole e I" *J. Allergy Clin. Immunol.* 91:338, 1993.

Chaloin, et al., "Conformations of Primary Amphipathic Carrier Peptides in Membrane Mimicking Environments", *Biochemistry*, 36: 11179-11187, 1997.

Chapman, et al., "Purification of Allergens," *Curr. Opin. Immunol.*, 1: 647-53, 1989.

Chen, et al., "Allergenic and Antigenic Determinants of Latex Allergen Hev B 1: Peptide Mapping of Epitopes Recognized by Human, Murine and Rabbit Antibodies", *Clin Exp Allergy*, 26(4): 406-15, Apr. 1996.

Chen, et al., "Isolation and Identification of Hevein as a Major IgE-Binding Polypeptide in Hevea Latex," *J. Allergy Clin. Immunol.* 99(3): 402-409, 1997.

Cheng, et al., "House Dust Mite-Induced Sensitivity in Mice", *Journal of Allergy and Clinical Immunology*, 101(1): 51-59, 1998.

Cheng, et al., "House-Dust Mite (HDM) Induced Hypersensitivity in Mice", *Faseb Journal*, 5(4): 801, 1995.

Cheng, et al., "House-Dust Mite (HDM) Induced Hypersensitivity in Mice", *Journal of Allergy and Clinical Immunology*, 95(1): 380,1995.

Christie, et al., "N-Terminal Amino Acid Sequence Identity Between a Major Allergen of *Asacris lumbricoides* and *Ascaris suum*, and MHC-Restricted IgE Responses to it", *Immunology*, 69:596-602, 1990.

Chua, et al., "Sequence Analysis of cDNA Coding for A Major House Dust Mite Allergen" *J. Exp. Med.* 167:175-182, 1988.

Chua, et al., "Isolation of cDNA Coding for the Major Mite Allergen Der p II by IgE Plaque Immunoassay", *Int. Arch. Allergy Appl. Immunol.* 91:118-123, 1990.

Clarke, et al., "Structure of Mouse Major Urinary Protein Genes: Different Splicing Configurations in the 3'-Non-Coding Region", *EMBO J.*, 3:1045-1052, 1984.

Cockrell, et al., "Monoclonal Antibody Enzyme-Linked Immunosorbent Assay (ELISA) for Ara H 1. A Major Peanut Allergen," *J Aller. Clin. Immunol.*, 89:Abstract 613, 1992.

Colman, "Production of Proteins in the Milk of Transgenic Livestock: Problems, Solutions, and successes," *Am J. Clin. Nutr.* 63(4): 639S-6455S, 1996.

Coman, A. "Production of Therapeutic Proteins in the Milk of Transgenic Livestock" *Biochem. Soc. Symp.* 63: 141-147, 1998.

Cooke & Sampson, "Allergenic Properties of Ovomucoid in Man," *J. Immunol.* 159(4): 2026-32, 1997.

Corbi, et al., "Identification of IgE Binding Polypeptides Cross-Reactive with the *Parietaria judaica* Main Allergenic Polypeptide", *Mol Immunol.* 23(12): 1357-63, Dec. 1986.

Counsell, et al., "Definition of the Human T-Cell Epitopes of Fel D 1, the Major Allergen of the Domestic Cat", *J Allergy Clin Immunol.* 98(5 Pt 1): 884-94, Nov. 1996.

Crameri, et al., "Epidemiology and Molecular Basis of the Involvement of *Aspergillus fumigatus* in Allergic Diseases", *Contrib Microbiol*. Basel. Karger, 2: 44-56.

Czisch, et al., "Conformations of Peptide Fragments Comprising the Complete Sequence of Component III of Chi t I and Their Relationship to T-Cell Stimulation", *Biochemistry* 33(32): 9420-7, Aug. 1994.

Czuppon, et al., "Allergens, IgE, Mediators, Inflammatory Mechanisms", The Rubber Elongation Factor of Rubber Trees (*Hevea brasiliensis*) is the Major Allergen in Latex, *J. Allergy Clin Immunol.*, 92:690-697, 1993.

Daul, et al., "Identification of the Major Brown Shrimp (*Penaeus aztecus*) Allergen as the Muscle Protein Tropomyosin", *Int Arch Allergy Immunol.* 105: 49-55, 1994.

Day, "Genetic Modification of Proteins in Food," *Critical Reviews in Food Science and Nutrition*, 36(S): S49-S67, 1996.

De Palma, et al., "Use of Antagonist Peptides to Inhibit in Vitro T Cell Responses to Par j1, The M Allergen of *Parietaria judaica* Pollen", *J. Immunol.* 162(4): 1982-7, Feb. 15, 1999.

De Jong, et al., "Food Allergen (Peanut)-Specific TH2 Clones Generated from the Peripheral Blood of a Patient with Peanut Allergy," *J Allergy Clin Immunol.* 98(1): 73-81, 1996.

Demerec, et al., "A Proposal for a Uniform Nomenclature in Bacterial Genetics", *Genetics*, 54: 61-75, 1966.

de Groot, "Affinity Purification of a Major and a Minor Allergen from Dog Extract: Serologic Activity of Affinity-Purified Can fI and of Can fI-Depleted Extract" *J Allergy Clin. Immunol.*, 87:1056-1065, 1991.

Demoly, et al., "Anti-IgE Therapy for Asthma," *American J. Resp. Crit Care Med.* 155: 1825-1827, 1997.

Derossi, et al., "Cell Internalization of the Third Helix of the Antennapedia Homeodomain is Receptor-Independent", *The Journal of Biological Chemistry*, 271(30): 18188-18193, 1996.

Deuell, et al., "Trichophyton Tonsurans Allergen I, Characterization of a Protein That Causes Immediate But Not Delayed Hypersensitivity" *J. Immunol.*, 147:96-101, 1991.

Dilworth, et al., "Sequence Analysis of cDNA Coding for a Major House Dust Mite Allergen, Der f I" *Clin. Exp. Allergy*, 21:25-32, 1991.

Directions for Use, Pharmacia Diagnostics AB, Uppsala, Sweden 1985 (Revised 1988).

Dolecek, et al., "Molecular Characterization of Phl p II, a Major Timothy Grass (*Phleum pratense*) Pollen Allergen", *FEBS Letter.*, 335:299-304, 1993.

Ebner, et al., "Multiple T Cell Specificities for Bet v I, the Major Birch Pollen Allergen, with Single Individuals. Studies using Specific T Cell Clones and Overlapping Pepti", *Eur J Immunol.* 23(7): 1523-7, Jul. 1993.

Eichler & Houghten, "Generation and Utilization of Synthetic Combinatorial Libraries," *Mol. Med. Today*, 1(4): 174-80, 1995.

Eigenmann, et al., "Identification of Unique Peanut and Soy Allergens in Sera Adsorbed with Cross-Reacting Antibodies", *J. Allergy Clin Immunol*, 98(5 pt 1):969-78, Nov. 1996.

Ekramoddoullah, "Allergenic Cross Reactivity of Cytochrome c From Kentucky Bluegrass and Perennial Ryegrass Pollens".,*Moll Immunol*. 19: 1527-1537, 1982.

Elfman, et al., "IgE Binding Capacity of Synthetic and Recombinant Peptides of the Major Stor Mite (*Lepidohlyphus destructor*) Allergen, Lep d 2", *Int Arch Allergy Immunol*. 117(3): 167-73, Nov. 1998.

Elsayed, et al., "A Synthetic Hexadecapeptide Derived from Allergen M Imposing Allergenic Antigenic Reactivity", 12(2): 171-5, 1980.

Elsayed, et al., "Allergenic Synthetic Peptide Corresponding to the Second Calcium-Binding of Cod Allergen M", *Scand J Immunol*. 14(2): 207-11, Aug. 1981.

Elsayed, et al., "Antigenic and Allergenic Determinants of Ovalbumin. I. Peptide Mapping, Cleavage at the Methionyl Peptide Bonds and Enzymic Hydrolysis of Native A Carboxymethyl OA", *Int Arch Allergy Appl Immunol*. 79(1): 101-7, 1986.

Elsayed, et al., "Synthetic Allergenic Epitopes from the Amino-Terminal Regions of the Major Allergens of Hazel and Birch Pollen", *Int Arch Allergy Appl Immunol*. 89: 410-415, 1989.

Elsayed, et al., "Tryptic Cleavage of a Homogenous Cod Fish Allergen and Isolation of Two Ac Polypeptide Fragments" *Immunochemistry*, 9(6): 647-61, Jun. 1972.

Elsayed, et al., "The Primary Structure of Fragment TM2 of Allergen M from Cod", *Scand J. Immunol.*, 3: 683-686, 1974.

Elsayed, et al., "Cod Fish Allergen Structure", *Immunochemistry*, 9:647-661, 1972.

Enomoto, et al., "Antibodies Raised Against Peptide Fragments of Bovine Alpha s1-Casein Cross-with the Intact Protein Only When the Peptides Contain Both B and T Cell Determinants", *Mol Immunol*. 27(6): 581-6, Jun. 1990.

Epton, et al., "High-Molecular-Weight Allergens of the House Dust Mite: An Apolipophorin-Li cDNA has Sequence Identity with the Major M-177 Allergen and the IgE-Bin Peptide Fragments Mag1 and Mag3", *Int Arch Allergy Immunol*. 120(3): 185-91, Nov. 1999.

Esch, et al., "Isolation and Characterization of A Major Cross-Reactive Grass Group I Allergenic Determinant", *Mol. Immunol*. 26:557-561.

Espanion, "Methods of Production and Perspectives for Use of Transgenic Domestic Animals," *DTW Dtsch Tierarzti Wochenschr*. 103(8-9): 320-8, 1996.

Ezhevsky, et al., "Hypo-Phosphorylation of the Retinoblastoma Protein (pRb) by Cyclin: D:Cdk4/6 Complexes Results in Active pRb", *Proc. Natl. Acad. Sci. USA*, 94:10699-10704, 1997.

Fahhoum, et al., "Immunologic Variables in a Murine Model of House Dust Mite Sensitivity", *Journal of Allergy and Clinical Immunology*, 99(1): 676, 1997.

Fahhoum, et al., "Tolerization of House Dust Mite Sensitive Mice Using a Major HDM Peptide", *Journal of Allergy and Clinical Immunology*, 101(1): 252, 1998.

Fahy, et al., "The Effect of an Anti-IgE Monoclonal Antibody on the Early-and Late-Phase Responses to Allergen Inhalation in Asthmatic Subjects," *American J Respir Crit Care Med*, 155: 1828-1834, 1997.

Fang, et al., "cDNA Cloning and Primary Structure of a White-Face Hornet Venom Allergen, Antigen 5", *Natl. Acad. Sci.*, USA, 85:895-899, 1988.

Fasler, et al., "Antagonistic Peptides Specifically Inhibit Proliferation, Cytokine Production, CD40L Expression, and Help for IgE Synthesis by Der p 1-Specific Human T-Cell Clones", *J Allergy Clin Immunol*. 101(4 Pt 1): 521-30, Apr. 1998.

Fasler, et al., "Peptide-Induced Anergy in Allergen-Specific Human Th2 Cells Results in Lack Cytokine Production and B Cell Help for IgE Synthesis. Reversal IL-2, not IL-4 or IL-13", *J Immunol*. 155(9): 4199-206, Nov. 1, 1995.

Ferreira, et al., "Modulation of IgE reactivity of allergens by Site-Directed Mutagenesis: Potential Use of Hypoallergenic Variants for Immunotherapy", *FASEB J*, 12: 231-242 (1998).

Fields, et al., "Solid Phase Peptide Synthesis Utilizing 9-Fluorenylmethoxycarbonyl Amino Acids," *Int J Pept Protein Res*. 35(3): 161-214, 1990.

Fischer, et al., "Characterization of PhI p 4, a Major Timothy Grass (*Phleum pratense*) Pollen Allergen" *J. Allergy Clin Immunol*. 98: 189-198, 1996.

Fitzsimmons, et al., "Immunotherapy-Definition and Mechanism," *Allergy Proc.*, 11: 156 (1990).

Fuchs, et al., "Ingredients for Fat Replacement," *Food Tech*. 51: 82-87, 1997.

Fung-Leung, et al., Transgenic Mice Expressing the Human High-Affinity Immonoglobulin (Ig) E Receptor Alpha Chain Respond to Human IgE in Mast Cell Degranualtion and in Allergic Reactions, *J. Exp. Med*. 183: 49-56 (1996).

Garcia, et al., "Nonspecific Changes in Immunotherapy with House dut extract", *J. Invest Alergol. Clin Immunol*. 5 18-24 (1995).

Geluk, et al., "HLA-DR3 Molecules can Bind Peptides Carrying Two Alternative Specific Submotifs", *J Immunol*. 152(12): 5742-8, Jun. 15, 1994.

Ghosh, et al., "Cloning and Expression of Immunologically Active Recombinant Amb a V Allergen of Short Ragweed Pollen", *J. Immunol*., 150: 5391-5399, 1993.

Gjesing, et al., "Immunochemistry of Food Antigens", *Ann. Allergy*, 53:602-608, 1984.

Gibbs, et al., "Evolution of Legume See Storage Proteins—a Domain Common to Legumins and Vicilins is Duplicated in Vicilins," *Mol. Biol. Evol.*, 6: 614-623 (1989).

Gieni, et al., Allergen-Specific Modulation of Cytokins Synthesis Patterns and IgE Respenses in Vivo with Chemically Modified Allergen, *The Journal of Immunol.*, 150: 302-310 (1993).

Gius, et al., "Transduced p16$^{INK4a}$ Peptides Inhibit Hypophosphorylation of the Retinoblastoma Protein and Cell Cycle Progression Prior to Activation of Cdk2 Complexes in Late $G_1^1$" *Cancer Research*, 59:2577-2580, 1999.

Gmachl, et al., "Bee Venom Hyaluronidase is Homologous to a Membrane Protein of Mammalian Sperm", *Proc. Natl. Acad. Sci. USA.*, 90:3569-3573, 1993.

Gonzalez, et al., "Soybean Hydrophobic Protein and Soybean Hull Allergy" *Lancet*, 346:48-49, 1995.

Goodfriend, et al., "New Ragweed Pollen Allergens", *Fed. Proc*. 38: 1415.

Goodfriend, et al., "Ra5G, A Homologue of Ras5 In Giant Ragweed Pollen: Isolation, HLA-DR-Associated Activity and Amino Acid Sequence", *Mol. Immunol*. 22: 899-906, 1985.

Gordon, Future Immunotherapy: What Lies Ahead?, *Otolaryngol Head Neck Surg.*, 113: 603-605 (1995).

Greene, "Characterizaton of Allergens of the Cat Flea, Cetnocephalides Felis: Detection and Frequency of IgE Antibodies in Canine Sera," *Parasit Immunology*, 15: 69-74, 1993.

Greene, et al., IgE and IgG Binding of Peptides Expressed from Fragments of cDNA Encoding the Major House Dust Mite Allergen Der p I *J Immunol*. 147(11): 3768-73, Dec. 1, 1997.

Griffith, et al., "cDNA Cloning of Cry j r, The Major Allergen of *Cryptomeria japonica* (Japanese Cedar)" *J. Allergy. Clin. Immunol*. 91:339, 1993.

Griffith, et al., Sequence Poymorphisms of Amb a I and Amb a II, The Major Allergens in *Ambrosia artemisiifolia* (Short Ragweed). *Int. Arch. Allergy Appl. Immunol*. 96: 296-304, 1991.

Griffith, et al., "Expression and Genomic Structure of the Genes Encoding FdI, the Major Allergen from the Domestic Cat", *Gene*, 113: 263-268, 1992.

Griffith, et al., "Cloning and Sequencing of Lol pI, the Major Allergenic Protein of Rye-Grass Pollen", *FEBS Letters*, 279:210-215, 1991.

Gross, et al., "Isolation and Partial Characterization of the Allergen in Mountain Cedar Pollen", *Scand J. Immunol.*, 8:437-441, 1978.

Guerin-Marchand, et al., "Cloning, Sequencing and Immunological Characterization of Dac g 3, A Major Allergen From *Dactylis glomerata* Pollen", *Mol. Immunol*. 33:797-806, 1996.

Habermann, E., "Bee and Wasp Venoms", *Science*, 177:314-322, 1972.

Halliwell, "Aspects of the Immunopathogenisis of Flea Allergy Dermatitis in Dogs," *Veterinary Immunology and Immunopathology*, 17: 483-494, 1987.

Halliwell, IgE and IgG Antibodies to Flea Antigen in Differing Dog Populations, *Veterinary Immunology and Immunopathology*, 8: 215-223, 1985.

Halmepuro, et al., "Crawfish and Lobster Allergens: Identification and Structural Similarities with Other Crustacea", *Int. Arch Allergy Appl. Immun*. 84: 165-72, 1987.

Haselden, et al., "Immunoglobulin E-independent Major Histocompatibility Complex-restricted T Cell Peptide Epitope-induced Late Asthmatic Reactions" *J Exp Med*. 189(12): 1885-94, Jun. 21, 1999.

Hawrylowicz, et al., "T-Cell Receptor Peptides that Inhibit the T-Cell Response to Allergen Induce Transforming Growth Factor-Beta 1 Production", *J Allergy Clin Immunol*. 97(2): 707-9, Feb. 1996.

Hefle, et al., "Isolation of Peanut Allergens Using Monoclonal Antibodies," *J. Allergy and Clinical Immunology*, 87: Abstract, 209, 1991.

Heiner, et al., "RAST Analyses of Peanut Allergens," *J. Allergy Clin. Immunol.*, 55: 82, 1975.

Helm, et al., "A Major Allergen Involved in IgE Mediated Cockroach Hypersensitivity is a 90 kD Protein with Multiple IgE Binding Domains", *Adv Exp Med Biol*. 409: 267-8, 1996.

Helm, et al., "Cellular and Molecular Characterization of a Major Soybeam Allergen", *Int. Arch Allergy Immunol*. 117(1), 29-37, Sep. 1998.

Helm, et al., "Isolation and Characterization of a Clone Encoding a Major Allergen (Bla g Bd90K) Involved in IgE-Mediated Cockroach Hypersensitivity", *J Allergy Clin Immunol*. 98(1): 172-80, Jul. 1996.

Helm, et al., "Isolation and Characterization of Clones Encoding Cockroach Allergens", *Int. Arch Allergy Immunol*. 107(1-3): 462-3, May-Jun. 1995.

Helm, et al., "Mutational Analysis of the IgE-binding Epitopes of P34/Gly m Bd 30K", *J Allergy Clin. Immunol*. 105(2): 378-84, Jan. 2000.

Helm, et al., "Cloning of a Portion of Ara H 3: A Peanut Allergen", Abstract.

Herian, et al., "Identification of Soybean Allergens by Immunoblotting with Sera from Soy-Allergic Adults," *Int. Arch. Allergy Appl. Immunol*. 92: 193-198, 1990.

Hetzel, et al., "Peptide-Mediated Immunoregulation", *Int Arch Allergy Immunol*. 107:(1-3): 275-7, May-Jun. 1995.

Higgins, et al., "Overlapping T-Cell Eptiopes in the Group I Allergen of Dermatophagoides sp Restricted by HLA-DP and HLA-DR Class II Molecules", *J Allergy Clin Immunol*. 93(5): 891-9, May 1994.

Higgins, et al., "Peptide-Induced Nonresponsiveness of HLA-DP Restricted Human T Cells rea with Dermatophagoides spp", *J Allergy Clin Immunol*. 90(5): 749-56, Nov. 1992.

Hirahara, et al., "Oral Administration of A Dominant T-Cell Determinant Peptide Inhibits Allergen-Specific TH1 and TH2 Cell Responses in Cry J 2-Primed Mice", *J Allergy Clin Immunol.* 102(6 Pt 1): 961-7, Dec. 1998.

Ho, et al., "Comparison of the Immunogenicity of Wasp Venom Peptides With or Without Carbohydrate Moieties", *Toxicon.* 36(1): 217-21, Jan. 1998.

Hoffman, et al., "Allergens in Hymenoptera Venom XXV: The Amino Acid Sequences of Antigen 5 Molecules and the Structural Basis of Antigenic Cross-Reactivity", *J. Allergy Clin. Immunol.*, 92:707-716, 1993.

Hoffman, et al., "Allergens in Hymenoptera Venom XXIV: The Amino Acid Sequences of Imported Fire Ant Venom Allergens Sol i II, Sol i III, and Sol i IV" *J. Allergy Clin. Immunol.*, 91:71-78, 1993.

Hoffman, D.R., "Immunochemical Identification of the Allergens in Egg White", *J. Allergy Clin. Immunol.* 71:481-486, 1983.

Hong, et al., "Pepsin-Digested Peanut Contains T-Cell Epitopes But no IgE Epitopes", J. Allergy Clin. Immunol. 104: 473-7, 1999.

Horner, et al., "Identification of the Allergen Psi c 2 from the Basidiomycete *Psilocybe cubensis* as a Fungal Cyclophilin", *Int. Arch. Allergy Immunol.*, 107:298-300, 1995.

Hoyne, et al., "Inhibition of T-Cell Responses by Feeding Peptides Containing Major and Cryp Epitopes: Studies with the Der p I Allergen", *Immunology* 83(2): 190-5, Oct. 1994.

Hoyne, et al., "Peptide Modulation of Allergen-Specific Immune Responses", *Curr Opin Immunol.* 7(6): 757-61, Dec. 1995.

Hsu, et al., "Inhibition of Specific IgE Response in Vivo by Allergen-Gene Transfer," *Int. Immunol.* 8:1405-1411, 1996.

Jacobson, et al., "Characterization of Bumblebee Venom Allergens" *J. Allergy Clin. Immunol.* 91:187, 1993.

Jacobson, et al., "The Cross-Reactivity Between Bee and Vespid Hyaluronidases has a Structural Basis" *J. Allergy Clin. Immunol.*, 89:292, 1992.

James, et al., "Wheat α-Amylase Inhibitor: A Second Route of Allergic Sensitization", *J Allergy Clin Immunol.* 99(2): Feb. 1997.

James, et al., "Serum IgE Antibodies From Wheat-Allergic Patients Bind A 50 kD Wheat Protein", Abstract., J. Allergy Clin Immunol, 95:332, 1995.

Jameson, et al., "The Antigenic Index: A Novel Algorithm for Predicting Antigenic Determinants," *Comput. Appl. BiosciI*, 4: 181-186 (1988).

Jansen, et al., "Prevalance of Food Allergy and Intolerance in the Adult Dutch Population," *J. Allergy Clin. Immunol.*, 93: 446-456 (1994).

Jarman, et al., "Inhibition of Human T-Cell Responses to House Dust Mite Allergens by a T-Cell Receptor Peptide", *J Allergy Clin Immunol.* 94(5): 844-52, Nov. 1994.

Jeannin, et al., "Immunogenicity and Antigenicity of Synthetic Peptides Derived from the Mite Allergen Der p I", *Mol Immunol.* 30(16): 1511-8, Nov. 1993.

Jeannin, et al., "Specific Histamine Release Capacity of Peptides Selected from the Modelized Der p I Protein, a Major Allergen of *Dermatophagoides pteronyssinus*", *Mol Immunol.* 29(6): 739-49, Jun. 1992.

Jensen-Jarolim, et al., "Allergen Mimotopes in Food Enhance Type I Allergic Reactions in Mice", *The FASEB Journal*, 13: 1586-92, Sep. 1999.

Jensen-Jarolim, et al., "Nonapeptides Selected by Phage Display Mimic The Binding Sites of Monoclonal Antibodies BIP1 and BIP4 on Bet v 1, The Major Birch Pollen Allergen", *Int Arch Allergy Immunol.* 118(2-4): 224-5, Feb.-Apr. 1999.

Jensen-Jarolim, et al., "Peptide Mimotopes Displayed by Phage Inhibit Antibody Binding to Bet v 1, the Major Birch Pollen Allergen, and Induce Specific IgG Response in Mice", FASEB J. 12(15): 1635-42, Dec. 1998.

Jimenez, et al., Sensitization to Sunflower Pollen: Only an Occupational Allergy? *Int. Arch Allergy Immunol.* 105:297-307, 1994.

Jusko, "Cortiocosteroid Pharmacodynamics: Models for Broad Array of Receptor-mediate Pharmacologic Effects," *Clin. Pharmacol*, 30: 303-10, 1990.

Kaminogawa, "Food Allergy, Oral Tolerance and Immunomodulation—Their Molecular and Cellular Mechanisms," *Biosci. Biotech, Biochem.* 60: 1749-1756, 1996.

Kammerer, et al/. "Modulation of T-Cell Response to Phospholipase A2 and Phospholipase A2-Derived Peptides by Conventional Bee Venom Immunotherapy", *J Allergy Clin Immunol.* 100(1): 96-103, Jul. 1997.

Kapitany, et al., "A High Resolution PAS Stain for Polyacrylamide Gel Electrophoresis," *Anal. Biochem.*, 56: 361-9, 1973.

Keating, et al. "Immunoassay of Peanut Allergens in Food-Processing Materials and Finished Foods," *J. Allergy Clin. Immunol.* 86: 41-44, 1990.

Kettner, et al., "IgE and T-Cell Responses to High-Molecular Weight Allergens from Bee Venom", *Clin. Exp. Allergy*, 29(3): 394-401, Mar. 1999.

KielisZewski, et al. "Potato Lectin: A Modular Protein Sharing Sequence Similarities with the Extensin Family, the Hevein Lectin Family, and Snake Venom Disintegrins (Platelet Aggregation Inhbitiors)," *Plant J.* 5(6): 849-861, 1994.

Kim, et al., "Suppressive Vaccination at Allergen-Induced Immunoglobulin E Production by the Naked DNA Vaccine", *Journal of Investigative Medicine*, 46(3): A243, 1998.

Kim, et al., "Suppressive Vaccination of Allergen-Induced Immunoglobulin E Production by the Naked DNA Vaccine" *Faseb Journal*, 12(5): 6148, 1998.

King, et al., "Isolation and Characterization of Allergen from Ragweed Pollen" *Biochemistry*, 3: 458-468, 1964.

King, et al., "The Isolation and Characterization of a Novel Collagenolytic Serine Protease Allergen (Der p 9) from the Dust Mite *Dermatophagoides pteronyssinus*", *J. Allergy Clin Immunol.*, 98:739-747, 1996.

King, et al., "Structural Studies of a Hornet Venom Allergen Antigen 5, Dol m V and its Sequence Similarity with Other Proteins" *Prot. Seq. Data Anal.*, 3:263-266, 1990.

King, et al., "Yellow Jacket Venom Allergens, Hyaluronidase and Phospholipase: Sequence Similarity and Antigenic Cross-Reactivity with Their Hornet and Wasp Homologs and Possible Implications for Clinical Allergy" *Allergy Clin. Immunol.*, 98:588-600, 1996.

Klapper, et al., "Amino Acid Sequence of Ragweed Allergen Ra3", *Biochemistry*, 19: 5729-5733, 1980.

Klysner, et al., "Group V Allergens in Grass Pollens: IV. Similarities in Amino Acid Compositions and $NH_2$ Terminal Sequences of the Group V Allergens from *Lolium perenne, Poa pratensis* and *Dactylis glomerata*", *Clin. Exp. Allergy*, 22:491-497, 1992.

Kohler, et al., "Continuous Cultures of Fused Cells Secreting Antibody of Predefined Specificity," *Nature*, 256: 495-497, 1975.

Kricek, et al., "IgE-Related Peptide Mimotopes, Basic Structures for Anti-Allergy Vaccine Development", *Int Arch Allergy Immunol.* 118 (2-4): 222-3, Feb.-Apr. 1999.

Krieg, et al., "CpG Motifs in Bacterial DNA Trigger Direct B-Cell Activation," *Nature*, 374(6522): 546-9, 1995.

Kuchler, et al., "Analysis of the cDNA for Phospholipase $A_2$ from Honeybee Venom Glands; The Deduced Amino Acid Sequence Reveals Homology to the Corresponding Vertebrate Enzymes", *Eur. J. Biochem.*, 184:249-254, 1989.

Kumar, et al., "Isolation and Characterization of a Recombinant Heat Shock Protein of *Aspergillus fumigatus*", *J. Allergy Clin. Immunol.*, 91:1024-1030, 1993.

Kurup, et al., "Immunodominant Peptide Epitopes of Allergen, Asp F 1 from the Fungus *Aspergillus fumigatus*", *Peptides*, 19(9): 1469-77, 1998.

Kwon, et al., "Immunoprotective Effect of Vaccination with DNA Encoding T Cell Epitopes on the Der p Induced IgE Production" *Journal of Allergy and Clinical Immunology*, 103: 418, 1999.

Kwon, et al., "The Effect of the Intradermal Vaccination with DNA Encoding the T-Cell Receptor on the Induction of Experimental Autoimmune Encephalomyelitis in Mice", *Journal of Allergy and Clinical Immunology*, 103: 76, 1999.

Lacroix, et al., "Attenuation of Allergen-Evoked Nasal Responses by Local Pretreatment with Exogenous Neuropeptide Y in Atopic Patients", *J Allergy Clin Immunol.* 98(3):611-6, Sep. 1996.

Laemmli, "Cleavage of Structural Proteins During the Assembly of the Head of Bacteriophage T4", *Nature*, 227: 680-5, 1970.

Lake, et al., "House Dust Mite-Derived Amylase: Allergenicity and Physicochemical Characterization", *J. Allergy Clin. Immunol.* 87:1035-1042, 1991.

Langeland, T., "A Clinical and Immunological Study of Allergy to Hen's Egg White", *Allergy*, 38:493-500, 1983.
Laperche, et al., "Tissue-Specific Control of $\alpha_{2u}$ Globulin Gene Expression: Constitutive Synthesis in the Submaxillary Gland" *Cell*, 32:453-460, 1983.
Larsen, et al., "PCR Based Cloning and Sequencing of Isogenes Encoding the Tree Pollen Major Allergen Car b I from *Carpinus betulus*, Hornbeam", *Mol. Immunol.* 29: 703-711, 1992.
Lehrer, et al., "Reactivity of IgE Antibodies with Crustacea and Oyster Allergens: Evidence for Common Antigenic Structures", *J Allergy Clin. Immunol.* 80(2): 133-39, Aug. 1987.
Lemanske & Taylor, "Standardized Extracts, Foods," *Clin. Rev. Allergy*, 5: 23-26, 1987.
Leung, et al., "Identification and Molecular Characterization of *Charybdis feriatus* Tropomyosin, The Major Crab Allergen", *J. Allergy Clin Immunol.* 847-852, Nov. 1998.
Leung, et al., "IgE Reactivity Against a Cross-Reactive Allergen in Crustacea and Mollusca: Evidence for Tropomyosin as the Common Allergen", *J. Allergy Clin Immunol.* 98(5), 954-961, Nov. 1996.
Liebers, et al., "Epitope Mapping with Peptides of Chi t I Component III and Immunomodula of the Chi t Immune Response", *J Allergy Clin Immunol.* 92(2): 334-9, Aug. 1993.
Lind, et al., "The Binding of Mouse Hybridoma and Human IgE Antibodies to the Major Fecal Allergen, Der p I, of *Dermatophagoides pteronyssinus*, Relative Binding Site Location and Species Specificity Studied by Solid-Phase Inhibition Assays with Radiolabeled Antigen", *J. Immunol.*, 140:4256-4262, 1988.
Ling, et al., "Construction and Characterization of Human IgE Fab Fragments Specific to Peanut Allergens", Abstract., J. Allergy Clin. Immunol. 107 :s290-s291, 2001.
Litwin, et al., "Regulation of the Human Immune Response to Ragweed Pollen by Immunotherapy. A Controlled Trial Comparing the Effect of Immunosuppressive Peptic Fragments of Short Ragweed with Standard Treatment", *Clin Exp. Allergy*. 21(4): 457-65, Jul. 1991.
Litwin, et al., "Regulation of the Immune Response to Allergens by Immunosuppressive Allergenic Fragments, Peptic Framents of Honey Bee Venom Phospholipase", *Int Arch Allergy Appl Immunol.* 87(4): 361-6, 1988.
Lopata, et al., "Characteristics of Hypersensitivity Reactions and Identification of a Unique 49 kd IgE-Binding Protein (Hal-m-1) in Abalone (*Haliotis midae*)" *J. Allergy Clin. Immunol.* , 1997.
Lowenstein, H., "Timothy Pollen Allergens" *Allergy*: 35: 188-191, 1980.
Lu, et al., "Sequence Analysis and Antigenic Cross-Reactivity of a Venom Allergen, Antigen 5, From Hornets, Wasps, and Yellow Jackets" *The Journal of Immunology*, 150:2823-2830, 1993.
Maguire, et al., "The Safety and Efficacy of Allervax Cat in Cat Allergic Patients" *Clin Immunol.* 93(3): 222-31, Dec. 1999.
Marcotte, et al., "Effects of Peptide Therapy on Ex Vivo T-Cell Responses", *J Allergy Clin Immunol.* 101(4 Pt 1): 506-13, Apr. 1998.
Marsh, et al., "Allergen Nomenclature", *Bull WHO* 64: 767-770, 1986.
Mathison, et al., "A Peptide from the Submandibular Glands Modulates Inflammatory Responses", *Int Arch Allergy Immunol.* 113 (1-3): 337-8, May-Jul. 1997.
Matthiesen, et al., "Group V Allergens in Grass Pollens. I. Purification and Characterization of the Group V Allergen from *Phleum pratense* Pollen, Phl p V" *Clin. Exp. Allergy*, 21:297-307, 1991.
Matsuoka, et al., "Altered TCR Ligands Affect Antigen-Presenting Cell Responses: Up-Regulation IL-12 by an Analogue Peptide", *J Immunol.* 157(11): 4837-43, Dec. 1996.
McKeon, "IgG and IgE Antibodies Against Antigens of the Cat Flea, *Ctenocephalides felis* Felis in Sera of Allergic and Non-Allergic Dogs," *Int. J. Parasitology*, 24(2): 259-263, 1994.
Mena, et al., "A Major Barley Allergen Associated with Baker's Asthma Disease is a Glycosylated Monomeric Inhibitor o f Insect α-Amylase: cDNA Cloning and Chromosomal Location of the Gene", *Plant Molec. Biol.* 20:451-458, 1992.
Menedez-Arias, et al., "Primary Structure of the Major Allergen of Yellow Mustard (*Sinapis alba* L. ) Seed, Sin α I" *Eur. J. Biochem.*, 177:159-166, 1988.
Metcalfe, "Food Allergens," *Clin Rev Allergy*, 3:331-49, 1985.

Metzler, et al., "Determination of the Three-Dimensional Solution Structure of Ragweed Allergen Amb t V by Nuclear Magnetic Resonance Spectroscopy". *Biochemistry*, 31: 5117-5127, 1992.
Metzler, et al., "Proton Resonance Assignments and Three-Dimensional Solution Structure of the Ragweed Allergen Amb a V by Nuclear Magnetic Resonance Spectroscopy" *Biochemistry*, 31: 8697-8705, 1992.
Miller, et al., "Allergy to Bovine Beta-Lactoglobulin: Specificity of Immunoglobulin E Gener in the Brown Norway Rat to Tryptic and Synthetic Peptides", *Clin. Exp. Allergy*, 29(12): 1696-704, Dec. 1999.
Miyazawa, et al., "Identification of the First Major Allergen of a Squid (*Todarodes pacificus*)", *J. Allergy Clin. Immunol.*, 98:948-953, 1996.
Mohapatra, SS, "Modulation of Allergen-Specific Antibody Responses by T-Cell-Based Peptide Vaccine(s). Principles and Potential", *Clin Rev Allergy*. 12(1): 3-22, Spring, 1994.
Moneret-Vautrin, "Modifications of Allergenicity Linked to Food Technologies," *Allerg Immunol*, 30(1): 9-13, 1998.
Monsalve, et al., "Characterization of a New Oriental-Mustard (*Brassica juncea*) Allergen, Bra j IE: Detection of an Allergenic Epitope" *Biochem. J.*, 293:625-632, 1993.
Morgenstern, et al., "Amino Acid Sequence of Fel d I, the Major Allergen of the Domestic Cat: Protein Sequence Analysis and cDNA Cloning" *Proc. Natl. Acad. Sci. USA*, 88: 9690-9694, 1991.
Muckerheide, et al., "Immunosuppressive Properties of a Peptic Fragment of BSA", The Journal of Immunology, 119(4): 1340-45, Oct. 1977.
Muckerheide, et al., "Kinetics of Immunosuppression Induced by Peptic Fragments of Bovine Serum Albumin", *Cellular Immunology*, 50, 340-47, 1980.
Muller, et al., "Successful Immunotherapy with T-Cell Epitope Peptides of Bee Venom Phospholipase A2 Induces Specific T-Cell Anergy in Patients Allergic to Bee Venom" *J Allergy Clin Immunol.* 101(6 Pt 1): 747-54, Jun. 1998.
Nagahara, et al., "Transduction of Full-Length TAT Fusion Proteins into Mammalian Cells: TAT-p27$^{Kip1}$ Induces Cell Migration", *Nature Medicine*, 4(12): 1449-1452, 1998.
Nair, Smita et al., Soluble Proteins Delivered to Dendritic Cells Via pH-sensitive Liposomes Induce Primary Cytotoxic T Lymphocyte Responses In Vitro, *J. Exp. Med.*, 175 Feb. 1992 609-612.
Nelson, et al., "Treatment of Anaphylactic Sensivitity to Peanuts by Immunotherapy with Injections of Aqueous Peanut Extract," *J. Allergy Clin. Immunol.* 99: 744-751, 1997.
Nicodemus, et al., "Integrated Clinical Experience with Tolerogenic Peptides", *Int Arch Allergy Immunol.* 113:(1-3): 326-8, May-Jul. 1997.
Nishiyama, et al., "Determination of Three Disulfide Bonds in a Major House Dust Mite Allergen, Der f II", *Int. Arch. Allergy Immunol.*, 101:159-166, 1993.
Noon, "Prophylactic Inoculatio Against Hay Fever," *Lancet*, 1: 1572-73, 1911.
Nordlee, et al., "Allergenicity of Various Peanut Products as Determined by RAST Inhibition," *J. Allergy Clin. Immunol.* 68: 376-82, 1981.
Norman, et al., "Clinical and Immunologic Effects of Component Peptides in Allervax Cat", *Int Arch Allergy Immunol.* 113(1-3): 224-6, May-Jul. 1997.
Norman, et al., "Multicenter Study of Several Doses of ALLERVAX® Cat Peptides in the Treatment of Cat Allergy," *Journal of Allergy and Clinical Immunology*, 99: S127, 1997.
Norman, et al., "Treatment of Cat Allergy with T-Cell Reactive Peptides" *Am J Respir Crit Care Med*. 154(6 Pt 1): 1623-8, Dec. 1996.
Obispo, et al., "The Main Allergen of *Olea europaea* (Ole e I) is Also Present in other Species of the Oleaceae Family", *Clin. Exp. Allergy*, 23:311-316, 1993.
O'Brien, et al., "An Immunogenetic Analysis of T-Cell Reactive Regions on the Major Allergen from the House Dust Mite, Der p I, with Recombinant Truncated Fragments", *J Allergy Clin Immunol.* 93(3): 628-34, Mar. 1994.
O'Farrell, "High Resolution Two-Dimensional Electrophoresis of Proteins," *J. Biol. Chem.* 250: 4007-21, 1975.

O'Hehir, et al., "House Dust Mite Allergy: From T-Cell Epitopes to Immunotherapy", *Eur J Clin Invest*. 23(12): 763-72, Dec. 1993.

O'Hehir, et al., An In Vitro Model of Peptide-Mediated Immunomodulation of the Human T c Response to *Dermatophagoides* spp (House Dust Mite) *J Allergy Clin Immunol*. 87(6): 1120-7, Jun. 1991.

Okano, et al., "Population Analysis of Cellular Respones to Synthetic Peptides of Der p II, a Major Allergen Molecule of *Dermatophagoides pteronyssinus*, in Allergic and Nonallergic Subjects", *Allergy*. 49(6): 436-41, Jul. 1994.

O'Neil, et al., "Cloning and Characterization of a Major Allergen of the House Dust Mite, *Dermatophagoides pteronyssinus*, Homologous with Glutathione S-Transferase", *Biochimica et Biophysica Acta*, 1219:521-528, 1994.

Oppenheimer, et al., "Treatment of Peanut Allergy with Rush Immunotherapy", *J Allergy Clin Immunol*. 90: 256-62, 1992.

Park, et al., "Pediatric IgE Anibody binding to the Most Common Seafood Proteins in Korea", *Journal of Allergy and Clinical Immunology*, 101(1): 377, 1998.

Pecquet, et al., "Immunoglobulin E Suppression and Cytokine Modulation in Mice Orally Tolerized to β-Lactoglobulin", *Immunology*, 96, 278-85, 1999.

Pene, et al., "Immunotherapy with Fel D 1 Peptides Decreases IL-4 Release by Peripheral Blood T Cells of Patients Allergic to Cats", 102: (4 Pt 1): 571-8, Oct. 1998.

Perez, et al., "cDNA Cloning and Immunological Characterizaton of the Rye Grass Allergen Lol p I" *J. Biol. Chem*. 265:16210-16215, 1990.

Pesce, et al., "Modulation of the Immune Response to Allergens: Phospholipase A Degradation Products Suppress IgG and IgE Response in Mice", *Int Arch Allergy Appl Immunol*, 92, 88-93, 1990.

Phadebas Rast Radioimmunoassay Reagents for 100 or 300 Tubes, Pharmacia Diagnostics, AB, Uppsala Sweden 1985, Revised Jan. 1988.

Pisetsky, "Immune Activation by Bacterial DNA: A New Genetic Code," *Immunity*, 5(4): 303-10, 1996.

Pollart, et al., "Identification, Quantitation, and Purification of Cockroach Allergens using Monoclonal Antibodies," *J. Allergy Clin. Immunol*., 87: 511-521, 1991.

Posch, et al., "Characterization and Identification of Latex Allergens by Two-Dimensional Electrophoresis and Protein Microsequencing," *J. Allergy Clin. Immunol*, 99(3): 385-395, 1997.

Pucheu-Haston, "Allergenic Cross-Reactivities in Flea-Reactive Canine Serum Samples," *AJVR* 57(7): 1000-1005, 1996.

Rabjohn, et al., "Molecular Cloning and Epitope Analysis of the Peanut Allergen Ara h 3", *J. Clin. Invest*. 103(4), 535-42, Feb. 1999.

Rafner, et al., "Cloning of Amb a I (Antigen E), the Major Allergens Family of Short Ragweed Pollen", *J. Biol. Chem*. 266: 1229-1236, 1991.

Raz, et al., "Intradermal Gene Immunization: The Possible role of DNA Uptake in the Induction of Cellular Immunity to Viruses," *Proc Nat Acad Sci USA*, 91:9519-9523, 1994.

Reese, et al., "Characterization of Recombinant Shrimp Allergen Pen a 1 (Tropomyosin)", *Int Arch Allergy Immunol*, 113: 240-242, 1997.

Remy, et al., "Topical Peptides: Percutaneous Absorption of a Vasopressin Derivate, Grass Pollen, and Other Allergens by Iontophoresis in Men", *J Invest Dermatol*. 91(6): 606, Dec. 1988.

Roberts, et al., "Nucleotide Sequence of cDNA Encoding the Group II Allergen of Cocksfoot/Orchard Grass (*Dactylis glomerata*), Dac g II", *Allergy*, 48:615-623, 1993.

Roebber, et al., "Immunochemical and Genetic Studies of Amb t V (Ra5G), an Ra5 Homologue from Giant Ragweed Pollen", *J. Immunol*. 134: 3062-3069, 1985.

Roebber, et al., "Isolation and Characterization of Allergen Amb a VII from Short Ragweed Pollen", *J. Allergy Clin. Immunol*. 87: 324, 1991.

Rogers, et al., "Potential Therapeutic Recombinant Proteins Comprised of Peptides Containing Recombined T Cell Epitopes", *Mol Immunol*. 31(13): 955-66, Sep. 1994.

Rogers, et al., "Complete Sequence of the Allergen Amb a II: Recombinant Expression and Reactivity with T Cells from Ragweed Allergic Patients", *J. Immunol*. 147: 2547-2552, 1991.

Rolfsen, "Detection of Specific IgE Antibodies Towards Cat Flea (*Ctenocephalides Felis Felis*) in Patients with Suspected Cat Allergy," *Allergy*, 42: 177-181 (1987).

Rolland, et al., "Immunotherapy of Allergy: Anergy, Deletion, and Immune-Deviation", Current Opinion in Immunology, 10: 640-45, 1998.

Rooney, et al., "Antiparallel, Intramolecular Triplex DNA Stimulates Homologous Recombinant in Human Cells," *Proc. Natl. Acad. Sci. USA*, 92: 2141-2144, 1995.

Sachs, et al., "Isolation and Partial Characterization of a Major Peanut Allergen," *J. Allergy Clin. Immunol*. 67: 27-34, 1981.

Sakaguchi, et al., "Identification of the Second Major Allergen of Japanese Cedar Pollen", *Allergy*, 45:309-312, 1990.

Sampson & McCaskill, "Food Hypersensitivity in Atopic Determatitis: Evaluation of 113 Patients," *J. Pediatr*. 107: 669-75, 1995.

Sampson, "Peanut Anaphylaxis," *J Allergy Clin Immunol*., 86: 1-3, 1990.

Sampson, "Role of Immediate Food Hypersensitivity in the Pathogenesis of Atopic Dematitis," *J. Allergy Clin. Immunol*. 71: 473-80, 1993.

Sampson, et al., "Fatal and Near-Fatal Anaphylactic Reactions to Food in Children and Adolescents", *The New England Journal of Medicine*, 327(6): 380-84, Aug. 1992.

Sampson, et al., "Food Allergy and the Role of Immunotherapy," *J Allergy Clin. Immun*, 90:151-52, 1992.

Sampson, et al., "Mechanisms of Food Allergy," *Annu. Rev. Nutr*, 16: 161-77, 1996.

Reisman, "Fifteen yeas of hymenoptera Venom Immunotherapy," *J. Allergy Clin Immunol*., 90: 256-62 (1992).

Scheiner, "Recombinant Allergens: Biological, Immunological and Practical Aspects," *Int. Arch. Allergy Immunol*., 98: 93-96 (1992).

Schemmer, "Efficacy of Alum-Precipitated Flea Antigen for Hyposensitization of Flea-Allergic Dogs," *Seminars in Veterinary Medicine and Surgery (Small Animal)*, 2(3): 195-198, 1987.

Schmidt, et al., "cDNA Analysis of the Mite Allergen Lep d 1 Identifies Two Different Isoallergens and Variants", *FEBS Letter*, 370:11-14, 1995.

Schmidt, et al., "The Complete cDNA Sequence and Expression of the First Major Allergenic Protein of *Malassezia furfur*, Mal f 1", *Eur J. Biochem*., 246:181-185, 1997.

Schmidt, et al., "Nucleotide Sequence of cDNA Encoding the Fire Ant Venom Protein Sol i II", *FEBS Letter*, 319:138-140, 1993.

Secrist, et al., "Allergen Immunotherapy Decreases Interleuken 4 Production in CD4 + T Cells From Allergic Individuals," *J. Exp. Med*. 178 2123-2130 (1993).

Sehra, et al., "Role of Liposomes in Selective Proliferation of Splenic Lymphocytes" *Molecular and Cellular Biochemistry*, 183: 133-139, 1998.

Sevier, et al., "Monoclonal Antibodies in Clinical Immunology," *Clin. Chem*. 27(11): 1797-1806, 1981.

Shanti, et al., "Identification of Tropomyosin as the Major Shrimp Allergen and Characterization of its IgE-Binding Epitopes: ," *J. Immunol*, 151: 5354-5363, 1993.

Sharif, et al., "Biodegradable microparticles as a delivery system for the allergens of *Dermatophagoides pteronyssinus* (house dust mite): I. Preparation and characterization of microparticles", *International Journal of Pharmaceutics*, 119 1995) 239-246.

Shen, et al., "Molecular Cloning of a House Dust Mite Allergen with Common Antibody Binding Specificities with Multiple Components in Mite Extracts", *Clin. Exp. Allergy*, 23: 934-940, 1993.

Shen, et al., "Studies on Allergens of *Aspergillus flavus*", *J. Allergy Clin. Immunol*., 103:S157, 199.

Shen, et al., "Allergenic Components in Three Different Species of Penicillium: Crossreactivity Among Major Allergens" *Clin. Exp. Allergy*, 26:444-451, 1996.

Shen, et al., "Molecular Cloning of cDNA Coding for the 68 kDa Allergen of *Penicillium notatum* Using MoAbs", *Clin Exp. Allergy*, 25:350-356, 1995.

Shen, et al., "The 40-Kilodalton Allergen of *Candida albicans* is an Alcohol Dehydrogenase: Molecular Cloning and Immunological Analysis Using Monoclonal Antibodies", *Clin Exp. Allergy*, 21:675-681, 1991.

Shin, et al., "Biochemical and Structural Analysis of the IgE Binding Sites on Ara h1, An Abundant and Highly Allergenic Peanut Protein", *J. Biol. Chem.* 273(22): 13753-9, May 1998.

Sidoli, et al., "Cloning, Expression, and Immunological Characterization of Recombinant Lolium-Perenne Allergen Lol p II", *J. Biol Chem.*, 268:21819-21825, 1993.

Simons, et al., "Fel D 1 Peptides: Effect on Skin Tests and Cytokine Synthesis in Cat-Allergic Human Subjects", Int Immunol. 8(12): 1937-45, Dec. 1996.

Singh, et al., "Isolation of cDNA Encoding a Newly Identified -Major Allergenic P, rotein of Rye-Grass Pollen: Intracellular Targeting to the Amyloplast", *Proc. Natl. Acad. Sci.*, 88:1384-1388, 1991.

Smith, et al., "Cloning and Expression in Yeast *Pichia pastoris* of a Biologically Active Form of Cyn d 1, the Major Allergen of Bermuda Grass Pollen", *J. Allergy Clin. Immunol.* 98:331-343, 1996.

Smith, et al., "Comparative Analysis of the Genes Encoding Group 3 Allergens from *Dermatophagoides pteronyssinus* and *Dermatophagoides farinae*", *Int Arch Allergy Immunol.*, 109:133-140, 1996.

Soldatova, et al., "Sequence Similarity of a Hornet (*D. maculata*) Venom Allergen Phospholipase $A_1$ with Mammalian Lipases", *FEBS Letters*, 320:145-149, 1993.

Sone, et al., "T Cell Epitopes in a Japanese Cedar (*Cryptomeria japonica*) Pollen Allergens: Choice of Major T Cell Epitopes in Cry j 1 and Cry j 2 Toward Design of the Peptide-Immunotherapeutics for the Management of Japanese Cedar Pollinosis", *J. Immunol.* 161(1):448-57, Jul. 1, 1998.

Sparholt, et al., The Allergen Specific B-Cell Response During Immunotherapy. *Clinical and Experimental Allergy*, 22: 648-653 (1992).

Stadler, et al., "Mimotope and Anti-Idiotypic Vaccines to Induce an Anti-IgE Response", *Int Arch Allergy Immunol.* 118(2-4): 119-21, Feb.-Apr. 1999.

Stanley, et al., "Biochemistry of Food Allergens", Clin Rev. Allergy Immunol. 17(3): 279-91, 1999.

Stanley, et al., "Identification and Mutational Analysis of the Immunodominant IgE Binding Epitopes of the Major Peanut Allergen Ara h 2", *Arch Biochem Biophys.* 342(2): 244-53, Jun. 1997.

Stanley, et al., "Peanut Hypersensitivity. IgE Binding Characterictics of a Recombinant Ara h I Protein", *Adv. Exp Med. Biol.* 409: 213-6, 1996.

Stanworth, et al., "Allergy Treatment with a Peptide Vaccine", *Lancet.* 336(8726): 1279-81, Nov. 24, 1990.

Stanworth, et al., "Nomenclature for Synthetic Peptides Respresentative of Immunoglobulin Chain Sequences", *Bulletin WHO*, 68: 109-111, 1990.

Steinberger, et al., "Construction of a Combinatorial IgE Library from an Allergic Patient. Isolation and Characterization of Human IgE Fabs with Specificity for the Major Timothy Grass Pollen Allergen, Ph1 p 5", *J. Biol. Chem.* 271: 10967-10982, 1996.

Sunderasan, et al., "Latex B-Serum β-1,3-Glucanase (Hev b II) and a Component of the Microhelix (Hev b IV) are Major Latex Allergens" *J. Nat Rubb Res.*,10:82-99, 1995.

Suphioglu, et al., "Peptide Mapping Analysis of Group I Allergens of Grass Pollens", *Int Arch Allergy Immunol.* 102(2): 144-51, 1993.

Suphioglu, et al., "Molecular Cloning and Immunological Characterisation of Cyn D 7, A Novel Calcium-Binding Allergen from Bermuda Grass Pollen", *FEBS Letter*. 402:167-172, 1997.

Suphioglu, et al., "Cloning, Sequencing and Expression in *Escherichia coli* of Pha a 1 and Four Isoforms of Pha a 5, The Major Allergens of Canary Grass Pollen", *Clin. Exp. Allergy*, 25:853-865, 1995.

Sutton, et al., "Detection of IgE and IgG Binding Proteins After Electrophoresis Transfer From Polyacrylamide Gels", *Journal of Immunological Methods*, 52:183-86, 1982.

Svirshchevskaya, et al., "Intravenous Injection of Major and Cryptic Peptide Epitopes of Ribotoxin, Asp F1 Inhibits T Cell Response Induced by Crude *Aspergillus fumigatus* Antigens in Mice", 21(1): 1-8, Jan. 1, 2000.

Sward-Nordmo, et al., "The Glycoprotein Allergen Ag-54 (Cla h II) From *Cladosporium herbarum*", Structural Studies of the Carbohydrate Moiety, *Int. Arch. Allergy Appl. Immunol.*, 85:288-294, 1988.

Szostak, "In Vitro Genetics", *TIBS*, 19:89, 1992.

Takai, et al., "Engineering of the Major House Dust Mite Allergen Der f2 for Allergen-specific Immunotherapy," *Nature Biotechnology*, 15:754-58 (1997).

Takashi, et al., "Engineering of Hypoallergenic Mutants of the *Brassica* Pollen Allergen, Bra r 1, for Immunotherapy," *FEBS Letters*, 434: 255-260 (1998).

Taniai, et al., N-Terminal Amino Acid Sequence of a Major Allergen of Japanese Cedar Pollen (Cry *j* I) *FEBS Letter*, 239:329-332, 1988.

Taylor, et al., "Peanut Oil is Not Allergenic to Peanut Sensitive Individuals", *J. Allergy Clin. Immunol.*, 68: 372-375 (1981).

Taylor, et al., "Evidence for the Ecistence of Multiple Allergens in Peanuts," *J. Allergy Clin. Immunol.* 69:128, 1982.

Teshima, et al., "Isolation and Characterization of a Major Allergenic Component (gp55) of *Aspergillus fumigatus*", *J. Allergy Clin. Immunol.* 92:698-706, 1993.

Texier, et al., "HLA-DR Restricted Peptide Candidates for Bee Venom Immunotherapy", *J. Immunol*, 164(6): 3177-84, Mar. 15, 2000.

Thomas, et al., "Purification of Membrane Proteins," Meth. Enzymol., 182:499-520, 1990.

Tovey, et al., "Cloning and Sequencing of a cDNA Expressing a Recombinant House Dust Mite Protein that Binds Human IgE and Corresponds to an Important Low Molecular Weight Allergen", *J. Exp. Med.* 170:1457-1462, 1989.

Towbin, et al., "Electrophoretic Transfer of Proteins from Polyacrylamide Gels to Nitrocellulose Sheets: Procedure and Some Applications," Proc. Natl. Acad. Sci. USA, 176: 4350-54, 1979.

Trudinger, et al., "cDNA Encoding the Major Mite Allergen Der *f*II" *Clin. Exp. Allergy*, 21:33-38, 1991.

Twardosz, "Molecular Characterization, Expression i *Escherichia coli*, and Epitope Analysis of a Two EF-Hand Calcium-Binding Birch Pollen Allergen, Bet v 4," *Biochem. Biophys. Res. Commun*, 239:197-204, 1997.

Van Der Stoep, et al., "In vivo and in Vitro IgE Isotype Switching in Human B Lymphocytes: Evidence for a Predominantly direct IgM to IgE class Switch Program", *European J. Immunol*, 24 1307-1311 (1994).

Van Hage-Hamsten, "Skin Test Evaluation of Genetically Engineered Hypoallergenic Derivatives of the Major Birch Pollen Allergen, Bet v 1: Results Obtained with A Mix of Two Recombinant Bet v 1 Fragments and Recombinant Bet v 1 Trimer in a Swedish Population Before the Birch Pollen Season", *J Allergy Clin Immunol.* 104(5): 969-77, Nov. 1999.

Van Hage-Hamsten, et al., "N-Terminal Aminoacid Sequence of Major Allergen of the Mite *Lepidoglyphus destructor*," *J. Allergy Clin. Immunol.* 91:353, 1993.

Van Hoeyveld, et al., "Allergenic and Antigenic Activity of Peptide Fragments in a Whey Hydrolysate Formula", 28(9): 1131-7, Sep. 1998.

Van Kampen, et al., "Analysis of B-cell Epitopes in the N-Terminal Region of Chi t 1 component III using Monoclonal Antibodies," *MolecularImmunol*. 31: 1133-1140 (1994).

Van Millgen, et al., Differences Between Specificities of IgE and IgG4 Antibodies: Studies Using Recombinant Chain 1 and Chain 2 of the Major Cat Allergen *Felis domesticus* (d) I. Clin Exp Allergy 25(3): 247-51, Mar. 1995.

Van Milligen, et al., "IgE and IgG4 Binding to Synthetic Peptides of the Cat (*Felis domesticus*) Maj Allergen Fel dI" *Int Arch Allergy Immunol.* 103(3): 274-9, 1994.

Van Milligen, et al., "IgE Epitopes on the Cat (*Felis domesticus*) Major Allergen Fel D I: A Study Wit Overlapping Synthetic Peptides", *J Allergy Clin Immunol.* 93(1 Pt 1): 34-43, Jan. 1994.

Van Ree, et al., "Rabbit IgG Directed to a Synthetic C-Terminal Peptide of the Major Grass Pollen Allergen Lol p I Inhibits Human Basophil Histamine Release Induced by Natural p I". *Int Arch Allergy Immunol.* 106(3): 250-7, Mar. 1995.

Van Ree R, et al., "Lol p XI, a New Major Grass Pollen Allergen, is a Member of a Family of Soybean Trypsin Inhibitor-Related Protein", *J. Allergy Clin Immunol.* 95:970-978, 1995.

Van't Hof, et al., "Epitope Mapping of the Cat (*Felis domesticus*) Major Allergen Fel D I by Overlapping Synthetic Peptides and Monoclonal Antibodies Against Native and Denatured Fel D I", *Allergy*, 48(4) 255-63, May 1993.

Van't Hof, et al., Epitope Mapping of the *Dermatophagoides pteronyssinus* House Dust Mite Major Allergen Der p II Using Overlapping Synthetic Peptides, 28(11): 1225-32, Nov. 1991.

Varela, et al., "Primary Structure of Lep d I, the Main *Lepidoglyphus destructor* Allergen", *Eur J. Biochem.*, 225:93-98, 1994.

Villalba, et al., "The Amino Acid Sequence of Ole e I, the Major Allergen From Olive Tree (*Olea europaea*) Pollen", *Europ. J. Biochem.*, 216:863-869, 1993.

Vives, et al., "A Truncated HIV-1 Tat Protein Basic Domain Rapaidly Translocates Through the Plasma Membrane and Accumulates in the Cell Nucleus", *The Journal of Biological Chemistry*, 272(25): 16010-16017, 1997.

Voller, et al., "Enzyme-Linked Immunosorbent Assay," *Manual of Clinical Laboratory Immunology, Rose, ed.*, Chapter 17, Third Edition, 99-109, 1986.

Vrtala, "High Level Expression in *Escherichia coli* and Purification of Recombinant Plant Profilins: Comparison of IgE Binding Capacity and Allergenic Activity," *Biochem. Biophys. Res. Comm*, 226: 42-50, 1996.

Vrtala, et al., "Conversion of the Major Birch Pollen Allergen, Bet v 1, Into Two Nonanaphylactic T Cell Epitope-Containing Fragments: Candidates for a Novel Form of Specific Immunotherapy", *J. Clin. Invest.* 99(7): 1673-81, Apr. 1997.

Vrtala, et al., "Division of the Major Birch Pollen Allergen Bet v 1, Into Two Non-Anaphylactic Fragments", *Int Arch Allergy Immunol.*, 113: 246-48, 1997.

Wallner, et al., "Immunotherapy with T-Cell Reactive Peptides Derived from Allergens" *Allergy* 49(5): 302-8, May 1994.

Watanabe, et al., "Primary Structure of an Allergenic Peptide Occurring in the Chymotryptic Hydrolysate of Gluten", *Biosci Biotechnol Biochem.* 59(8): 1596-7, Aug. 1995.

Weber, et al., "Characteristics of the Aspargine-Linked Oligosaccharide from Honey-Bee Venom Phospholipase A2". *Comp. Biochem. Physiol.* 83B: 321-324, 1986.

Weber, et al., "Specific Interaction of IgE Antibodies with a Carbohydrate Epitope of Honey Bee Venom Phospholipase A2", *Allergy*, 42: 464-470, 1987.

Wiedermann, et al., "Suppression of Antigen-Specific T- and B-Cell Responses by Intranasal or Oral Administration of Recombinant Bet v 1, The Major Birch Pollen Allergen, in a Murine Model of Type I Allergy", *J. Allergy Clin Immunol.*, 103(6): 1202-10, Jun. 1999.

Williams, et al., "Indentification of Epitopes Within Beta Lactoglobulin Recognised by Polyclonal Antibodies Using Phage Display and PEPSCAN", *J Immunol Methods.* 213(1): 1-17, Apr. 1998.

Woodfolk, et al., "Trichophyton Antigens Associated with IgE Antibodies and Delayed Type Hypersensitivity", *J. Biol. Chem.* 273:29489-29496, 1998.

Wu, et al., "Isolation and Preliminary Characterization of cDNA Encoding American Cockroach Allergens", *J. Allergy Clin. Immunol.*, 96:352-359, 1995.

Yamamoto, et al., "DNA From Bacteria, But Not From Vertebrates, Induces Interferons, Activates Natural Killer Cells and Inhibits Tumor Growth," *Microbiol. Immunol.* 36(9): 983-97, 1992.

Yang, et al., "Immunologic Characterization of a Recombinant Kentucky Bluegrass (*Poa pratensis*) Allergenic Peptide", *J Allergy Clin Immunol.* 87(6): 1096-104, Jun. 1991.

Yeang, et al., "The 14.6 kd Rubber Elongation Factor (Hev b 1) and 24 kd (Hev b 3) Rubber Particle Proteins are Recognized by IgE from Patients with Spina Bifida and Latex Allergy" *J. Allergy Clin Immunol*, 98(3): 628-639, 1996.

Yssel, et al., "Peptide Induced Anergy of Human Allergen-Specific T Cells" *Adv Exp. Med Biol.* 409: 405-10, 1996.

Yunginger, et al., "Fatal Food-Induced Anaphylaxis," *JAMA*, 260: 1450-2, 1988.

Zimmerman, et al., "CpG Oligodexoynucleotides Trigger Protective and Curative Th1 Responses in Lethal Murine Leishmaniasis," *J. Immunol.* 160(8): 3627-30, 1998.

* cited by examiner

| SEQ. ID. NO. | | | | |
|---|---|---|---|---|
| 44. TNQRSPPGERTRGRQPGDYDDDR.RQPRREEGGRWGPAGPRERE.REEDWRQPR | | | | |
| 45. TNQRSPPGER | | | | |
| 46. QRSPPGERTR | | | | |
| 47. SPPGERTRGR | | | | |
| 48. PGERTRGRQP | | | | |
| 49. ERTRGRQPGD | | | | |
| 50. TRGRQPGDYD | | | | |
| 51. GRQPGDYDDD | | | | |
| 52. QPGDYDDDRR | | | | |
| 53. GDYDDDRRQP | | | | |
| 54. YDDDRRQPRR | | | | |
| 55. DDDRRQPRREE | | | | |
| 56. RRQPRREEGG | | | | |
| 57. QPRREEGGRW | | | | |
| 58. RREEGGRWGP | | | | |
| 59. EGGRWGPAG | | | | |
| 60. GGRWGPAGPR | | | | |
| 61. RWGPAGPRER | | | | |
| 62. GPAGPRERER | | | | |
| 63. AGPRERERE | | | | |
| 64. PREREEDW | | | | |
| 65. EREEDWRQ | | | | |
| 66. EREEDWRQPR | | | | |

FIG. 1

|  | 55 | 6 | 65 | 7 | 75 |
|---|---|---|---|---|---|
| SEQ. ID. NO. | | | | | |
| 67. | DSYE|RDPYSP|SQ|DPYSPS|PYDR |
| 68. | DSYE|RDPYSP| | | |
| 69. | YE|RDPYSP|SQ | | |
| 70. | |RDPYSP|SQ|DP | |
| 71. | |PYSPSQ|DPYS | | |
| 72. | |SPSQ|DPYSPS | | |
| 73. | |SQ|DPYSPS|PY | |
| 74. | | |DPYSPS|PYDR | |

FIG. 2

|  | 299 | | 321 |
|---|---|---|---|
| SEQ. ID. NO. | | | |
| 75. | EEEYDEDE|YEYDEEDRR|RGRGSR |
| 76. | EEEYDEDE|YEYDEED| |
| 77. | EYDEDE|YEYDEEDRR| |
| 78. | DEDE|YEYDEEDRR|RG |
| 79. | DE|YEYDEEDRR|RGRG |
| 80 | |YEYDEEDRR|RGRGSR |
| 81. | |YDEEDRRRGRGSRGR| |

FIG. 3

NUCLEIC ACIDS ENCODING ARA H 3 POLYPEPTIDES

This application is a continuation of U.S. Ser. No. 09/141,220 filed Aug. 27, 1998 now abandoned. U.S. Ser. No. 09/141,220 is a continuation-in-part of U.S. Ser. No. 08/717,933 filed Sep. 26, 1996 now abandoned, and claims priority to U.S. Ser. No. 60/073,283 filed Jan. 31, 1998; U.S. Ser. No. 60/074,590 filed Feb. 13, 1998; U.S. Ser. No. 60/074,624 filed Feb. 13, 1998; and U.S. Ser. No. 60/074,633 filed Feb. 13, 1998. U.S. Ser. No. 09/141,220 also claims priority under 35 U.S.C. §§ 120 and 371 to PCT/US96/15222 filed Sep. 23, 1996.

The United States government has rights in this invention by virtue of grants from the National Institute of Health RO1-AI33596.

BACKGROUND OF THE INVENTION

Allergic disease is a common health problem affecting humans and companion animals (mainly dogs and cats) alike. Allergies exist to foods, molds, grasses, trees, insects, pets, fleas, ticks and other substances present in the environment. It is estimated that up to 8% of young children and 2% of adults have allergic reactions just to foods alone. Some allergic reactions (especially those to foods and insects) can be so severe as to be life threatening. Problems in animals tend to be less severe, but very common. For example, many dogs and cats have allergies to flea saliva proteins, grasses, and other common substances present in the environment.

Allergy is manifested by the release of histamines and other mediators of inflammation by mast cells which are triggered into action when IgE antibodies bound to their receptors on the mast cell surface are cross linked by antigen. Other than avoidance, and drugs (e.g. antihistamines, decongestants, and steroids) that only treat symptoms and can have unfortunate side effects and often only provide temporary relief, the only currently medically accepted treatment for allergies is immunotherapy. Immunotherapy involves the repeated injection of allergen extracts, over a period of years, to desensitize a patient to the allergen. Unfortunately, traditional immunotherapy is time consuming, usually involving years of treatment, and often fails to achieve its goal of desensitizing the patient to the allergen. Furthermore, it is not the recommended treatment for food allergies, such as peanut allergies, due to the risk of anaphylaxis.

Noon (Noon, *Lancet* 1911; 1:1572-73) first introduced allergen injection immunotherapy in 1911, a practice based primarily on empiricism with non-standardized extracts of variable quality. More recently the introduction of standardized extracts has made it possible to increase the efficacy of immunotherapy, and double-blind placebo-controlled trials have demonstrated the efficacy of this form of therapy in allergic rhinitis, asthma and bee-sting hypersensitivity (BSAC Working Party, *Clin. Exp. Allergy* 1993; 23:1-44). However, increased risk of anaphylactic reactions has accompanied this increased efficacy. For example, initial trials of immunotherapy to food allergens has demonstrated an unacceptable safety:efficacy ratio (Oppenheimer et al. *J. Allergy Clin. Immun.* 1992; 90:256-62; Sampson, *J. Allergy Clin. Immun.* 1992; 90:151-52; Nelson et al. *J. Allergy Clin. Immun.* 1996; 99:744-751). Results like these have prompted investigators to seek alternative forms of immunotherapy as well as to seek other forms of treatment.

Initial trials with allergen-non-specific anti-IgE antibodies to deplete the patient of allergen-specific IgE antibodies have shown early promise (Boulet, et al. 1997; 155:1835-1840; Fahy, et al. *American J. Respir. Crit. Care Med.* 1997; 155: 1828-1834; Demoly P. and Bousquet J. *American J. Resp. Crit. Care Med.* 1997; 155:1825-1827). On the other hand, trials utilizing immunogenic peptides (representing T cell epitopes) have been disappointing (Norman, et al. *J. Aller. Clin. Immunol.* 1997; 99:S127). Another form of allergen-specific immunotherapy which utilizes injection of plasmid DNA (Raz et al. *Proc. Nat. Acad. Sci.* USA 1994; 91:9519-9523; Hz et al. *Int. Immunol.* 1996; 8:1405-141 1) remains unproven.

There remains a need for a safe and efficacious therapy for allergies, especially those where traditional immunotherapy is ill advised due to risk to the patient or lack of efficacy. There is also a need for alternatives to therapies, for example, by creating foods, materials or substances that do not include the allergens that are most problematic, or which contain modified allergens which do not elicit the same reaction. While the technology to make genetically engineered plants and animals is at this point well established, useful modifications would require understanding how allergens can be modified so that they retain the essential functions for the plants' and animals' nutritional value, taste characteristics, etc., but no longer elicit as severe an allergic response.

It is therefore an object of the present invention to provide a method for decreasing the allergenicity of allergens either by modifying the allergen itself or by producing a compound that would mask the epitope and thus prevent binding of IgE.

It is a further object of the present invention to provide allergens that elicit fewer IgE mediated responses.

It is still another object of the present invention to provide a method to make genetically engineered plants and animals that elicit less of an allergic response than the naturally occurring organisms.

SUMMARY OF THE INVENTION

It has been determined that allergens, which are characterized by both humoral (IgG and IgE) and cellular (T cell) binding sites, can be made less allergenic by modifying the IgE binding sites. The IgE binding sites can be eliminated by masking the site with a compound that would prevent IgE binding or by altering as little as a single amino acid within the protein to eliminate IgE binding. The method allows the protein to be altered as minimally as possible, (i.e. only within the IgE-binding sites) while retaining the ability of the protein to activate T cells and, optionally, to bind IgG. Binding sites are identified using known techniques, such as by binding with antibodies in pooled sera obtained from individuals known to be immunoreactive with the allergen to be modified. Proteins that are modified to alter IgE binding are screened for binding with IgG and/or activation of T cells.

Peanut allergens (Ara h 1, Ara h 2, and Ara h 3) have been used in the examples to demonstrate alteration of IgE binding sites while retaining binding to IgG and activation of T cells. The critical amino acids within each of the IgE binding epitopes of the peanut protein that are important to immunoglobulin binding were determined. Substitution of even a single amino acid within each of the epitopes led to loss of IgE binding. Although the epitopes shared no common amino acid sequence motif, the hydrophobic residues located in the center of the epitope appeared to be most critical to IgE binding.

Standard techniques such as a skin test for wheal and flare formation can be used to assess decreased allergenicity of modified proteins, created as described in the examples. The modified allergens can also be tested for binding to IgG and proliferation of T cells, and modified allergens selected for optimal stimulation of T cells and binding IgG.

The immunotherapeutics can be delivered by standard techniques, using injection, by aerosol, sublingually, topically (including to a mucosal surface), and by gene therapy (for example, by injection of the gene encoding the immunotherapeutic into muscle or skin where it is transiently expressed for a time sufficient to induce tolerance).

This method and the criteria for identifying and altering allergens can be used to design useful proteins (including nucleotide molecules encoding the proteins) for use in immunotherapy, to make a vaccine and to genetically engineer organisms such as plants and animals which then produce proteins with less likelihood of eliciting an IgE response. Techniques for engineering plants and animals are well known. Based on the information obtained using the method described in the examples, one can engineer plants or animals to cause either site specific mutations in the gene encoding the protein(s) of interest, or to knock out the gene and then insert the gene encoding the modified protein.

BRIEF DESCRIPTION OF THE DRAWINGS

FIG. 1 shows an example of how IgE binding epitopes were mapped to a specific amino acid sequence on the Ara h 1 allergen. In particular, FIG. 1 depicts twenty-two 10-mer peptides (SEQ ID NOs. 45-66) that span amino acid residues 82-133 (SEQ ID NO. 44) of the Ara h 1 allergen (SEQ ID NO. 2). This region of the Ara h 1 allergen includes epitopes 4, 5, 6, and 7, as identified in Table 1.

FIG. 2 shows an example of how IgE binding epitopes were mapped to a specific amino acid sequence on the Ara h 2 allergen. In particular, FIG. 2 depicts seven 10-mer peptides (SEQ ID NOs. 68-74) that span amino acid residues 55-76 (SEQ ID NO. 67) of the Ara h 2 allergen (SEQ ID NO. 4). This region of the Ara h 2 allergen includes epitopes 6 and 7 as identified in Table 2.

FIG. 3 shows an example of how IgE binding epitopes were mapped to a specific amino acid sequence on the Ara h 3 allergen. In particular, FIG. 3 depicts six 15-mer peptides (SEQ ID NOs. 76-81) that span amino acid residues 299-321 (SEQ ID NO. 75) of the Ara h 3 allergen (SEQ ID NO. 6). This region of the Ara h 3 allergen includes epitope 4 as identified in Table 3.

DETAILED DESCRIPTION OF THE INVENTION

Definitions

Figure 4:
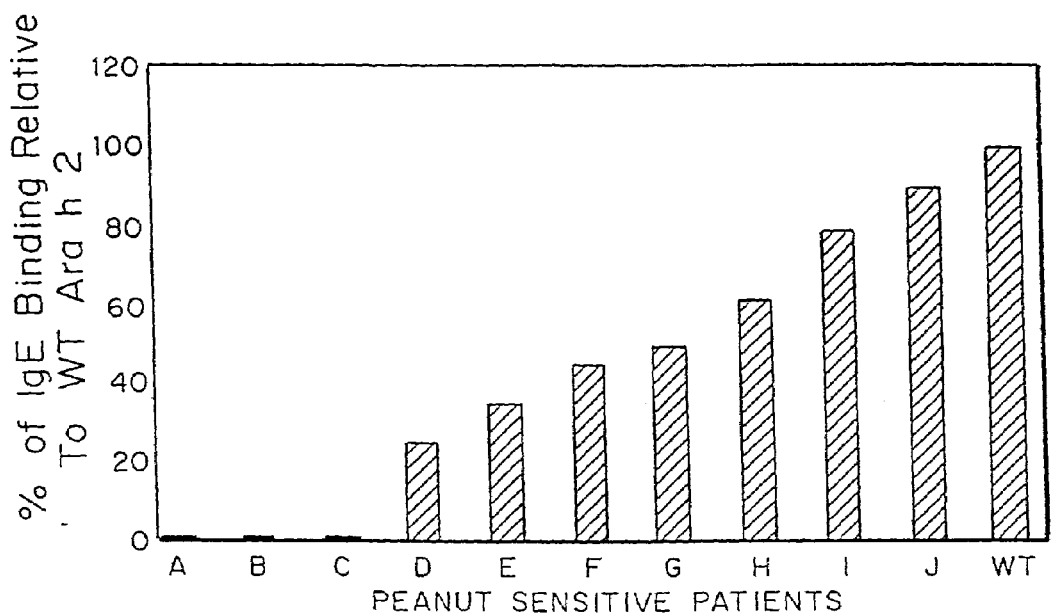
FIG. 4 shows the effect the modified Ara h 2 protein has on IgE binding.
Figure 5:
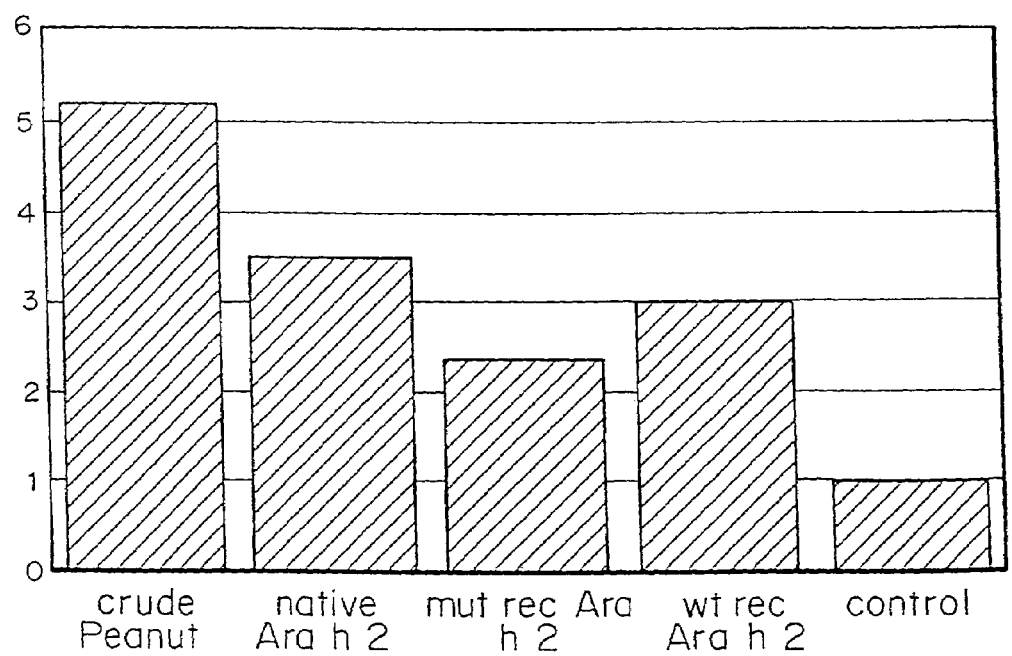
FIG. 5 shows the results of T cell proliferation assays using the wild-type and modified Ara h 2 protein.

The following definitions are used herein.

An antigen is a molecule that elicits production of antibody (a humoral response) or an antigen-specific reaction with T cells (a cellular response).

An allergen is a subset of antigens which elicits IgE production in addition to other isotypes of antibodies.

An allergic reaction is one that is IgE mediated with clinical symptoms primarily involving the cutaneous (uticaria, angiodema, pruritus), respiratory (wheezing, coughing, laryngeal edema, rhinorrhea, watery/itching eyes), gastrointestinal (vomiting, abdominal pain, diarrhea), and cardiovascular (if a systemic reaction occurs) systems.

An epitope is a binding site including an amino acid motif of between approximately six and fifteen amino acids which can be bound by either an immunoglobulin or recognized by a T cell receptor when presented by an antigen presenting cell in conjunction with the major histocompatibility complex (MHC). A linear epitope is one where the amino acids are recognized in the context of a simple linear sequence. A conformational epitope is one where the amino acids are recognized in the context of a particular three dimensional structure.

An immunodominant epitope is one which is bound by antibody in a large percentage of the sensitized population or where the titer of the antibody is high, relative to the percentage or titer of antibody reaction to other epitopes present in the same protein.

A decreased allergic reaction is characterized by a decrease in clinical symptoms following treatment of symptoms associated with exposure to an allergen, which can involve respiratory, gastrointestinal, skin, eyes, ears and mucosal surfaces in general.

An antigen presenting cell (an APC) is a cell which processes and presents peptides to T cells to elicit an antigen-specific response.

Immunostimulatory sequences are oligodeoxynucleotides of bacterial, viral or invertebrate origin that are taken-up by APCs and activate them to express certain membrane receptors (e.g., B7-1 and B7-2) and secrete various cytokines (e.g., IL-1, IL-6, IL-12, TNF). These oligodeoxynucleotides containing unmethylated CpG motifs cause brisk activation and when injected into animals in conjunction with antigen, appear to skew the immune response to a Th1-type response. See, for example, Yamamoto, et al., *Microbiol. Immunol.* 36, 983 (1992); Krieg, et al., *Nature* 374, 546-548 (1995); Pisetsky, *Immunity* 5, 303 (1996); and Zimmerman, et al., *J. Immunol.* 160, 3627-3630 (1998).

I. Diagnostic and Therapeutic Reagents.

The first step in making the modified allergen is to identify IgE binding sites and/or immunodominant IgE binding sites. The second step is to mutate one or more of the IgE binding sites, preferably including at a minimum one of the immunodominant sites, or to react the allergen with a compound that selectively blocks binding to one or more of the IgE binding sites. The third step is to make sufficient amounts of the modified allergen for administration to persons or animals in need of tolerance to the allergen, where the modified allergen is administered in a dosage and for a time to induce tolerance, or for diagnostic purposes. The modified allergen can be administered by injection, or in some cases, by ingestion or inhalation.

A. Allergens.

Many allergens are known that elicit allergic responses, which may range in severity from mildly irritating to life-threatening. Food allergies are mediated through the interaction of IgE to specific proteins contained within the food. Examples of common food allergens include proteins from peanuts, milk, grains such as wheat and barley, soybeans, eggs, fish, crustaceans, and mollusks. These account for greater than 90% of the food allergies (Taylor, Food Techn. 39, 146-152 (1992). The IgE binding epitopes from the major allergens of cow milk (Ball, et al. (1994) *Clin. Exp. Allergy*, 24, 758-764), egg (Cooke, S. K. and Sampson, H. R. (1997) *J. Immunol.*, 159, 2026-2032), codfish (Aas, K., and Elsayed, S. (1975) *Dev. Biol. Stand.* 29, 90-98), hazel nut (Elsayed, et al. (1989) *Int. Arch. Allergy Appl. Immunol.* 89, 410-415), peanut (Burks et al., (1997) *Eur. J. Biochemistry*, 245:334-339; Stanley et al., (1997) *Archives of Biochemistry and Biophysics*, 342:244-253), soybean (Herein, et al. (1990) *Int. Arch. Allergy Appl. Immunol.* 92, 193-198) and shrimp (Shanty, et al. (1993) *J. Immunol.* 151, 5354-5363) have all been elucidated, as have others Other allergens include proteins from insects such as flea, tick, mite, fire ant, cockroach, and bee as well as molds, dust, grasses, trees, weeds, and proteins from mammals including horses, dogs, cats, etc.

The majority of allergens discussed above elicit a reaction when ingested, inhaled, or injected. Allergens can also elicit a reaction based solely on contact with the skin. Latex is a well known example. Latex products are manufactured from a milky fluid derived from the rubber tree, *Hevea brasiliensis* and other processing chemicals. A number of the proteins in latex can cause a range of allergic reactions. Many products contain latex, such as medical supplies and personal protective equipment. Three types of reactions can occur in persons sensitive to latex: irritant contact dermatitis, and immediate systemic hypersensitivity. Additionally, the proteins responsible for the allergic reactions can fasten to the powder of latex gloves This powder can be inhaled, causing exposure through the lungs. Proteins found in latex that interact with IgE antibodies were characterized by two-dimensional electrophoresis. Protein fractions of 56, 45, 30, 20, –14, and less than 6.5 kd were detected (Posch A. et al., (1997) *J. Allergy Clin. Immunol.* 99(3), 385-395). Acidic proteins in the 8-14 kd and 22-24 kd range that reacted with IgE antibodies were also identified (Posch A. et al., (1997) *J. Allergy Clin. Immunol.* 99(3), 385-395. The proteins prohevein and hevein, from hevea brasiliensis, are known to be major latex allergens and to interact with IgE (Alenius, H., et al., *Clin. Exp. Allergy* 25(7), 659-665; Chen Z., et al., (1997) *J. Allergy Clin. Immunol.* 99(3), 402-409). Most of the IgE binding domains have been shown to be in the hevein domain rather than the domain specific for prohevein (Chen Z., et al., (1997) *J. Allergy Clin. Immunol.* 99(3), 402-409). The main IgE-binding epitope of prohevein is thought to be in the N-terminal, 43 amino acid fragment (Alenius H., et al., (1996) *J. Immunol.* 156(4), 1618-1625). The hevein lectin family of proteins has been shown to have homology with potato lectin and snake venom disintegrins (platelet aggregation inhibitors) (Kielisqewski, M. L., et al., (1994) *Plant J.* 5(6), 849-861).

B. Identification of IgE Binding Sites.

Allergens typically have both IgE and IgG binding sites and are recognized by T cells. The binding sites can be determined either by using phage display libraries to identify conformational epitopes (Eichler and Houghten, (1995) *Molecular Medicine Today* 1, 174-180; Jensen-Jarolim et al., (1997) *J. Appl. Clin. Immunol.* 101, 5153a) or by using defined peptides derived from the known amino acid sequence of an allergen (see examples below), or by binding of whole protein or protein fragments to antibodies, typically antibodies obtained from a pooled patient population known to be allergic to the allergen. It is desirable to modify allergens to diminish binding to IgE while retaining, their ability to activate T cells and in some embodiments by not significantly altering or decreasing IgG binding capacity. This requires modification of one or more IgE binding sites in the allergen.

A preferred modified allergen is one that can be used with a majority of patients having a particular allergy. Use of pooled sera from allergic patients allows determination of one or more immunodominant epitopes in the allergen. Once some or all of the IgE binding sites are known, it is possible to modify the gene encoding the allergen, using site directed mutagenesis by any of a number of techniques, to produce a modified allergen as described below, and thereby express modified allergens. It is also possible to react the allergen with a compound that achieves the same result as the selective mutation, by making the IgE binding sites inaccessible, but not preventing the modified allergen from activating T cells, and, in some embodiments, by not significantly altering or decreasing IgG binding.

Assays to assess an immunologic change after the administration of the modified allergen are known to those skilled in the art. Conventional assays include RAST (Sampson and Albergo, 1984), ELISAs (Burks, et al. 1986) immunoblotting (Burks, et al. 1988), and in vivo skin tests (Sampson and Albergo 1984). Objective clinical symptoms can be monitored before and after the administration of the modified allergen to determine any change in the clinical symptoms.

It may be of value to identify IgEs which interact with conformational rather than linear epitopes. Due to the complexity and heterogeneity of patient serum, it may be difficult to employ a standard immobilized allergen affinity-based approach to directly isolate these IgEs in quantities sufficient to permit their characterization. These problems can be avoided by isolating some or all of the IgEs which interact with conformational epitopes from a combinatorial IgE phage display library.

Steinberger et al. (Steinberger, P., Kraft D. and Valenta R. (1996) "Construction of a combinatorial IgE library from an allergic patient: Isolation and characterization of human IgE Fabs with specificity for the major Timothy Grass pollen antigen," Phl p. 5 *J. Biol. Chem.* 271, 10967-10972) prepared a combinatorial IgE phage display library from mRNA isolated from the peripheral blood mononuclear cells of a grass allergic patient. Allergen-specific IgEs were selected by panning filamentous phage expressing IgE Fabs on their surfaces against allergen immobilized on the wells of 96 well microtiter plates. The cDNAs were than isolated from allergen-binding phage and transformed into *E. coli* for the production of large quantities of monoclonal, recombinant, allergen-specific IgE Fabs.

If native allergen or full length recombinant allergen is used in the panning step to isolate phage, then Fabs corresponding to IgEs specific for conformational epitopes should be included among the allergen-specific clones identified. By screening the individual recombinant IgE Fabs against denatured antigen or against the relevant linear epitopes identified for a given antigen, the subset of conformation-specific clones which do not bind to linear epitopes can be defined.

To determine whether the library screening has yielded a complete inventory of the allergen-specific IgEs present in patient serum, an immunocompetition assay can be performed. Pooled recombinant Fabs would be preincubated with immobilized allergen. After washing to remove unbound Fab, the immobilized allergen would then be incubated with patient serum. After washing to remove unbound serum proteins, an incubation with a reporter-coupled secondary antibody specific for IgE Fc domain would be performed. Detection of bound reporter would allow quantitation of the extent to which serum IgE was prevented from binding to allergen by recombinant Fab. Maximal, uncompeted serum IgE binding would be determined using allergen which had not been preincubated with Fab or had been incubated with nonsense Fab. If IgE binding persists in the face of competition from the complete set of allergen-specific IgE Fab clones, this experiment can be repeated using denatured antigen to determine whether the epitopes not represented among the cloned Fabs are linear or conformational.

Production of Recombinant or Modified Allergens

A modified allergen will typically be made using recombinant techniques. Expression in a procaryotic or eucaryotic host including bacteria, yeast, and baculovirus-insect cell systems are typically used to produce large (mg) quantities of the modified allergen. It is also possible to make the allergen synthetically, if the allergen is not too large, for example, less than about 25-40 amino acids in length.

Production of Transgenic Plants and Animals

Transgenic plants or animals expressing the modified allergens have two purposes. First, they can be used as a source of modified allergen for use in immunotherapy and second, appropriately modified plants or animals can be substituted for the original plant or animal, making immunotherapy unnecessary. Furthermore, it is possible that eating modified peanuts or cod fish, for example, could have either or both of two effects: (1) not imparting an allergic response on their own and (2) conferring protection from the unmodified source by acting as an immunotherapeutic agent for the unmodified source. Methods for engineering of plants and animals are well known and have been for a decade. For example, for plants see Day, (1996) *Crit. Rev. Food Sci. & Nut.* 36(S), 549-567, the teachings of which are incorporated herein. See also Fuchs and Astwood (1996) *Food Tech.* 83-88 Methods for making recombinant animals are also well established. See, for example, Colman, A. "Production of therapeutic proteins in the milk of transgenic livestock" (1998) *Biochem. Soc. Symp.* 63, 141-147; Espanion and Niemann, (1996) *DTW Dtxch Tierarztl Wochenschr* 103(8-9), 320-328; and Colman, *Am. J. Clin. Nutr.* 63(4), 639S-6455S, the teachings of which are incorporated herein. One can also induce site specific changes using homologous recombination and/or triplex forming oligomers. See, for example, Rooney and Moore, (1995) *Proc. Natl. Acad. Sci. USA* 92, 2141-2149; Agrawal, et al., *BioWorld Today*, vol. 9, no. 41, p. 1 "Chimeriplasty—Gene Surgery, Not Gene Therapy—Fixes Flawed Genomic Sequences" David N. Leff.

Production and Screening of Compounds Blocking IgE Binding Sites

Once the IgE binding sites have been identified, it is also possible to block or limit binding to one or more of these sites by reacting the allergen with a compound that does not prevent the allergen from activating T cells, and in some embodiments does not significantly alter or decrease IgG binding capacity, resulting in a modified allergen similar in functionality to that produced by mutation. There are two principal ways to obtain compounds which block IgE binding sites: combinatorial libraries and combinatorial chemistry.

Identification of Compounds that Mask IgE Binding Sites Through Application of Combinatorial Chemistry In some cases it may be preferable to utilize non-peptide compounds to block binding of IgE to the allergen by masking the IgE binding epitope. This can be accomplished by using molecules that are selected from a complex mixture of random molecules in what has been referred to as "in vitro genetics" or combinatorial chemistry (Szostak, *TIBS* 19:89, 1992). In this approach a large pool of random and defined sequences is synthesized and then subjected to a selection and enrichment process. The selection and enrichment process involves the binding of the IgE binding epitopes to a solid support, followed by interaction with the products of various combinatorial libraries. Those molecules which do not bind these molecules at all are removed immediately by elution with a suitable solvent. Those molecules which bind to the epitopes will remain bound to the solid support, whereas, unbound compounds will be removed from the column. Those compounds bound to the column can be removed, for example, by competitive binding. Following removal of these compounds, the compounds which have bound can be identified, using methodology well known to those of skill in the art, to isolate and characterize those compounds which bind to or interact with IgE binding epitopes. The relative binding affinities of these compounds can be compared and optimum compounds identified using competitive binding studies which are well known to those of skill in the art.

Identification of Compounds that Interact with IgE Binding Sites Through Application of Combinatorial Phage Display Libraries Recombinant, monoclonal Fabs directed against conformational epitopes, identified as described above, can be used as reagents to assist in the definition of the biochemical nature of these epitopes. Cross-linking studies employing derivatized Fabs can be employed to label amino acid residues in the vicinity of the epitopes. Similarly, the Fabs can be used in protease protection studies to identify those domains of the allergen protein which are shielded from protease degradation by pre-binding of a specific Fab. Experiments employing recombinant monoclonal Fabs as reagents to label or protect from labeling should permit at least partial elucidation of the structures of conformational epitopes.

"Humanized" recombinant Fabs should bind to allergens if injected into a patient and thus prevent the binding of these allergens to native IgE. Since the Fabs cannot interact with the Fcϵ receptor, the binding of the IgE Fabs to allergen would not be expected to elicit mast cell degranulation. Allergen should be neutralized as it is by protective IgGs.

Anti-idiotype antibodies directed against the conformational epitope-specific Fabs should resemble the conformation epitopes themselves. Injection of these anti-idiotype antibodies should induce the production of anti-anti-idiotype IgGs which would recognize, bind to and inactivate the conformational epitopes. The method through which the anti-idiotype antibodies would be produced (i.e. animal immunization, "in vitro" immunization or recombinant phage display library) would have to be determined. Similarly, the possibility that the anti-idiotype antibodies (which resemble the conformational epitopes) would be recognized by patient IgEs and induce mast cell degranulation needs to be considered.

II. Diagnostic and Therapeutic Procedures Using Modified Allergens.

It is important to administer the modified allergen to an individual (human or animal) to decrease the clinical symptoms of allergic disease by using a method, dosage, and carrier which are effective. Allergen will typically be administered in an appropriate carrier, such as saline or a phosphate saline buffer. Allergen can be administered by injection subcutaneously, intramuscularly, or intraperitoneally (most humans would be treated by subcutaneous injection), by aerosol, inhaled powder, or by ingestion.

Therapy or desensitization with the modified allergens can be used in combination with other therapies, such as allergen-non-specific anti-IgE antibodies to deplete the patient of allergen-specific IgE antibodies (Boulet, et al. (1997) 155: 1835-1840; Fahy, et al. (1997) *American J Respir. Crit. Care Med.* 155:1828-1834; Demoly, P. and Bousquet (1997) *J Am J Resp. Crit. Care Med.* 155:1825-1827), or by the pan specific anti-allergy therapy described in U.S. Ser. No. 08/090, 375 filed Jun. 4, 1998, by M. Caplan and H. Sosin. Therapy with the modified allergen can also be administered in combination with an adjuvant such as IL-12, IL-16, IL-18, IFNγ.

The nucleotide molecule encoding the modified allergen can also be administered directly to the patient, for example, in a suitable expression vector such as a plasmid, which is injected directly into the muscle or dermis, or through administration of genetically engineered cells.

In general, effective dosages will be in the picogram to milligram range, more typically microgram to milligram. Treatment will typically be between twice/weekly and once a month, continuing for up to three to five years, although this is highly dependent on the individual patient response.

The modified allergen can also be used as a diagnostic to characterize the patient's allergies, using techniques such as those described in the examples.

EXAMPLES

Peanut allergy is one of the most common and serious of the immediate hypersensitivity reactions to foods in terms of persistence and severity of reaction. Unlike the clinical symptoms of many other food allergies, the reactions to peanuts are rarely outgrown, therefore, most diagnosed children will have the disease for a lifetime (Sampson, H. A., and Burks, A. W. (1996) *Annu. Rev. Nutr.* 16, 161-77; Bock, S. A. (1985) *J. Pediatr.* 107, 676-680). The majority of cases of fatal food-induced anaphylaxis involve ingestion of peanuts (Sampson et al., (1992) *NEJM* 327, 380-384; Kaminogawa, S. (1996) *Biosci. Biotech. Biochem.* 60, 1749-1756). The only effective therapeutic option currently available for the prevention of a peanut hypersensitivity reaction is food avoidance. Unfortunately, for a ubiquitous food such as a peanut, the possibility of an inadvertent ingestion is great.

The examples described below demonstrate identification, modification, and assessment of allergenicity of the major peanut allergens, Ara h 1, Ara h 2, and Ara h 3. Detailed experimental procedures are included for Example 1. These same procedures were used for Examples 2-5. The nucleotide sequences of Ara h 1, Ara h 2, and Ara h 3, are shown in SEQ ID NOs. 1, 3, and 5, respectively. The amino acid sequences of Ara h 1, Ara h 2, and Ara h 3 are shown in SEQ ID NOs. 2, 4, and 6 respectively.

Example 1

Identification of Linear IgE Binding Epitopes

Due to the significance of the allergic reaction and the widening use of peanuts as protein extenders in processed foods, there is increasing interest in defining the allergenic proteins and exploring ways to decrease the risk to the peanut-sensitive individual. Various studies over the last several years have identified the major allergens in peanuts as belonging to different families of seed storage proteins (Burks, et al. (1997) *Eur. J. Biochem.* 245, 334-339; Stanley, et al. (1997) *Arch. Biochem. Biophys.* 342, 244-253). The major peanut allergens Ara h 1, Ara h 2, and Ara h 3 belong to the vicilin, conglutin and glycinin families of seed storage proteins, respectively. These allergens are abundant proteins found in peanuts and are recognized by serum IgE from greater than 95% of peanut sensitive individuals, indicating that they are the major allergens involved in the clinical etiology of this disease (Burks, et al. (1995) *J. Clinical Invest.,* 96, 1715-1721). The genes encoding Ara h 1 (SEQ ID NO. 1), Ara h 2 (SEQ ID NO. 3), and Ara h 3 (SEQ ID NO. 5) and the proteins encoded by these genes (SEQ ID NOs. 2, 4, 6) have been isolated and characterized. The following studies were conducted to identify the IgE epitopes of these allergens recognized by a population of peanut hypersensitive patients and a means for modifying their affinity for IgE.

Experimental Procedures

Serum IgE. Serum from 15 patients with documented peanut hypersensitivity reactions (mean age, 25 yrs) was used to determine relative binding affinities between wild-type and mutant Ara h 1 synthesized epitopes. The patients had either a positive double-blind, placebo-controlled, food challenge or a convincing history of peanut anaphylaxis (laryngeal edema, severe wheezing, and/or hypotension; Burks, et al. (1988) *J. Pediatr.* 113, 447-451). At least 5 ml of venous blood was drawn from each patient, allowed to clot, and serum was collected A serum pool from 12 to 15 patients was made by mixing equal aliquots of serum IgE from each patient. The pools were then used in immunoblot analysis.

Peptide synthesis. Individual peptides were synthesized on a derivatized cellulose membrane using 9-fluorenyll-methoxycarbonyl (Fmoc) amino acid active esters according to the manufacturer's instructions (Geriosys Biotechnologies, Woodlands, Tex.; Fields, G. B and Noble, R. L. (1990) *Int. J Peptide Protein Res.* 35, 161-214). Fmoc-amino acids (N-terminal blocked) with protected side chains were coupled in the presence of 1-methyl-2-pyrrolidone to a derivatized cellulose membrane. Following washing with dimethylformamide (DMF), unreacted terminal amino groups were blocked from further reactions by acetylation with acetic anhydride. The N-terminal Fmoc blocking group was then removed by reaction with 20% piperidine and 80% DMF, v/v. The membrane was washed in DMF followed by methanol, the next reactive Fmoc-amino acid was then coupled as before, and the sequence of reactions was repeated with the next amino acid. When peptide synthesis was complete, the side chains were deprotected with a mixture of dichloromethane (DCM), triflouroacetic acid, and triisobutylsilane (1.0:1.0:0.5), followed by successive washes in DCM, DMF, and methanol. Peptides synthesis reactions were monitored by bromophenol blue color reactions during certain steps of synthesis. Cellulose derivitised membranes and Fmoc-amino acids were supplied by Genosys Biotechnologies. All other chemical were purchased from Aldrich Chemical Company, Inc. (Milwaukee, Wis.) or Fluka (Bucks, Switzerland). Membranes were either probed immediately or stored at −20° C. until needed.

IgE binding assays. Cellulose membranes containing synthesized peptides were washed 3 times in Tris-buffered saline (TBS; 136 mM NaCl, 2.7 mM KCl, and 50 mM trizma base pH 8.0) for 10 min at room temperature (RT) and then incubated overnight in blocking buffer: [TBS, 0.05% Tween™ 20; concentrated membrane blocking buffer supplied by Genosys; and sucrose (0.0:1.0:0.5)]. The membrane was then incubated in pooled sera diluted in 1:5 in 20 mM Tris-Cl pH 7.5, 150 mM NaCl, and 1% bovine serum albumin overnight at 4° C. Primary antibody was detected with $^{125}$I-labeled equine anti-human IgE (Kallestad, Chaska, Minn.).

Quantitation of IgE binding. Relative amounts of IgE binding to individual peptides were determined by a Bio-Rad (Hercules, Calif.) model GS-700 imaging laser densitometer and quantitated with Bio-Rad molecular analyst software. A background area was scanned and subtracted from the obtained values. Following quantitation, wild-type intensities were normalized to a value of one and the mutants were calculated as percentages relative to the wild-type.

Synthesis and purification of recombinant Ara h 2protein. cDNA encoding Ara h 2 was placed in the pET-24b expression vector. The pET-24 expression vector places a 6× histidine tag at the carboxyl end of the inserted protein. The histidine tag allows the recombinant protein to be purified by affinity purification on a nickel column (HisBind resin). Recombinant Ara h 2 was expressed and purified according to the instructions of the pET system manual. Briefly, expression of the recombinant Ara h 2 was induced in 200 ml cultures of strain BL21 (DE3) *E. coli* with 1 mM IPTG at mid log phase. Cultures were allowed to continue for an additional 3 hours at 36° C. Cells were harvested by centrifugation at 2000× g for 15 minutes and then lysed in denaturing binding buffer (6 M urea, 5 mM imidazole, 0.5 M NaCl, 20 mM Tris-HCl, pH 7.9). Lysates were cleared by centrifugation at 39,000× g for 20 minutes followed by filtration though 0.45 micron filters. The cleared lysate was applied to a 10 ml column of HisBind resin, washed with imidazole wash buffer (20 mM imidazole, 6 M urea, 0.5 M NaCl, 20 mM Tris-HCl, pH 7.9). The recombinant Ara h 2 was then released from the column using elution buffer (1 M imidazole, 0.5 M NaCl, 20 mM Tris-HCl, pH 7.9). The elution buffer was replaced with phosphate buffered saline by dialysis. The purification of recombinant Ara h 2 was followed by SIDS PAGE and immunoblots. Peanut specific serum IgE was used as a primary antibody.

Skin prick tests. The ability of purified native and recombinant Ara h 2 to elicit the IgE mediated degranulation of mast cells was evaluated using prick skin tests in a peanut allergic individual. An individual meeting the criteria for peanut allergy (convincing history or positive double blind placebo controlled food challenge) and a non-allergic control were selected for the testing. Purified native and recombinant Ara h 2 and whole peanut extract (Greer Laboratories, Lenoir, N.C.) were tested. Twenty microliters of the test solution were applied to the forearm of the volunteer and the skin beneath pricked with a sterile needle. Testing was started at the lowest concentration (less than or equal to 1 mg/ml) and increased ten fold each round to the highest concentration or until a positive reaction was observed. Mean diameters of the wheal and erythema were measured and compared to the negative saline control. A positive reaction was defined as a wheal 3 mm larger then the negative control. Histamine was used as the positive control.

Results

Identification of the linear IgE-binding epitopes of Ara h 1, Ara h 2 and Ara h 3 allergens. Epitope mapping was performed on the Ara h 1, Ara h 2 and Ara h 3 allergens by synthesizing each of these proteins in 15 amino acid long overlapping peptides that were offset from each other by 8 amino acids. The peptides were then probed with a pool of serum IgE from 15 patients with documented peanut hypersensitivity. This analysis resulted in multiple IgE binding regions being identified for each allergen. The exact position of each IgE binding epitope was then determined by re-synthesizing these IgE reactive regions as 10 or 15 amino acid long peptides that were offset from each other by two amino acids. These peptides were probed with the same pool of serum IgE from peanut sensitive patients as used before. An example of this procedure for each of the peanut allergens is shown in FIGS. 1-3. FIG. 1 depicts twenty-two 10-mer peptides (SEQ ID NOs. 45-66) that span amino acid residues 82-133 (SEQ ID NO. 44) of the Ara h 1 allergen (SEQ ID NO. 2). This region of the Ara h 1 allergen includes epitopes 4, 5, 6, and 7, as identified in Table 1. FIG. 2 depicts seven 10-mer peptides (SEQ ID NOs. 68-74) that span amino acid residues 55-76 (SEQ ID NO. 67) of the Ara h 2 allergen (SEQ ID NO. 4). This region of the Ara h 2 allergen includes epitopes 6 and 7 as identified in Table 2. FIG. 3 depicts six 15-mer peptides (SEQ ID NOs. 76-81) that span amino acid residues 299-321 (SEQ ID NO. 75) of the Ara h 3 allergen (SEQ ID NO. 6). This region of the Ara h 3 allergen includes epitope 4 as identified in Table 3. This analysis revealed that there were 23 linear IgE binding epitopes on Ara h 1, 10 epitopes on Ara h 2, and 4 epitopes on Ara h 3.

In an effort to determine which, if any, of the epitopes were recognized by the majority of patients with peanut hypersensitivity, each set of epitopes identified for the peanut allergens were synthesized and then probed individually with serum IgE from 10 different patients. All of the patient sera tested recognized multiple epitopes.

Table 1 shows the amino acid sequence and position of each epitope within the Ara h 1 protein (SEQ ID NO. 2) of all 23 IgE binding epitopes mapped to this molecule. Table 2 shows the amino acid sequence and position of each epitope within the Ara h 2 protein (SEQ ID NO. 4) of all 10 IgE binding epitopes mapped to this molecule. Table 3 shows the amino acid sequence and position of each epitope within the Ara h 3 protein (SEQ ID NO. 6) of all 4 IgE binding epitopes mapped to this molecule.

Four epitopes of the Ara h 1 allergen (peptides 1, 3, 4, 17 of Table 1), three epitopes of the Ara h 2 allergen (peptides 3, 6, 7 of Table 2), and one epitope of the Ara h 3 allergen (peptide 2 of Table 3) were immunodominant.

TABLE 1

Ara h 1 IgE binding epitopes

| EPITOPE | AA SEQUENCE | POSITION | SEQ ID NO. |
|---|---|---|---|
| 1 | AKSSPYQKKT | 25-34 | 7 |
| 2 | QEPDDLKQKA | 48-57 | 8 |
| 3 | LEYDPRLVYD | 65-74 | 9 |
| 4 | GERTRGRQPG | 89-98 | 10 |
| 5 | PGDYDDDRRQ | 97-106 | 11 |
| 6 | PRREEGGRWG | 107-116 | 12 |
| 7 | REREEDWRQP | 123-132 | 13 |
| 8 | EDWRRPSHQQ | 134-143 | 14 |
| 9 | QPRKIRPEGR | 143-152 | 15 |
| 10 | TPGQFEDFFP | 294-303 | 16 |
| 11 | SYLQEFSRNT | 311-320 | 17 |
| 12 | FNAEFNEIRR | 325-334 | 18 |
| 13 | EQEERGQRRW | 344-353 | 19 |
| 14 | DITNPINLRE | 393-402 | 20 |
| 15 | NNFGKLFEVK | 409-418 | 21 |
| 16 | GTGNLELVAV | 461-470 | 22 |
| 17 | RRYTARLKEG | 498-507 | 23 |
| 18 | ELHLLGFGIN | 525-534 | 24 |
| 19 | HRIFLAGDKD | 539-548 | 25 |
| 20 | IDQIEKQAKD | 551-560 | 26 |
| 21 | KDLAFPGSGE | 559-568 | 27 |
| 22 | KESHFVSARP | 578-587 | 28 |
| 23 | PEKESPEKED | 597-606 | 29 |

The underlined portions of each peptide are the smallest IgE binding sequences as determined by this analysis. All of these sequences can be found in SEQ ID NO. 2.

TABLE 2

Ara h 2 IgE binding epitopes

| EPITOPE | AA SEQUENCE | POSITION | SEQ ID NO. |
|---|---|---|---|
| 1 | HASARQQWEL | 15-24 | 30 |
| 2 | QWELQGDRRC | 21-30 | 31 |
| 3 | DRRCQSQLER | 27-36 | 32 |
| 4 | LRPCEQHLMQ | 39-48 | 33 |
| 5 | KIQRDEDSYE | 49-58 | 34 |
| 6 | YERDPYSPSQ | 57-66 | 35 |
| 7 | SQDPYSPSPY | 65-74 | 36 |
| 8 | DRLQGRQQEQ | 115-124 | 37 |
| 9 | KRELRNLPQQ | 127-136 | 38 |
| 10 | QRCDLDVESG | 143-152 | 39 |

The underlined portions of each peptide are the smallest IgE binding sequences as determined by this analysis. All of these sequences can be found in SEQ ID NO. 4.

TABLE 3

Ara h 3 IgE binding epitopes

| EPITOPE | AA SEQUENCE | POSITION | SEQ ID NO. |
|---|---|---|---|
| 1 | IETWNPNNQEFECAG | 33-47 | 40 |
| 2 | GNIFSGFTPEFLEQA | 240-254 | 41 |
| 3 | VTVRGGLRILSPDRK | 279-293 | 42 |
| 4 | DEDEYEYDEEDRRRG | 303-317 | 43 |

The underlined portions of each peptide are the smallest IgE binding sequences as determined by this analysis. All of these sequences can be found in SEQ ID NO. 6.

Example 2

Modification of Peanut Allergens to Decrease Allergenicity

The major linear IgE binding epitopes of the peanut allergens were mapped using overlapping peptides synthesized on an activated cellulose membrane and pooled serum IgE from 15 peanut sensitive patients, as described in Example 1. The size of the epitopes ranged from six to fifteen amino acids in length. The amino acids essential to IgE binding in each of the epitopes were determined by synthesizing duplicate peptides with single amino acid changes at each position. These peptides were then probed with pooled serum IgE from 15 patients with peanut hypersensitivity to determine if the changes affected peanut-specific IgE binding. For example, epitope 9 in Table 1 was synthesized with an alanine or methionine residue substituted for one of the amino acids and probed. The following amino acids were substituted (first letter is the one-letter amino acid code for the residue normally at the position, the residue number, followed by the amino acid that was substituted for this residue; the numbers indicate the position of each residue in the Ara h 1 protein, SEQ ID NO. 2): Q143A, P144A; R145A; K146A; 1147A; R148A; P149A; E150A; G151A; R152A; Q143M; P144M; R145M; K146M; 1147M; R148M; P149M; E1SOM; G151M; R152M. The immunoblot strip containing the wild-type and mutated peptides of epitope 9 showed that binding of pooled serum IgE to individual peptides was dramatically reduced when either alanine or methionine was substituted for each of the amino acids at positions 144, 145, and 147-150 of Ara h 1 shown in SEQ ID NO. 2. Changes at positions 144, 145, 147, and 148 of Ara h 1 shown in SEQ ID NO. 2 had the most dramatic effect when methionine was substituted for the wild-type amino acid, resulting in less than 1% of peanut specific 1 gE binding to these peptides. In contrast, the substitution of an alanine for arginine at position 152 of Ara h 1 shown in SEQ ID NO. 2 resulted in increased IgE binding. The remaining Ara h 1 epitopes, and the Ara h 2 and Ara h 3 epitopes, were tested in the same manner and the intensity of IgE binding to each spot was determined as a percentage of IgE binding to the wild-type peptide. Any amino acid substitution that resulted in less than 1% of IgE binding when compared to the wild-type peptide was noted and is indicated in Tables 4-6. Table 4 shows the amino acids that were determined to be critical to IgE binding in each of the Ara h 1 epitopes. Table 5 shows the amino acids that were determined to be critical to IgE binding in each of the Ara h 2 epitopes. Table 6 shows the amino acids that were determined to be critical to IgE binding in each of the Ara h 3 epitopes.

This analysis indicated that each epitope could be mutated to a non-IgE binding-peptide by the substitution of a single amino acid residue.

The results discussed above for Ara h 1, Ara h 2, and Ara h 3demonstrate that once an IgE binding site has been identified, it is possible to reduce IgE binding to this site by altering a single amino acid of the epitope. The observation that alteration of a single amino acid leads to the loss of IgE binding in a population of peanut-sensitive individuals is significant because it suggests that while each patient may display a polyclonal IgE reaction to a particular allergen, IgE from different patients that recognize the same epitope must interact with that epitope in a similar fashion. Besides finding that many epitopes contained more than one residue critical for IgE binding, it was also determined that more than one residue type (ala or met) could be substituted at certain positions in an epitope with similar results. This allows for the design of a hypoallergenic protein that would be effective at blunting allergic reactions for a population of peanut sensitive individuals. Furthermore, the creation of a plant producing a peanut where the IgE binding epitopes of the major allergens have been removed should prevent the development of peanut hypersensitivity in individuals genetically predisposed to this food allergy.

TABLE 4

Amino acids critical to IgE binding of Ara h 1

| EPITOPE | AA SEQUENCE | POSITION | SEQ ID NO. |
|---|---|---|---|
| 1 | AKSSPYQKKT | 23-34 | 7 |
| 2 | QEPDDLKQKA | 48-57 | 8 |
| 3 | LEYDPRLVYD | 65-74 | 9 |
| 4 | GERTRGRQPG | 89-98 | 10 |
| 5 | PGDYDDDRRQ | 97-106 | 11 |
| 6 | PREEGGRWG | 107-116 | 12 |
| 7 | REREEDWRQP | 123-132 | 13 |
| 8 | EDWRRPSHQQ | 134-143 | 14 |
| 9 | QPRKIRPEGR | 143-152 | 15 |
| 10 | TPGQFEDFFP | 294-303 | 16 |
| 11 | SYLQEFSRNT | 311-320 | 17 |
| 12 | FNAEFNEIRR | 325-334 | 18 |
| 13 | EQEERGQRRW | 344-353 | 19 |
| 14 | DITNPINLRE | 393-402 | 20 |
| 15 | NNFGKLFEVK | 409-418 | 21 |
| 17 | RRYTARLKEG | 498-507 | 23 |
| 18 | ELHLLGFGIN | 525-534 | 24 |
| 19 | HRIFLAGDKD | 539-548 | 25 |
| 20 | IDQIEKQAKD | 551-560 | 26 |
| 21 | KDLAFPGSGE | 559-568 | 27 |
| 22 | KESHFVSARP | 578-587 | 28 |

The Ara h 1 IgE binding epitopes are indicated as the single letter amino acid code. The position of each peptide with respect to the Ara h 1 protein (SEQ ID NO. 2) is indicated. The amino acids that, when altered, lead to loss of IgE binding are shown as the bold, underlined residues. Epitopes 16 and 23 were not included in this study because they were recognized by a single patient who was no longer available to the study. All of these sequences can be found in SEQ ID NO. 2.

TABLE 5

Amino acids critical to IgE binding of Ara h 2

| EPITOPE | AA SEQUENCE | POSITION | SEQ ID NO. |
|---|---|---|---|
| 1 | HASARQQWEL | 15-24 | 30 |
| 2 | QWELQGDRRC | 21-30 | 31 |
| 3 | DRRCQSQLER | 27-36 | 32 |
| 4 | LRPCEQHLMQ | 39-48 | 33 |

TABLE 5-continued

Amino acids critical to IgE binding of Ara h 2

| EPITOPE | AA SEQUENCE | POSITION | SEQ ID NO. |
|---|---|---|---|
| 5 | KIQRDEDSYE | 49-58 | 34 |
| 6 | YERDPYSPSQ | 57-66 | 35 |
| 7 | SQDPYSPSPY | 65-74 | 36 |
| 8 | DRLQGRQQEQ | 115-124 | 37 |
| 9 | KRELRNLPQQ | 127-136 | 38 |
| 10 | QRCDLDVESG | 143-152 | 39 |

The Ara h 2 IgE binding epitopes are indicated as the single letter amino acid code. The position of each peptide with respect to the Ara h 2 protein (SEQ ID NO. 4) is indicated. The amino acids that, when altered, lead to loss of IgE binding are shown as the bold, underlined residues. All of these sequences can be found in SEQ ID NO. 4.

TABLE 6

Amino acids critical to IgE binding of Ara h 3

| EPITOPE | AA SEQUENCE | POSITION | SEQ ID NO. |
|---|---|---|---|
| 1 | IETWNPNNQEFECAG | 33-47 | 40 |
| 2 | GNIFSGFTPEFLEQA | 240-254 | 41 |
| 3 | VTVRGGLRILSPDRK | 279-293 | 42 |
| 4 | DEDEYEYDEEDRRRG | 303-317 | 43 |

The Ara h 3 IgE binding epitopes are indicated as the single letter amino acid code. The position of each peptide with respect to the Ara h 3 protein (SEQ ID NO. 6) is indicated. The amino acids that, when altered, lead to loss of IgE binding are shown as the bold, underlined. All of these sequences can be found in SEQ ID NO. 6.

Example 3

A Modified Ara h 2 Protein Binds Less IgE but Similar Amounts of IgG

In order to determine the effect of changes to multiple epitopes within the context of the intact allergen, four epitopes (including the three immunodominant epitopes) of the Ara h 2 allergen were mutagenized and the protein produced recombinantly. The amino acids at position 20, 31, 60, and 67 of the Ara h 2 protein (shown in SEQ ID NO. 4) were changed to alanine by mutagenizing the gene encoding this protein by standard techniques. These residues are located in epitopes 1, 3, 6, and 7 and represent amino acids critical to IgE binding that were determined in Example 2. The modified and wild-type versions of this protein were produced and immunoblot analysis performed using serum from peanut sensitive patients. These results showed that the modified version of this allergen bound significantly less IgE than the wild-type version of these recombinant proteins but bound similar amounts of IgG.

Example 4

A Modified Ara h 2 Protein Retains the Ability to Stimulate T Cells to Proliferate The modified recombinant Ara h 2 protein described in Example 3 was used in T cell proliferation assays to determine if it retained the ability to activate T cells from peanut sensitive individuals. Proliferation assays were performed on T cell lines grown in short-term culture developed from six peanut sensitive patients. T cells lines were stimulated with either 50 μg of crude peanut extract, 10 μg of native Ara h 2, 10 μg of recombinant wild-type Ara h 2, or 10 μg of modified recombinant Ara h 2 protein and the amount of 3H-thymidine determined for each cell line. Results were expressed as the average stimulation index (SI) which reflected the fold increase in 3H-thymidine incorporation exhibited by cells challenged with allergen when compared with media treated controls (FIG. 4).

Example 5

A Modified Ara h 2 Protein Elicits a Smaller Wheal and Flare in Skin Prick Tests of a Peanut Sensitive Individual The modified recombinant Ara h 2 protein described in Example 3 and the wild-type version of this recombinant protein were used in a skin prick test of a peanut sensitive individual. Ten micrograms of these proteins were applied separately to the forearm of a peanut sensitive individual, the skin pricked with a sterile needle, and 10 minutes later any wheal and flare that developed was measured. The wheal and flare produced by the wild-type Ara h 2 protein (8 mm×7 mm) was approximately twice as large as that produced by the modified Ara h 2 protein (4 mm×3 mm). A control subject (no peanut hypersensitivity) tested with the same proteins had no visible wheal and flare but, as expected, gave positive results when challenged with histamine. In addition, the test subject gave no positive results when tested with PBS alone. These results indicate that an allergen with only 40% of its IgE binding epitopes modified (4/10) can give measurable reduction in reactivity in an in vivo test of a peanut sensitive patient.

These same techniques can be used with the other known peanut allergens, Ara h 1 (SEQ ID NOs. 1 and 2), Ara h 3 (SEQ ID NOs. 5 and 6), or any other allergen.

Modifications and variations of the methods and materials described herein will be obvious to those skilled in the art. Such modifications and variations are intended to come within the scope of the appended claims.

SEQUENCE LISTING

<160> NUMBER OF SEQ ID NOS: 81

<210> SEQ ID NO 1
<211> LENGTH: 2032
<212> TYPE: DNA
<213> ORGANISM: Arachis hypogaea

<400> SEQUENCE: 1

```
aataatcata tatattcatc aatcatctat ataagtagta gcaggagcaa tgagagggag     60
ggtttctcca ctgatgctgt tgctagggat ccttgtcctg gcttcagttt ctgcaacgca    120
tgccaagtca tcaccttacc agaagaaaac agagaacccc tgcgcccaga ggtgcctcca    180
gagttgtcaa caggaaccgg atgacttgaa gcaaaaggca tgcgagtctc gctgcaccaa    240
gctcgagtat gatcctcgtt gtgtctatga tcctcgagga cacactgcca ccaccaacca    300
acgttcccct ccaggggagc ggacacgtgg ccgccaaccc ggagactacg atgatgaccg    360
ccgtcaaccc cgaagagagg aaggaggcca tggggaccga ctggaccga gggagcgtga     420 aagagaagaa gactggagac aaccaagaga agattggagg cgaccaagtc atcagcagcc    480
acggaaaata aggcccgaag gaagagaagg agaacaagag tggggaacac caggtagcca    540
tgtgagggaa gaaacatctc ggaacaaccc tttctacttc ccgtcaaggc ggtttagcac    600
ccgctacggg aaccaaaacg gtaggatccg ggtcctgcag aggtttgacc aaaggtcaag    660
gcagtttcag aatctccaga atcaccgtat tgtgcagatc gaggccaaac ctaacactct    720
tgttcttccc aagcacgctg atgctgataa catccttgtt atccagcaag gcaagccac     780 cgtgaccgta gcaaatggca ataacagaaa gagctttaat cttgacgagg ccatgcact     840 cagaatccca tccggtttca tttcctacat cttgaaccgc catgacaacc agaacctcag    900
agtagctaaa atctccatgc ccgttaacac acccggccag tttgaggatt tcttcccggc    960
gagcagccga gaccaatcat cctacttgca gggcttcagc aggaatacgt tggaggccgc   1020
cttcaatgcg gaattcaatg agatacgagg ggtgctgtta aagagaatg caggaggtga    1080 gcaagaggag agagggcaga ggcgatggag tactcggagt agtgagaaca atgaaggagt   1140
gatagtcaaa gtgtcaaagg agcacgttga agaacttact aagcacgcta aatccgtctc   1200
aaagaaaggc tccgaagaag agggagatat caccaaccca atcaacttga gagaaggcga   1260
gcccgatctt tctaacaact tgggaagtt atttgaggtg aagccagaca agaagaaccc    1320
ccagcttcag gacctggaca tgatgctcac ctgtgtagag atcaaagaag gagctttgat   1380
gctcccacac ttcaactcaa aggccatggt tatcgtcgtc gtcaacaaag gaactggaaa   1440
ccttgaactc gtggctgtaa gaaaagagca acaacagagg ggacggcggg aagaagagga   1500
ggacgaagac gaagaagagg agggaagtaa cagagaggtg cgtaggtaca cagcgaggtt   1560
gaaggaaggc gatgtgttca tcatgccagc agctcatcca gtagccatca acgcttcctc   1620
cgaactccat ctgcttggct tcggtatcaa cgctgaaaac aaccacagaa tcttccttgc   1680
aggtgataag gacaatgtga tagaccagat agagaagcaa gcgaaggatt tagcattccc   1740
tgggtcgggt gaacaagttg agaagctcat caaaaaccag aaggaatctc actttgtgag   1800
tgctcgtcct caatctcaat ctcaatctcc gtcgtctcct gagaaagagt ctcctgagaa   1860
agaggatcaa gaggaggaaa accaaggagg gaagggtcca ctcctttcaa ttttgaaggc   1920
ttttaactga gaatggaggc aacttgttat gtatcgataa taagatcacg cttttgtact   1980
ctactatcca aaaacttatc aataaataaa aacgtttgtg cgttgtttct cc           2032
```

<210> SEQ ID NO 2
<211> LENGTH: 626
<212> TYPE: PRT
<213> ORGANISM: Arachis hypogaea

<400> SEQUENCE: 2

```
Met Arg Gly Arg Val Ser Pro Leu Met Leu Leu Leu Gly Ile Leu Val
 1               5                  10                  15
```

```
Leu Ala Ser Val Ser Ala Thr His Ala Lys Ser Ser Pro Tyr Gln Lys
            20                  25                  30

Lys Thr Glu Asn Pro Cys Ala Gln Arg Cys Leu Gln Ser Cys Gln Gln
        35                  40                  45

Glu Pro Asp Asp Leu Lys Gln Lys Ala Cys Glu Ser Arg Cys Thr Lys
    50                  55                  60

Leu Glu Tyr Asp Pro Arg Cys Val Tyr Asp Pro Arg Gly His Thr Gly
65                  70                  75                  80

Thr Thr Asn Gln Arg Ser Pro Pro Gly Glu Arg Thr Arg Gly Arg Gln
                85                  90                  95

Pro Gly Asp Tyr Asp Asp Arg Arg Gln Pro Arg Arg Glu Glu Gly
                    100                 105                 110

Gly Arg Trp Gly Pro Ala Gly Pro Arg Glu Arg Glu Arg Glu Glu Asp
            115                 120                 125

Trp Arg Gln Pro Arg Glu Asp Trp Arg Arg Pro Ser His Gln Gln Pro
        130                 135                 140

Arg Lys Ile Arg Pro Glu Gly Arg Glu Gly Gln Glu Trp Gly Thr
145                 150                 155                 160

Pro Gly Ser His Val Arg Glu Glu Thr Ser Arg Asn Asn Pro Phe Tyr
                165                 170                 175

Phe Pro Ser Arg Arg Phe Ser Thr Arg Tyr Gly Asn Gln Asn Gly Arg
            180                 185                 190

Ile Arg Val Leu Gln Arg Phe Asp Gln Arg Ser Arg Gln Phe Gln Asn
        195                 200                 205

Leu Gln Asn His Arg Ile Val Gln Ile Glu Ala Lys Pro Asn Thr Leu
    210                 215                 220

Val Leu Pro Lys His Ala Asp Ala Asp Asn Ile Leu Val Ile Gln Gln
225                 230                 235                 240

Gly Gln Ala Thr Val Thr Val Ala Asn Gly Asn Asn Arg Lys Ser Phe
                245                 250                 255

Asn Leu Asp Glu Gly His Ala Leu Arg Ile Pro Ser Gly Phe Ile Ser
            260                 265                 270

Tyr Ile Leu Asn Arg His Asp Asn Gln Asn Leu Arg Val Ala Lys Ile
        275                 280                 285

Ser Met Pro Val Asn Thr Pro Gly Gln Phe Glu Asp Phe Phe Pro Ala
    290                 295                 300

Ser Ser Arg Asp Gln Ser Ser Tyr Leu Gln Gly Phe Ser Arg Asn Thr
305                 310                 315                 320

Leu Glu Ala Ala Phe Asn Ala Glu Phe Asn Glu Ile Arg Arg Val Leu
                325                 330                 335

Leu Glu Glu Asn Ala Gly Gly Glu Gln Glu Glu Arg Gly Gln Arg Arg
            340                 345                 350

Trp Ser Thr Arg Ser Ser Glu Asn Asn Glu Gly Val Ile Val Lys Val
        355                 360                 365

Ser Lys Glu His Val Glu Glu Leu Thr Lys His Ala Lys Ser Val Ser
    370                 375                 380

Lys Lys Gly Ser Glu Glu Glu Gly Asp Ile Thr Asn Pro Ile Asn Leu
385                 390                 395                 400

Arg Glu Gly Glu Pro Asp Leu Ser Asn Asn Phe Gly Lys Leu Phe Glu
                405                 410                 415

Val Lys Pro Asp Lys Lys Asn Pro Gln Leu Gln Asp Leu Asp Met Met
            420                 425                 430
```

```
Leu Thr Cys Val Glu Ile Lys Glu Gly Ala Leu Met Leu Pro His Phe
        435                 440                 445

Asn Ser Lys Ala Met Val Ile Val Val Asn Lys Gly Thr Gly Asn
        450                 455                 460

Leu Glu Leu Val Ala Val Arg Lys Glu Gln Gln Arg Gly Arg Arg
465                 470                 475                 480

Glu Glu Glu Glu Asp Glu Asp Glu Glu Glu Gly Ser Asn Arg Glu
                    485                 490                 495

Val Arg Arg Tyr Thr Ala Arg Leu Lys Glu Gly Asp Val Phe Ile Met
                500                 505                 510

Pro Ala Ala His Pro Val Ala Ile Asn Ala Ser Ser Glu Leu His Leu
                515                 520                 525

Leu Gly Phe Gly Ile Asn Ala Glu Asn His Arg Ile Phe Leu Ala
        530                 535                 540

Gly Asp Lys Asp Asn Val Ile Asp Gln Ile Glu Lys Gln Ala Lys Asp
545                 550                 555                 560

Leu Ala Phe Pro Gly Ser Gly Glu Gln Val Glu Lys Leu Ile Lys Asn
                565                 570                 575

Gln Lys Glu Ser His Phe Val Ser Ala Arg Pro Gln Ser Gln Ser Gln
                580                 585                 590

Ser Pro Ser Ser Pro Glu Lys Glu Ser Pro Lys Glu Asp Gln Glu
        595                 600                 605

Glu Glu Asn Gln Gly Gly Lys Gly Pro Leu Leu Ser Ile Leu Lys Ala
        610                 615                 620

Phe Asn
625

<210> SEQ ID NO 3
<211> LENGTH: 474
<212> TYPE: DNA
<213> ORGANISM: Arachis hypogaea

<400> SEQUENCE: 3
ctcaccatac tagtagccct cgccttttc ctcctcgctg cccacgcatc tgcgaggcag       60
cagtgggaac tccaaggaga cagaagatgc cagagccagc tcgagagggc gaacctgagg      120
ccctgcgagc aacatctcat gcagaagatc aacgtgacg aggattcata tgaacgggac      180
ccgtacagcc ctagtcagga tccgtacagc cctagtccat atgatcggag aggcgctgga      240
tcctctcagc accaagagag gtgttgcaat gagctgaacg agtttgagaa caaccaaagg      300
tgcatgtgcg aggcattgca acagatcatg agaaccaga gcgataggtt gcaggggagg      360
caacaggagc aacagttcaa gagggagctc aggaacttgc ctcaacagtg cggccttagg      420
gcaccacagc gttgcgactt ggacgtcgaa agtggcggca gagacagata ctaa            474

<210> SEQ ID NO 4
<211> LENGTH: 157
<212> TYPE: PRT
<213> ORGANISM: Arachis hypogaea

<400> SEQUENCE: 4

Leu Thr Ile Leu Val Ala Leu Ala Leu Phe Leu Leu Ala Ala His Ala
1               5                   10                  15

Ser Ala Arg Gln Gln Trp Glu Leu Gln Gly Asp Arg Arg Cys Gln Ser
                20                  25                  30

Gln Leu Glu Arg Ala Asn Leu Arg Pro Cys Glu Gln His Leu Met Gln
        35                  40                  45
```

| | | | | | | | | | | | |
|---|---|---|---|---|---|---|---|---|---|---|---|
| Lys | Ile | Gln | Arg | Asp | Glu | Asp | Ser | Tyr | Glu | Arg | Asp | Pro | Tyr | Ser | Pro |
| | | | 50 | | | | | 55 | | | | | 60 | | |

```
        Lys Ile Gln Arg Asp Glu Asp Ser Tyr Glu Arg Asp Pro Tyr Ser Pro
                        50                  55                  60

Ser Gln Asp Pro Tyr Ser Pro Ser Pro Tyr Arg Arg Gly Ala Gly
         65                  70                  75                  80

Ser Ser Gln His Gln Glu Arg Cys Cys Asn Glu Leu Asn Glu Phe Glu
                            85                  90                  95

Asn Asn Gln Arg Cys Met Cys Glu Ala Leu Gln Ile Met Glu Asn
                        100                 105                 110

Gln Ser Asp Arg Leu Gln Gly Arg Gln Gln Glu Gln Gln Phe Lys Arg
                        115                 120                 125

Glu Leu Arg Asn Leu Pro Gln Gln Cys Gly Leu Arg Ala Pro Gln Arg
                        130                 135                 140

Cys Asp Leu Asp Val Glu Ser Gly Gly Arg Asp Arg Tyr
        145                 150                 155

<210> SEQ ID NO 5
        <211> LENGTH: 1524
        <212> TYPE: DNA
        <213> ORGANISM: Arachis hypogaea

<400> SEQUENCE: 5
cggcagcaac cggaggagaa cgcgtgccag ttccagcgcc tcaatgcgca gagacctgac     60
aatcgcattg aatcagaggg cggttacatt gagacttgga accccaacaa ccaggagttc    120
gaatgcgccg cgtcgccct ctctcgctta gtcctccgcc gcaacgccct tcgtaggcct    180
ttctactcca atgctcccca ggagatcttc atccagcaag aaggggata ctttggttg    240 atattccctg gttgtcctag acactatgaa gagcctcaca caaggtcg tcgatctcag    300 tcccaaagac caccaagacg tctccaagga gaagaccaaa gccaacagca cgagatagt    360 caccagaagg tgcaccgttt cgatgagggt gatctcattg cagttccac cggtgttgct    420 ttctggctct acaacgacca cgacactgat gttgttgctg tttctcttac tgacaccaac    480
aacaacgaca accagcttga tcagttcccc aggagattca atttggctgg aacacggag    540 caagagttct taaggtacca gcaacaaagc agacaaagca gacgaagaag cttaccatat    600
agcccataca gcccgcaaag tcagcctaga caagaagagc gtgaatttag ccctcgagga    660
cagcacagcc gcagagaacg agcaggacaa gaagaagaaa cgaaggtgg aaacatcttc    720 agcggcttca cgccggagtt cctgaacaa gccttccagg ttgacgacag acagatagtg    780
caaaacctaa gaggcgagac cgagagtgaa gagagggag ccattgtgac agtgagggga    840
ggcctcagaa tcttgagccc agatagaaag agacgtgccg acgaagaaga ggaatacgat    900
gaagatgaat atgaatacga tgaagaggat agaaggcgtg gcaggggaag cagaggcagg    960
gggaatggta ttgaagagac gatctgcacc gcaagtgcta aaagaacat tggtagaaac   1020 agatcccctg acatctacaa ccctcaagct ggttcactca aactgccaa cgatctcaac   1080 cttctaatac ttaggtggct tggacctagt gctgaatatg gaaatctcta caggaatgca   1140
ttgtttgtcg ctcactacaa caccaacgca cacagcatca tatatcgatt gaggggacgg   1200
gctcacgtgc aagtcgtgga cagcaacggc aacagagtgt acgacgagga gcttcaagag   1260
ggtcacgtgc ttgtggtgcc acagaacttc gccgtcgctg gaaagtccca gagcgagaac   1320
ttcgaatacg tggcattcaa gacagactca aggcccagca tagccaacct cgccggtgaa   1380
aactccgtca tagataaccct gccggaggag gtggttgcaa attcatatgg cctcaaaagg   1440
gagcaggcaa ggcagcttaa gaacaacaac ccccttcaagt tcttcgttcc accgtctcag   1500
```
cagtctccga gggctgtggc ttaa                                           1524

<210> SEQ ID NO 6
<211> LENGTH: 510
<212> TYPE: PRT
<213> ORGANISM: Arachis hypogaea

<400> SEQUENCE: 6

Ile Ser Phe Arg Gln Gln Pro Glu Glu Asn Ala Cys Gln Phe Gln Arg
 1               5                  10                  15

Leu Asn Ala Gln Arg Pro Asp Asn Arg Ile Glu Ser Glu Gly Gly Tyr
            20                  25                  30

Ile Glu Thr Trp Asn Pro Asn Gln Glu Phe Glu Cys Ala Gly Val
        35                  40                  45

Ala Leu Ser Arg Leu Val Leu Arg Arg Asn Ala Leu Arg Arg Pro Phe
 50                  55                  60

Tyr Ser Asn Ala Pro Gln Glu Ile Phe Ile Gln Gln Gly Arg Gly Tyr
 65                  70                  75                  80

Phe Gly Leu Ile Phe Pro Gly Cys Pro Arg His Tyr Glu Glu Pro His
                85                  90                  95

Thr Gln Gly Arg Arg Ser Gln Ser Gln Arg Pro Arg Arg Leu Gln
            100                 105                 110

Gly Glu Asp Gln Ser Gln Gln Arg Asp Ser His Gln Lys Val His
        115                 120                 125

Arg Phe Asp Glu Gly Asp Leu Ile Ala Val Pro Thr Gly Val Ala Phe
130                 135                 140

Trp Leu Tyr Asn Asp His Asp Thr Asp Val Val Ala Val Ser Leu Thr
145                 150                 155                 160

Asp Thr Asn Asn Asp Asn Gln Leu Asp Gln Phe Pro Arg Arg Phe
                165                 170                 175

Asn Leu Ala Gly Asn Thr Glu Gln Glu Phe Leu Arg Tyr Gln Gln Gln
            180                 185                 190

Ser Arg Gln Ser Arg Arg Ser Leu Pro Tyr Ser Pro Tyr Ser Pro
        195                 200                 205

Gln Ser Gln Pro Arg Gln Glu Glu Arg Glu Phe Ser Pro Arg Gly Gln
210                 215                 220

His Ser Arg Arg Glu Arg Ala Gly Gln Glu Glu Asn Glu Gly Gly
225                 230                 235                 240

Asn Ile Phe Ser Gly Phe Thr Pro Glu Phe Leu Glu Gln Ala Phe Gln
                245                 250                 255

Val Asp Asp Arg Gln Ile Val Gln Asn Leu Arg Gly Glu Thr Glu Ser
            260                 265                 270

Glu Glu Glu Gly Ala Ile Val Thr Val Arg Gly Gly Leu Arg Ile Leu
        275                 280                 285

Ser Pro Asp Arg Lys Arg Arg Ala Asp Glu Glu Glu Tyr Asp Glu
290                 295                 300

Asp Glu Tyr Glu Tyr Asp Glu Glu Asp Arg Arg Gly Arg Gly Ser
305                 310                 315                 320

Arg Gly Arg Gly Asn Gly Ile Glu Glu Thr Ile Cys Thr Ala Ser Ala
                325                 330                 335

Lys Lys Asn Ile Gly Arg Asn Arg Ser Pro Asp Ile Tyr Asn Pro Gln
            340                 345                 350

Ala Gly Ser Leu Lys Thr Ala Asn Asp Leu Asn Leu Leu Ile Leu Arg
        355                 360                 365

```
Trp Leu Gly Pro Ser Ala Glu Tyr Gly Asn Leu Tyr Arg Asn Ala Leu
    370                 375                 380

Phe Val Ala His Tyr Asn Thr Asn Ala His Ser Ile Ile Tyr Arg Leu
385                 390                 395                 400

Arg Gly Arg Ala His Val Gln Val Val Asp Ser Asn Gly Asn Arg Val
                405                 410                 415

Tyr Asp Glu Glu Leu Gln Glu Gly His Val Leu Val Val Pro Gln Asn
                420                 425                 430

Phe Ala Val Ala Gly Lys Ser Gln Ser Glu Asn Phe Glu Tyr Val Ala
            435                 440                 445

Phe Lys Thr Asp Ser Arg Pro Ser Ile Ala Asn Leu Ala Gly Glu Asn
    450                 455                 460

Ser Val Ile Asp Asn Leu Pro Glu Glu Val Val Ala Asn Ser Tyr Gly
465                 470                 475                 480

Leu Gln Arg Glu Gln Ala Arg Gln Leu Lys Asn Asn Asn Pro Phe Lys
                485                 490                 495

Phe Phe Val Pro Pro Ser Gln Gln Ser Pro Arg Ala Val Ala
                500                 505                 510

<210> SEQ ID NO 7
<211> LENGTH: 10
<212> TYPE: PRT
<213> ORGANISM: Arachis hypogaea

<400> SEQUENCE: 7

Ala Lys Ser Ser Pro Tyr Gln Lys Lys Thr
1               5                   10

<210> SEQ ID NO 8
<211> LENGTH: 10
<212> TYPE: PRT
<213> ORGANISM: Arachis hypogaea

<400> SEQUENCE: 8

Gln Glu Pro Asp Asp Leu Lys Gln Lys Ala
1               5                   10

<210> SEQ ID NO 9
<211> LENGTH: 10
<212> TYPE: PRT
<213> ORGANISM: Arachis hypogaea

<400> SEQUENCE: 9

Leu Glu Tyr Asp Pro Arg Leu Val Tyr Asp
1               5                   10

<210> SEQ ID NO 10
<211> LENGTH: 10
<212> TYPE: PRT
<213> ORGANISM: Arachis hypogaea

<400> SEQUENCE: 10

Gly Glu Arg Thr Arg Gly Arg Gln Pro Gly
1               5                   10

<210> SEQ ID NO 11
<211> LENGTH: 10
<212> TYPE: PRT
<213> ORGANISM: Arachis hypogaea

<400> SEQUENCE: 11
```

Pro Gly Asp Tyr Asp Asp Arg Arg Gln
1               5                   10

<210> SEQ ID NO 12
<211> LENGTH: 10
<212> TYPE: PRT
<213> ORGANISM: Arachis hypogaea

<400> SEQUENCE: 12

Pro Arg Arg Glu Glu Gly Gly Arg Trp Gly
1               5                   10

<210> SEQ ID NO 13
<211> LENGTH: 10
<212> TYPE: PRT
<213> ORGANISM: Arachis hypogaea

<400> SEQUENCE: 13

Arg Glu Arg Glu Glu Asp Trp Arg Gln Pro
1               5                   10

<210> SEQ ID NO 14
<211> LENGTH: 10
<212> TYPE: PRT
<213> ORGANISM: Arachis hypogaea

<400> SEQUENCE: 14

Glu Asp Trp Arg Arg Pro Ser His Gln Gln
1               5                   10

<210> SEQ ID NO 15
<211> LENGTH: 10
<212> TYPE: PRT
<213> ORGANISM: Arachis hypogaea

<400> SEQUENCE: 15

Gln Pro Arg Lys Ile Arg Pro Glu Gly Arg
1               5                   10

<210> SEQ ID NO 16
<211> LENGTH: 10
<212> TYPE: PRT
<213> ORGANISM: Arachis hypogaea

<400> SEQUENCE: 16

Thr Pro Gly Gln Phe Glu Asp Phe Phe Pro
1               5                   10

<210> SEQ ID NO 17
<211> LENGTH: 10
<212> TYPE: PRT
<213> ORGANISM: Arachis hypogaea

<400> SEQUENCE: 17

Ser Tyr Leu Gln Glu Phe Ser Arg Asn Thr
1               5                   10

<210> SEQ ID NO 18
<211> LENGTH: 10
<212> TYPE: PRT
<213> ORGANISM: Arachis hypogaea

<400> SEQUENCE: 18

Phe Asn Ala Glu Phe Asn Glu Ile Arg Arg

-continued

<210> SEQ ID NO 19
<211> LENGTH: 10
<212> TYPE: PRT
<213> ORGANISM: Arachis hypogaea

<400> SEQUENCE: 19

Glu Gln Glu Glu Arg Gly Gln Arg Arg Trp
1               5                   10

<210> SEQ ID NO 20
<211> LENGTH: 10
<212> TYPE: PRT
<213> ORGANISM: Arachis hypogaea

<400> SEQUENCE: 20

Asp Ile Thr Asn Pro Ile Asn Leu Arg Glu
1               5                   10

<210> SEQ ID NO 21
<211> LENGTH: 10
<212> TYPE: PRT
<213> ORGANISM: Arachis hypogaea

<400> SEQUENCE: 21

Asn Asn Phe Gly Lys Leu Phe Glu Val Lys
1               5                   10

<210> SEQ ID NO 22
<211> LENGTH: 10
<212> TYPE: PRT
<213> ORGANISM: Arachis hypogaea

<400> SEQUENCE: 22

Gly Thr Gly Asn Leu Glu Leu Val Ala Val
1               5                   10

<210> SEQ ID NO 23
<211> LENGTH: 10
<212> TYPE: PRT
<213> ORGANISM: Arachis hypogaea

<400> SEQUENCE: 23

Arg Arg Tyr Thr Ala Arg Leu Lys Glu Gly
1               5                   10

<210> SEQ ID NO 24
<211> LENGTH: 10
<212> TYPE: PRT
<213> ORGANISM: Arachis hypogaea

<400> SEQUENCE: 24

Glu Leu His Leu Leu Gly Phe Gly Ile Asn
1               5                   10

<210> SEQ ID NO 25
<211> LENGTH: 10
<212> TYPE: PRT
<213> ORGANISM: Arachis hypogaea

<400> SEQUENCE: 25

His Arg Ile Phe Leu Ala Gly Asp Lys Asp
1               5                   10

```
<210> SEQ ID NO 26
<211> LENGTH: 10
<212> TYPE: PRT
<213> ORGANISM: Arachis hypogaea

<400> SEQUENCE: 26

Ile Asp Gln Ile Glu Lys Gln Ala Lys Asp
 1               5                  10

<210> SEQ ID NO 27
<211> LENGTH: 10
<212> TYPE: PRT
<213> ORGANISM: Arachis hypogaea

<400> SEQUENCE: 27

Lys Asp Leu Ala Phe Pro Gly Ser Gly Glu
 1               5                  10

<210> SEQ ID NO 28
<211> LENGTH: 10
<212> TYPE: PRT
<213> ORGANISM: Arachis hypogaea

<400> SEQUENCE: 28

Lys Glu Ser His Phe Val Ser Ala Arg Pro
 1               5                  10

<210> SEQ ID NO 29
<211> LENGTH: 10
<212> TYPE: PRT
<213> ORGANISM: Arachis hypogaea

<400> SEQUENCE: 29

Pro Glu Lys Glu Ser Pro Glu Lys Glu Asp
 1               5                  10

<210> SEQ ID NO 30
<211> LENGTH: 10
<212> TYPE: PRT
<213> ORGANISM: Arachis hypogaea

<400> SEQUENCE: 30

His Ala Ser Ala Arg Gln Gln Trp Glu Leu
 1               5                  10

<210> SEQ ID NO 31
<211> LENGTH: 10
<212> TYPE: PRT
<213> ORGANISM: Arachis hypogaea

<400> SEQUENCE: 31

Gln Trp Glu Leu Gln Gly Asp Arg Arg Cys
 1               5                  10

<210> SEQ ID NO 32
<211> LENGTH: 10
<212> TYPE: PRT
<213> ORGANISM: Arachis hypogaea

<400> SEQUENCE: 32

Asp Arg Arg Cys Gln Ser Gln Leu Glu Arg
 1               5                  10

<210> SEQ ID NO 33
```

```
<211> LENGTH: 10
<212> TYPE: PRT
<213> ORGANISM: Arachis hypogaea

<400> SEQUENCE: 33

Leu Arg Pro Cys Glu Gln His Leu Met Gln
 1               5                  10

<210> SEQ ID NO 34
<211> LENGTH: 10
<212> TYPE: PRT
<213> ORGANISM: Arachis hypogaea

<400> SEQUENCE: 34

Lys Ile Gln Arg Asp Glu Asp Ser Tyr Glu
 1               5                  10

<210> SEQ ID NO 35
<211> LENGTH: 10
<212> TYPE: PRT
<213> ORGANISM: Arachis hypogaea

<400> SEQUENCE: 35

Tyr Glu Arg Asp Pro Tyr Ser Pro Ser Gln
 1               5                  10

<210> SEQ ID NO 36
<211> LENGTH: 10
<212> TYPE: PRT
<213> ORGANISM: Arachis hypogaea

<400> SEQUENCE: 36

Ser Gln Asp Pro Tyr Ser Pro Ser Pro Tyr
 1               5                  10

<210> SEQ ID NO 37
<211> LENGTH: 10
<212> TYPE: PRT
<213> ORGANISM: Arachis hypogaea

<400> SEQUENCE: 37

Asp Arg Leu Gln Gly Arg Gln Gln Glu Gln
 1               5                  10

<210> SEQ ID NO 38
<211> LENGTH: 10
<212> TYPE: PRT
<213> ORGANISM: Arachis hypogaea

<400> SEQUENCE: 38

Lys Arg Glu Leu Arg Asn Leu Pro Gln Gln
 1               5                  10

<210> SEQ ID NO 39
<211> LENGTH: 10
<212> TYPE: PRT
<213> ORGANISM: Arachis hypogaea

<400> SEQUENCE: 39

Gln Arg Cys Asp Leu Asp Val Glu Ser Gly
 1               5                  10

<210> SEQ ID NO 40
<211> LENGTH: 15
<212> TYPE: PRT
```

```
<213> ORGANISM: Arachis hypogaea

<400> SEQUENCE: 40

Ile Glu Thr Trp Asn Pro Asn Asn Gln Glu Phe Glu Cys Ala Gly
 1               5                  10                  15

<210> SEQ ID NO 41
<211> LENGTH: 15
<212> TYPE: PRT
<213> ORGANISM: Arachis hypogaea

<400> SEQUENCE: 41

Gly Asn Ile Phe Ser Gly Phe Thr Pro Glu Phe Leu Glu Gln Ala
 1               5                  10                  15

<210> SEQ ID NO 42
<211> LENGTH: 15
<212> TYPE: PRT
<213> ORGANISM: Arachis hypogaea

<400> SEQUENCE: 42

Val Thr Val Arg Gly Gly Leu Arg Ile Leu Ser Pro Asp Arg Lys
 1               5                  10                  15

<210> SEQ ID NO 43
<211> LENGTH: 15
<212> TYPE: PRT
<213> ORGANISM: Arachis hypogaea

<400> SEQUENCE: 43

Asp Glu Asp Glu Tyr Glu Tyr Asp Glu Glu Asp Arg Arg Arg Gly
 1               5                  10                  15

<210> SEQ ID NO 44
<211> LENGTH: 52
<212> TYPE: PRT
<213> ORGANISM: Arachis hypogaea

<400> SEQUENCE: 44

Thr Asn Gln Arg Ser Pro Pro Gly Glu Arg Thr Arg Gly Arg Gln Pro
 1               5                  10                  15

Gly Asp Tyr Asp Asp Asp Arg Arg Gln Pro Arg Arg Glu Glu Gly Gly
                20                  25                  30

Arg Trp Gly Pro Ala Gly Pro Arg Glu Arg Glu Arg Glu Asp Trp
         35                  40                  45

Arg Gln Pro Arg
     50

<210> SEQ ID NO 45
<211> LENGTH: 10
<212> TYPE: PRT
<213> ORGANISM: Arachis hypogaea

<400> SEQUENCE: 45

Thr Asn Gln Arg Ser Pro Pro Gly Glu Arg
 1               5                  10

<210> SEQ ID NO 46
<211> LENGTH: 10
<212> TYPE: PRT
<213> ORGANISM: Arachis hypogaea

<400> SEQUENCE: 46
```

Gln Arg Ser Pro Pro Gly Glu Arg Thr Arg
1               5                   10

<210> SEQ ID NO 47
<211> LENGTH: 10
<212> TYPE: PRT
<213> ORGANISM: Arachis hypogaea

<400> SEQUENCE: 47

Ser Pro Pro Gly Glu Arg Thr Arg Gly Arg
1               5                   10

<210> SEQ ID NO 48
<211> LENGTH: 10
<212> TYPE: PRT
<213> ORGANISM: Arachis hypogaea

<400> SEQUENCE: 48

Pro Gly Glu Arg Thr Arg Gly Arg Gln Pro
1               5                   10

<210> SEQ ID NO 49
<211> LENGTH: 10
<212> TYPE: PRT
<213> ORGANISM: Arachis hypogaea

<400> SEQUENCE: 49

Glu Arg Thr Arg Gly Arg Gln Pro Gly Asp
1               5                   10

<210> SEQ ID NO 50
<211> LENGTH: 10
<212> TYPE: PRT
<213> ORGANISM: Arachis hypogaea

<400> SEQUENCE: 50

Thr Arg Gly Arg Gln Pro Gly Asp Tyr Asp
1               5                   10

<210> SEQ ID NO 51
<211> LENGTH: 10
<212> TYPE: PRT
<213> ORGANISM: Arachis hypogaea

<400> SEQUENCE: 51

Gly Arg Gln Pro Gly Asp Tyr Asp Asp Asp
1               5                   10

<210> SEQ ID NO 52
<211> LENGTH: 10
<212> TYPE: PRT
<213> ORGANISM: Arachis hypogaea

<400> SEQUENCE: 52

Gln Pro Gly Asp Tyr Asp Asp Asp Arg Arg
1               5                   10

<210> SEQ ID NO 53
<211> LENGTH: 10
<212> TYPE: PRT
<213> ORGANISM: Arachis hypogaea

<400> SEQUENCE: 53

Gly Asp Tyr Asp Asp Asp Arg Arg Gln Pro
1               5                   10

<210> SEQ ID NO 54
<211> LENGTH: 10
<212> TYPE: PRT
<213> ORGANISM: Arachis hypogaea

<400> SEQUENCE: 54

Tyr Asp Asp Arg Arg Gln Pro Arg Arg
  1               5                  10

<210> SEQ ID NO 55
<211> LENGTH: 10
<212> TYPE: PRT
<213> ORGANISM: Arachis hypogaea

<400> SEQUENCE: 55

Asp Asp Arg Arg Gln Pro Arg Arg Glu Glu
  1               5                  10

<210> SEQ ID NO 56
<211> LENGTH: 10
<212> TYPE: PRT
<213> ORGANISM: Arachis hypogaea

<400> SEQUENCE: 56

Arg Arg Gln Pro Arg Arg Glu Glu Gly Gly
  1               5                  10

<210> SEQ ID NO 57
<211> LENGTH: 10
<212> TYPE: PRT
<213> ORGANISM: Arachis hypogaea

<400> SEQUENCE: 57

Gln Pro Arg Arg Glu Glu Gly Gly Arg Trp
  1               5                  10

<210> SEQ ID NO 58
<211> LENGTH: 10
<212> TYPE: PRT
<213> ORGANISM: Arachis hypogaea

<400> SEQUENCE: 58

Arg Arg Glu Glu Gly Gly Arg Trp Gly Pro
  1               5                  10

<210> SEQ ID NO 59
<211> LENGTH: 10
<212> TYPE: PRT
<213> ORGANISM: Arachis hypogaea

<400> SEQUENCE: 59

Glu Glu Gly Gly Arg Trp Gly Pro Ala Gly
  1               5                  10

<210> SEQ ID NO 60
<211> LENGTH: 10
<212> TYPE: PRT
<213> ORGANISM: Arachis hypogaea

<400> SEQUENCE: 60

Gly Gly Arg Trp Gly Pro Ala Gly Pro Arg
  1               5                  10

<210> SEQ ID NO 61
<211> LENGTH: 10
<212> TYPE: PRT
<213> ORGANISM: Arachis hypogaea

<400> SEQUENCE: 61

Arg Trp Gly Pro Ala Gly Pro Arg Glu Arg
 1               5                  10

<210> SEQ ID NO 62
<211> LENGTH: 10
<212> TYPE: PRT
<213> ORGANISM: Arachis hypogaea

<400> SEQUENCE: 62

Gly Pro Ala Gly Pro Arg Glu Arg Glu Arg
 1               5                  10

<210> SEQ ID NO 63
<211> LENGTH: 10
<212> TYPE: PRT
<213> ORGANISM: Arachis hypogaea

<400> SEQUENCE: 63

Ala Gly Pro Arg Glu Arg Glu Arg Glu Glu
 1               5                  10

<210> SEQ ID NO 64
<211> LENGTH: 10
<212> TYPE: PRT
<213> ORGANISM: Arachis hypogaea

<400> SEQUENCE: 64

Pro Arg Glu Arg Glu Arg Glu Glu Asp Trp
 1               5                  10

<210> SEQ ID NO 65
<211> LENGTH: 10
<212> TYPE: PRT
<213> ORGANISM: Arachis hypogaea

<400> SEQUENCE: 65

Glu Arg Glu Arg Glu Glu Asp Trp Arg Gln
 1               5                  10

<210> SEQ ID NO 66
<211> LENGTH: 10
<212> TYPE: PRT
<213> ORGANISM: Arachis hypogaea

<400> SEQUENCE: 66

Glu Arg Glu Glu Asp Trp Arg Gln Pro Arg
 1               5                  10

<210> SEQ ID NO 67
<211> LENGTH: 22
<212> TYPE: PRT
<213> ORGANISM: Arachis hypogaea

<400> SEQUENCE: 67

Asp Ser Tyr Glu Arg Asp Pro Tyr Ser Pro Ser Gln Asp Pro Tyr Ser
 1               5                  10                  15

Pro Ser Pro Tyr Asp Arg
                20

```
<210> SEQ ID NO 68
<211> LENGTH: 10
<212> TYPE: PRT
<213> ORGANISM: Arachis hypogaea

<400> SEQUENCE: 68

Asp Ser Tyr Glu Arg Asp Pro Tyr Ser Pro
 1               5                  10

<210> SEQ ID NO 69
<211> LENGTH: 10
<212> TYPE: PRT
<213> ORGANISM: Arachis hypogaea

<400> SEQUENCE: 69

Tyr Glu Arg Asp Pro Tyr Ser Pro Ser Gln
 1               5                  10

<210> SEQ ID NO 70
<211> LENGTH: 10
<212> TYPE: PRT
<213> ORGANISM: Arachis hypogaea

<400> SEQUENCE: 70

Arg Asp Pro Tyr Ser Pro Ser Gln Asp Pro
 1               5                  10

<210> SEQ ID NO 71
<211> LENGTH: 10
<212> TYPE: PRT
<213> ORGANISM: Arachis hypogaea

<400> SEQUENCE: 71

Pro Tyr Ser Pro Ser Gln Asp Pro Tyr Ser
 1               5                  10

<210> SEQ ID NO 72
<211> LENGTH: 10
<212> TYPE: PRT
<213> ORGANISM: Arachis hypogaea

<400> SEQUENCE: 72

Ser Pro Ser Gln Asp Pro Tyr Ser Pro Ser
 1               5                  10

<210> SEQ ID NO 73
<211> LENGTH: 10
<212> TYPE: PRT
<213> ORGANISM: Arachis hypogaea

<400> SEQUENCE: 73

Ser Gln Asp Pro Tyr Ser Pro Ser Pro Tyr
 1               5                  10

<210> SEQ ID NO 74
<211> LENGTH: 10
<212> TYPE: PRT
<213> ORGANISM: Arachis hypogaea

<400> SEQUENCE: 74

Asp Pro Tyr Ser Pro Ser Pro Tyr Asp Arg
 1               5                  10

<210> SEQ ID NO 75
```

```
<211> LENGTH: 23
<212> TYPE: PRT
<213> ORGANISM: Arachis hypogaea

<400> SEQUENCE: 75

Glu Glu Glu Tyr Asp Glu Asp Glu Tyr Glu Tyr Asp Glu Glu Asp Arg
 1               5                  10                  15

Arg Arg Gly Arg Gly Ser Arg
            20

<210> SEQ ID NO 76
<211> LENGTH: 15
<212> TYPE: PRT
<213> ORGANISM: Arachis hypogaea

<400> SEQUENCE: 76

Glu Glu Glu Tyr Asp Glu Asp Glu Tyr Glu Tyr Asp Glu Glu Asp
 1               5                  10                  15

<210> SEQ ID NO 77
<211> LENGTH: 15
<212> TYPE: PRT
<213> ORGANISM: Arachis hypogaea

<400> SEQUENCE: 77

Glu Tyr Asp Glu Asp Glu Tyr Glu Tyr Asp Glu Glu Asp Arg Arg
 1               5                  10                  15

<210> SEQ ID NO 78
<211> LENGTH: 15
<212> TYPE: PRT
<213> ORGANISM: Arachis hypogaea

<400> SEQUENCE: 78

Asp Glu Asp Glu Tyr Glu Tyr Asp Glu Glu Asp Arg Arg Arg Gly
 1               5                  10                  15

<210> SEQ ID NO 79
<211> LENGTH: 15
<212> TYPE: PRT
<213> ORGANISM: Arachis hypogaea

<400> SEQUENCE: 79

Asp Glu Tyr Glu Tyr Asp Glu Glu Asp Arg Arg Arg Gly Arg Gly
 1               5                  10                  15

<210> SEQ ID NO 80
<211> LENGTH: 15
<212> TYPE: PRT
<213> ORGANISM: Arachis hypogaea

<400> SEQUENCE: 80

Tyr Glu Tyr Asp Glu Glu Asp Arg Arg Arg Gly Arg Gly Ser Arg
 1               5                  10                  15

<210> SEQ ID NO 81
<211> LENGTH: 15
<212> TYPE: PRT
<213> ORGANISM: Arachis hypogaea

<400> SEQUENCE: 81

Tyr Asp Glu Glu Asp Arg Arg Arg Gly Arg Gly Ser Arg Gly Argu
 1               5                  10                  15
```

We claim:

1. An isolated nucleic acid that encodes a protein whose sequence is shown in SEQ ID NO. 6.

2. An isolated nucleic acid that comprises the sequence shown in SEQ ID NO. 5.

3. A vector comprising the nucleic acid of claim 1.

4. A vector comprising the nucleic acid of claim 2.

5. An isolated host cell comprising the nucleic acid of claim 1.

6. An isolated nucleic acid that encodes a protein whose sequence is identical to that shown in SEQ ID NO. 6, except that it comprises one or more mutated IgE epitopes and wherein the one or more IgE epitopes are shown in SEQ ID NO. 40, 41, 42, or 43; wherein said protein exhibits reduced IgE binding as compared to a protein whose sequence is identical to SEQ ID NO. 6.

7. An isolated host cell comprising the nucleic acid of claim 2.

8. A vector comprising the nucleic acid of claim 6.

9. An isolated host cell comprising the nucleic acid of claim 6.

* * * * *